United States Patent
Tripp et al.

(10) Patent No.: US 12,194,065 B2
(45) Date of Patent: Jan. 14, 2025

(54) METHODS AND COMPOSITIONS TO ENHANCE METABOLIC DETOXIFICATION SYSTEMS

(71) Applicant: Nature's Sunshine Products, Inc., Lehi, UT (US)

(72) Inventors: Matthew L. Tripp, Camano Island, WA (US); Clinton J. Dahlberg, Saratoga Springs, UT (US); John G. Babish, Brooktondale, NY (US); Joseph Lamb, Lehi, UT (US); Joseph J. Ou, Saratoga Springs, UT (US); Veera R. Konda, Draper, UT (US); Sarah Elison, Spanish Fork, UT (US); Wei Gao, Lehi, UT (US); Jay Bhandari, Salt Lake City, UT (US)

(73) Assignee: Nature's Sunshine Products, Inc., Lehi, UT (US)

( * ) Notice: Subject to any disclaimer, the term of this patent is extended or adjusted under 35 U.S.C. 154(b) by 182 days.

(21) Appl. No.: 16/761,489

(22) PCT Filed: Nov. 5, 2018

(86) PCT No.: PCT/US2018/059285
§ 371 (c)(1),
(2) Date: May 4, 2020

(87) PCT Pub. No.: WO2019/090273
PCT Pub. Date: May 9, 2019

(65) Prior Publication Data
US 2021/0038656 A1    Feb. 11, 2021

Related U.S. Application Data

(60) Provisional application No. 62/581,567, filed on Nov. 3, 2017.

(51) Int. Cl.
*A61K 31/00*    (2006.01)
*A23L 33/00*    (2016.01)
(Continued)

(52) U.S. Cl.
CPC .......... *A61K 35/742* (2013.01); *A23L 33/105* (2016.08); *A23L 33/135* (2016.08);
(Continued)

(58) Field of Classification Search
CPC ................................................... A61K 31/00
See application file for complete search history.

(56) References Cited

U.S. PATENT DOCUMENTS 6,086,886 A     7/2000   Guo
10,434,131 B2   10/2019  Tripp et al.
(Continued)

FOREIGN PATENT DOCUMENTS

CN    102630819 A  *  8/2012
CN    106858117 A  *  6/2017
(Continued)

OTHER PUBLICATIONS

Anonymous, Eggs, joyofbaking.com, 2010.*
(Continued)

*Primary Examiner* — Rosanne Kosson
(74) *Attorney, Agent, or Firm* — Thorpe North & Western, LLP; David W. Osborne

(57) ABSTRACT

A detoxification system can include an effective amount of a probiotic component and a fiber component in combination with a circulation enhancing component, a high-protein meal replacement component, or both. The detoxification system increases urinary heavy metal excretion, decreases a fecal zonulin level, decreases a fecal calprotectin level, decreases a serum lipopolysaccharide binding protein (LBP) level, increases at least one of a salivary nitrite level and a (Continued)

serum arginine level, or a combination thereof in a subject as compared to a baseline level prior to administration of the detoxification system in an effective dosing regimen.

18 Claims, 19 Drawing Sheets

(51) Int. Cl.

| | | |
|---|---|---|
| A23L 33/105 | (2016.01) | |
| A23L 33/135 | (2016.01) | |
| A23L 33/21 | (2016.01) | |
| A61K 31/198 | (2006.01) | |
| A61K 31/375 | (2006.01) | |
| A61K 31/409 | (2006.01) | |
| A61K 31/4415 | (2006.01) | |
| A61K 31/51 | (2006.01) | |
| A61K 31/593 | (2006.01) | |
| A61K 31/702 | (2006.01) | |
| A61K 31/717 | (2006.01) | |
| A61K 31/733 | (2006.01) | |
| A61K 33/30 | (2006.01) | |
| A61K 35/742 | (2015.01) | |
| A61K 35/745 | (2015.01) | |
| A61K 35/747 | (2015.01) | |
| A61K 36/28 | (2006.01) | |
| A61K 36/63 | (2006.01) | |
| A61K 36/82 | (2006.01) | |
| A61K 36/87 | (2006.01) | |
| A61K 35/00 | (2006.01) | |
| A61K 45/06 | (2006.01) | |

(52) U.S. Cl.
CPC ............... *A23L 33/21* (2016.08); *A23L 33/30* (2016.08); *A61K 31/198* (2013.01); *A61K 31/375* (2013.01); *A61K 31/409* (2013.01); *A61K 31/4415* (2013.01); *A61K 31/51* (2013.01); *A61K 31/593* (2013.01); *A61K 31/702* (2013.01); *A61K 31/717* (2013.01); *A61K 31/733* (2013.01); *A61K 33/30* (2013.01); *A61K 35/745* (2013.01); *A61K 35/747* (2013.01); *A61K 36/28* (2013.01); *A61K 36/63* (2013.01); *A61K 36/82* (2013.01); *A61K 36/87* (2013.01); *A61K 2035/115* (2013.01); *A61K 45/06* (2013.01)

(56) References Cited

U.S. PATENT DOCUMENTS

| | | | |
|---|---|---|---|
| 2004/0161422 | A1 | 8/2004 | Ranganathan |
| 2011/0212224 | A1* | 9/2011 | Cruz Serrano ....... A23L 33/135 426/62 |
| 2016/0324904 | A1* | 11/2016 | Saito ..................... A61K 36/06 |
| 2017/0020948 | A1 | 1/2017 | Tripp et al. |
| 2017/0127701 | A1* | 5/2017 | Cohen .................. A61K 36/899 |

FOREIGN PATENT DOCUMENTS

| | | | | |
|---|---|---|---|---|
| EP | | 2135614 A1 * | 12/2009 | ........... A61K 31/721 |
| WO | WO 2015/158836 | A1 | 10/2015 | |
| WO | WO 2015/175536 | A1 | 11/2015 | |
| WO | WO 2017/155898 | A1 | 9/2017 | |

OTHER PUBLICATIONS

PCT Application No. PCT/US2018/059285 Filing date Nov. 5, 2018, Matthew L. Tripp International Search Report Mailing date May 15, 2019, 14 Pages.

* cited by examiner

Values are medians ± 95% confidence interval (N=38)

METHODS AND COMPOSITIONS TO ENHANCE METABOLIC DETOXIFICATION SYSTEMS

RELATED APPLICATION DATA

This application claims the benefit of U.S. Provisional Application No. 62/581,567 filed on Nov. 3, 2017, which is incorporated herein by reference.

BACKGROUND

Implementation of detoxification programs for much of the population remains challenging and largely unsubstantiated. Individuals suffer from a lack of information regarding the safety, tolerance, and acceptability of both lifestyle medicine programs and nutritional detoxification programs. The consensus remains that supplementation is not possible to further activate the body's systems to eliminate internal or environmental toxins in normal subjects or those with compromised intestinal functioning.

BRIEF DESCRIPTION OF THE DRAWINGS

Features and advantages of the technology will be apparent from the detailed description that follows, and which taken in conjunction with the accompanying figures, together illustrate technology embodiments. It is understood that the figures merely depict exemplary embodiments and are, therefore, not to be considered limiting in scope.

DETAILED DESCRIPTION

Figure 1:
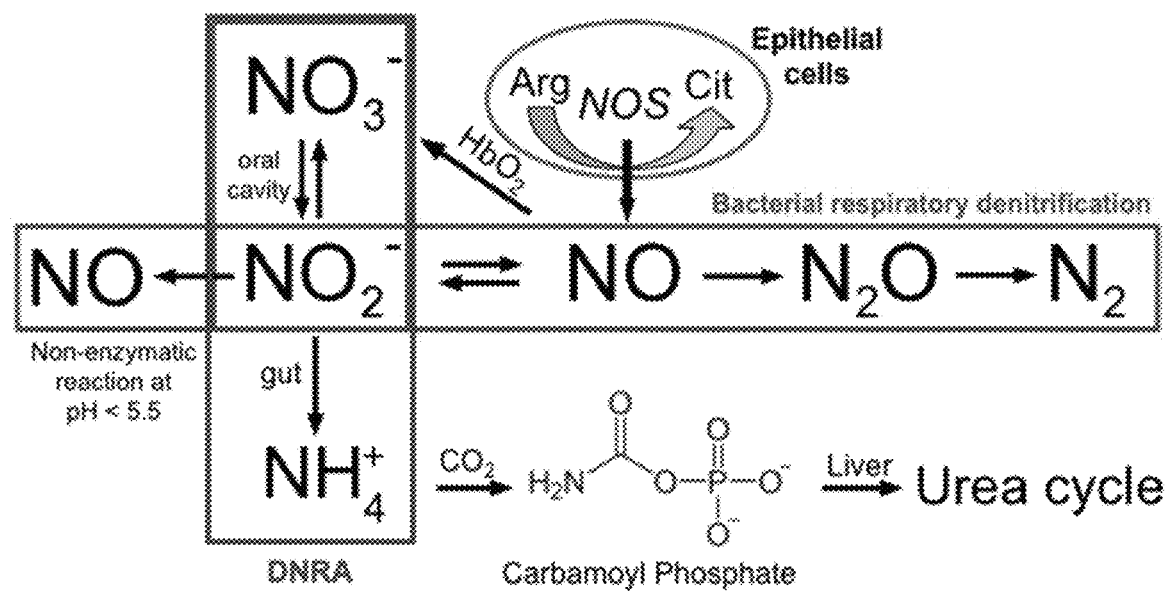
FIG. 1 is a graphic depiction of the nitrogen pathways in the human gut.

Before technology embodiments are disclosed and described, it is to be understood that no limitation to the particular structures, process steps, or materials disclosed herein is intended, but also includes equivalents thereof as would be recognized by those ordinarily skilled in the relevant arts. It should also be understood that terminology employed herein is used to describe particular examples only and is not intended to be limiting. The same reference numerals in different drawings represent the same element. Numbers provided in flow charts and processes are provided for clarity in illustrating steps and operations and do not necessarily indicate a particular order or sequence. Unless defined otherwise, all technical and scientific terms used herein have the same meaning as commonly understood by one of ordinary skill in the art to which this disclosure belongs. In the specification and the appended claims, the singular forms include plural referents and vice versa unless the context clearly dictates otherwise.

As used in this written description, the singular forms "a," "an," and "the" specifically also include express support for plural referents, unless the content clearly dictates otherwise. For example, "an excipient" provides support for one or more excipients.

The term "about" as used herein refers to a degree of deviation. It means approximately, in the region of, roughly, or around. When the term "about" is used in conjunction with a numerical value or range, it modifies that value or range by extending the boundaries a little above and below the numerical values set forth, for example 1, 2, 3, 4, or 5 numerical units above or below. It is understood that support in this specification for numerical values or other parameters used in connection with the term "about" is also provided for the exact numerical value or parameter itself as though "about" were not used.

Concentrations, amounts, and other numerical data may be expressed or presented herein in a range format. It is to be understood that such a range format is used merely for convenience and brevity and thus should be interpreted flexibly to include not only the numerical values explicitly recited as the limits or endpoints of the range, but also to include all the individual numerical values and/or subranges encompassed within that range as if each numerical value (including fractions) and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 2.6, 3, 3.8, and 4 and sub-ranges such as from 1-3, from 2-4, and from 3-5, etc., as well as 1, 2, 3, 4, and 5, individually.

As used herein, "comprises," "comprising," "containing" and "having" and the like can have the meaning ascribed to them in U.S. Patent law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law. "Consisting essentially of" or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the composition's nature or characteristics would be permissible if present under the "consisting essentially of" language, even though not expressly recited in a list of items following such terminology. When using an open ended term in the written description, like "comprising" or "including," it is understood that direct support should be afforded also to "consisting essentially of" language as well as "consisting of" language as if stated explicitly and vice versa.

As used herein, "detoxification" refers to the positive modification of absorption, distribution, metabolism or elimination processes to attenuate the adverse action of any biological or chemical entity that may adversely affect gut integrity, antioxidant status, immune functioning, neurological systems, or cellular signaling.

As used herein "balanced bowel function" or "gut integrity" or "gut patency" refers to the maintenance of cell-to-cell contact in the intestinal epithelium.

As used herein a "concentrate" refers to dried powder derived from a component that does not include the use of any solvents during the concentration process.

As used herein "cardiometabolic-associated pathologies" or "cardiometabolic risk factors" refers to any disease or condition that increases the risk of those pathologies associated with cardiovascular dysfunction. This can result from a combination of decreasing the localized production of NO and increasing myeloperoxidase activity at the same site. Non-limiting examples of such diseases or conditions include without limitation, angina, arterial plaque buildup, deep vein thrombosis, dementia, diabetes (types, 1, 2 and 3), diabetic foot disorders, elevated glucose, insulin or HOMA score, elevated hs-CRP (levels greater than 1.0 pmol/L), elevated myeloperoxidase (levels greater than 350 pmol/L), endothelial dysfunction, erectile dysfunction, fibrinogen levels greater than 370 pmol/L, HDL modification, heart attack, heart failure, pre-hypertension (blood pressure (BP) is about 120-139/about 80-89) or hypertension (BP≥about 140/90), lipoprotein-associated phospholipase A2 (LpPLA2 levels greater than 200 pmol/L), macular degeneration, monocyte-mediated arterial plaque formation, oxidation of LDL, periodontal disease, peripheral arterial disease, platelet stickiness, portal hypertension, pregnancy/pre-eclampsia, pulmonary hypertension, renal failure, serum low density lipoprotein (LDL) greater than 150 mg/dL, serum triglycerides greater than 150 mg/dL, sleep apnea, smooth muscle cell proliferation, stroke, and vasculitis.

The term "dosage unit" is understood to mean a unitary, i.e. a single dose which is capable of being administered to a subject or patient, and that may be readily handled and packed, remaining as a physically and chemically stable unit dose comprising either the active ingredient as such or a mixture of it with solid or liquid pharmaceutical vehicle materials. Dosages can be, but are not limited to, oral, nasal, enteral, parenteral, transdermal, transmucosal, rectal, ophthalmic, vaginal, etc.

The term "extract" refers to those substances prepared using a solvent, e.g., ethanol, water, steam, superheated water, methanol, hexane, chloroform liquid, liquid $CO_2$, liquid $N_2$, propane, supercritical $CO_2$, the like, or any combination thereof. Extracts, as used herein, can refer to an extract in a liquid form, or can refer to a product obtained from further processing of the liquid form, such as a dried powder or other solid form. Extracts may take many forms including but not limited to: solid, liquid, particulate, chopped, distillate, etc. and may be performed by any number of procedures or protocols, such as chopping, grinding, pulverizing, boiling, steaming, soaking, steeping, infusing, applying a gas, etc., and may employ any suitable reagents, such as water, alcohol, steam, or other organic materials. Extracts typically have a given purity percentage and can be relatively to highly pure. In some embodiments, extracts can be phytoextracts made from specific parts of a source, such as the skin, pulp, leaves, flowers, fruits of a plant etc., or can be made from the whole source. In some aspects an extract may include one or more active fractions or active agents. In some extracts, maltodextrin can be added as a carrier. In some aspects, the purity of an extract can be controlled by, or be a function of the extraction process or protocol.

As used herein, "formulation" and "composition" can be used interchangeably and refer to a combination of at least two ingredients. In some embodiments, at least one ingredient may be an active agent or otherwise have properties that exert physiologic activity when administered to a subject.

As used herein, "increased or decreased concentration, secretion or biosynthesis," means an appreciable or measurable increase or decrease in amount (e.g. by at least 2%, 3%, 5%, etc.), concentration, rate of secretion or amount of biosynthesis of the referent compound.

As used herein, "linear effect" or "dose-response" refers to a linear increase or decrease in secretion or biosynthesis resulting from all concentrations of the interacting material over a dose-response curve. For example, inhibition at low concentrations followed by a failure of inhibition or increased secretion at higher concentrations represents a lack of a linear inhibitory effect.

As used herein, "more effective," "more effectively," and the like is used to describe relative biological responses elicited by compounds or formulations wherein the response elicited by one formulation is greater per unit of time (e.g. more rapidly) or per unit dose (e.g. mg/kg body weight).

As used herein, the term "program supplements" refers to a combination of nutritional or dietary supplemental ingredients assembled in an amount and variety sufficient to effectively provide the nutritional and caloric values added to a nutritionally sound, caloric restricted diet. In one example the meal replacement formulation can be designed to provide a minimum of about 180 calories, 5 g fat, 16 g carbohydrate, 3 to 5 g fiber and 20 g protein per serving as well as other optional compounds such as ascorbic acid, biotin, *Chlorella/Chlorella vulgaris*, chromium nicotinate, copper citrate, D-calcium pantothenate, cyanocobalamin, flax seed/*Linum usitatissimum*, folic acid, fructooligosaccharide (fiber), magnesium oxide, manganese citrate, maltodextrin, medium chain triglycerides, natural vanilla flavor, niacinamide, potassium citrate potassium iodide, riboflavin, sugar cane (*Saccharum officinarum*), sodium molybdate dihydrate, sodium selenate (selenium), soy protein isolate, *stevia* leaf extract/*Stevia rebaudiana*, thiamin HCl, tricalcium phosphate, vitamin a palmitate, vitamin D3, xanthan gum, zinc citrate, cellulose gum, guar gum, pyridoxine hydrochloride, salt, vitamin E tocopherol, etc.

As used herein, "pharmaceutically acceptable" refers generally to materials which are suitable for administration to a subject in connection with an active agent or ingredient. For example, a "pharmaceutically acceptable carrier" can be any substance or material that can be suitably combined with an active agent to provide a composition or formulation suitable for administration to a subject. Excipients, diluents, and other ingredients used in or used to prepare a formulation or composition for administration to a subject can be used with such term.

As used herein, "physical activity equivalent to at least 5,000 steps per day" refers to any physical activity performed by an individual that burns a number of calories that is approximately equivalent to a number of calories burned if that same individual were to walk at least 5,000 steps in one 24 hour period. As a general example, such an amount may be a minimum of 250 calories. Examples of physical activity can include without limitation, jogging, dancing, cleaning, lifting weights, swimming, biking, hiking, climbing stairs, aerobic exercise, etc.

As used herein the term "primary therapeutic agent" designates the presence of a therapeutic agent in a composition at an amount greater than the total combined amount of the extracts providing a combined or synergistic effect in the composition.

The term "prevent" and its variants refer to prophylaxis against a particular undesirable physiological condition. The prophylaxis may be partial or complete. Partial prophylaxis may result in the delayed onset of a physiological condition. The person skilled in the art will recognize the desirability of delaying onset of a physiological condition, and will know to administer the compositions of the invention to subjects who are at risk for certain physiological conditions in order to delay the onset of those conditions. For example, the person skilled in the art will recognize that obese subjects are at elevated risk for conditions such as diabetes and coronary artery disease. Thus, the person skilled in the art can administer compositions to increase insulin sensitivity in an obese subject, whereby the onset of diabetes mellitus or dyslipemia may be prevented entirely or delayed.

The term, "subject," "subjects," "subjects in need thereof," and "individuals" includes humans as well as non-human subjects. It will be understood that the subject to which a compound of the invention is administered need not suffer from a specific traumatic state. Indeed, the compounds of the invention may be administered prophylactically. The terms "subject," "subjects," "subjects in need thereof," and "individuals" can be used interchangeably herein.

As used herein, "substantial" or "substantially" when used in reference to a quantity or amount of a material, or a specific characteristic thereof, refers to an amount that is sufficient to provide an effect that the material or characteristic was intended to provide. The exact degree of deviation allowable may in some cases depend on the specific context. Similarly, "substantially free of" or the like refers to the lack of an identified element or agent in a composition. Particularly, elements that are identified as being "substantially free of" are either completely absent from the composition, or are included only in amounts which are small enough so as to have no measurable effect on the composition.

As used herein, the term "solvent" refers to a fluid of gaseous or liquid, including aqueous or organic, nature possessing the necessary characteristics to extract solid material from a plant product. Examples of solvents would include, but not limited to, water, steam, superheated water, methanol, ethanol, ethyl acetate, hexane, chloroform, liquid $CO_2$, liquid $N_2$, propane, or any combinations of such materials.

The phrase "effective amount," "therapeutically effective amount," or "therapeutically effective rate(s)" of an active ingredient refers to a non-toxic, but sufficient amount or delivery rates of the active ingredient, to achieve therapeutic results in treating a disease or condition for which the ingredient is being delivered. It is understood that various biological factors may affect the ability of a substance to perform its intended task. Therefore, an "effective amount," "therapeutically effective amount," or "therapeutically effective rate(s)" may be dependent in some instances on such biological factors. Further, while the achievement of therapeutic effects may be measured by a physician or other qualified medical personnel using evaluations known in the art, it is recognized that individual variation and response to treatments may make the achievement of therapeutic effects a subjective decision. The determination of a therapeutically effective amount or delivery rate is well within the ordinary skill in the art of pharmaceutical sciences and medicine.

As used herein, "therapeutically effective time window" means the time interval wherein administration of the compounds of the invention to the subject in need thereof reduces or eliminates the deleterious effects or symptoms. In a preferred embodiment, the compound of the invention is administered proximate to the deleterious effects or symptoms.

The terms "treat," "treating," or "treatment" as used herein, and as well understood in the art, mean an approach for obtaining beneficial or desired physiological results in a subject, including without limitation clinical results in a subject being treated, and can encompass therapeutic, palliative, and/or prophylactic uses. For example, beneficial or desired results can include, but are not limited to, alleviation or amelioration of one or more signs or symptoms of a condition, diminishment of extent of disease, stabilizing (i.e. not worsening) the state of a disease or condition, delaying or slowing of disease progression, amelioration or palliation of the disease state, diminishment of the reoccurrence of disease, and remission (whether partial or total), whether detectable or undetectable. As a specific example, where the physiological state is obesity, the term "treatment" can refer to reducing the body fat mass, improving the body mass, or improving the body fat ratio of a subject, for example. "Treat," "treating," and "treatment" can also mean prolonging survival as compared to expected survival if not receiving treatment and can be prophylactic. Such prophylactic treatment can also be referred to as prevention or prophylaxis of a disease or condition. The prophylaxis may be partial or complete. Partial prophylaxis may result in the delayed onset of a physiological condition. The person skilled in the art will recognize that treatment may, but need not always, include remission or cure.

As used herein, "administering" a compound, component, or agent to a subject refers to imparting the compound, component, or agent to the subject in a way that provides the subject with a positive physiologic or health benefit as a result of the administration. A number of specific administration routes are known, such as oral, enteral, transdermal, transmucosal, parenteral, intravenous, and injectable administration.

As used herein, "coadminster," "coadministration," and "coadministering," refer to administering two or more active agents, compounds, components, extracts, supplements, etc. in a way that allows the active agents, compounds, components, extracts, supplements, etc. to have a concomitant or overlapping physiological effect on a subject. As such, coadministration includes both administration of multiple agents to a subject at the same time or within a time relative to one another that allows the physiologic or in-vivo effect or result of each agent to take place in a simultaneous or overlapping manner.

As used herein, "compounds" may be identified either by their chemical structure, chemical name, or common name. When the chemical structure, chemical name, or common name conflict, the chemical structure is determinative of the identity of the compound. The compounds described herein may contain one or more chiral centers and/or double bonds and therefore, may exist as stereoisomers, such as double-bond isomers (i.e., geometric isomers), enantiomers or diastereomers. Accordingly, the chemical structures depicted herein encompass all possible enantiomers and stereoisomers of the illustrated or identified compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds may also exist in several tautomeric forms including the enol form, the keto form and mixtures thereof. Accordingly, the chemical structures encompass all possible tautomeric forms of the illustrated or identified compounds. The compounds described also encompass isotopically labeled compounds where one or more atoms have an atomic mass different from the atomic mass conventionally found in nature. Examples of isotopes that may be incorporated into the compounds of the invention include, but are not limited to, $^2H$, $^3H$, $^{13}C$, $^{14}C$, $^{15}N$, $^{18}O$, $^{17}O$, etc. Compounds may exist in un-solvated forms as well as solvated forms, including hydrated forms and as N-oxides. In general, compounds may be hydrated, solvated or N-oxides. Certain compounds may exist in multiple crystalline or amorphous forms. Also contemplated are congeners, analogs, hydrolysis products, metabolites and precursor or prodrugs of the compound. In general, all physical forms are equivalent for the uses contemplated herein and are intended to be within the scope of the present disclosure.

Comparative terms such as "more effectively," "greater than," "improved," "enhanced," and like terms can be used to state a result achieved or property present in a formulation or process that has a measurably better or more positive outcome than the thing to which comparison is made. For example, when referring to an improved health of a subject the comparison may be made to the health of the subject prior to engaging in the activity which improved the health of the subject.

Reference is made hereinafter in detail to specific technology embodiments. While the technology will be described in conjunction such embodiments, it will be understood that it is not intended to limit the technology disclosed. On the contrary, it is intended to cover alternatives, modifications, and equivalents as may be included within the spirit and scope of the technology as defined by the appended claims. In the following description, numerous specific details are set forth in order to provide a thorough understanding of the present technology. The present technology may be practiced without some or all of these specific details. In some instances, well-known process operations have not been described in detail, in order not to unnecessarily obscure the present technology.

Implementation of detoxification programs for much of the population remains challenging and largely unsubstantiated. Individuals suffer from a lack of information regarding the safety, tolerance, and acceptability of both lifestyle medicine programs and nutritional detoxification programs. The consensus remains that supplementation is not possible to further detoxification in normal subjects or those with compromised intestinal functioning.

However, as described herein, a certain detoxification systems including, for example, an effective ratio of specific probiotic strains, nitrates, and fiber can be useful in metabolic syndrome prevention and treatment through enhanced detoxification. The gut microbiome is the main target and player in the interactions occurring between probiotics, prebiotics, nitrates and polyphenols. Growth and metabolism of gut microflora can be managed with specific prebiotics and polyphenols. Without wishing to be limited to theory, it is believed that probiotic bacteria may operate on three levels of host functionality to enhance gut microbioma and extra intestinal functions namely, (i) interfering with the growth of pathogenic bacteria in the lumen of the gastro intestinal tract (GIT) via changing the microenvironment through production of secondary metabolites such as nitrite, lactic, acetate, proprionate and butyrate; (ii) strengthening the epithelial gut lining's barrier function and mucosal immunity as well as mucus production; and (iii) effect the systemic immune system, as well as other cell and organ systems such as the liver.

With this in mind, the present disclosure describes detoxification systems including a probiotic component, a nitric-oxide generating component, and a fiber component that can cooperate to provide improved detoxification outcomes. For example, the present detoxification systems can increase urinary heavy metal excretion, decrease fecal zonulin levels, decrease serum lipopolysaccharide binding protein (LBP), increase at least one of salivary nitrite levels and serum arginine levels, or a combination thereof.

In further detail, metallothioneins (MTs) belong to the group of intracellular cysteine-rich, metal-binding proteins that have been found in bacteria, plants, invertebrates, and vertebrates. These proteins were discovered in 1957 as cadmium-binding proteins isolated from horse kidney. Since their discovery, these low molecular weight cysteine-rich proteins have been continuously studied in all aspects, including physical, chemical and biochemical properties. Mammalian MTs may contain approximately 61-68 amino acids, and among them approximately 25%-35% (e.g. about 20) are typically cysteines. These unique proteins are involved in diverse intracellular functions, including their role in the detoxification of heavy metals and in the maintaining of essential metal ion homeostasis, which is due to their high affinity for these metals. For mammals, MTs bind zinc, but with excess copper or cadmium, zinc can be easily replaced by these metals. Cells that contain excessive amounts of MTs are resistant to cadmium toxicity and cell lines that cannot synthesize MTs are sensitive to cadmium. Based on structural models, it can be assumed that the MT molecule is composed of two binding domains, a and 13, which are composed of cysteine clusters. Covalent binding of metal atoms involves sulfhydryl cysteine residues. The N-terminal part of the peptide is designated as β-domain and has three binding sites for divalent ions, and the C-terminal part (the α-domain) has the ability to bind four divalent metal ions. With this in mind, the detoxification systems described herein can increase serum MT levels and can increase urinary heavy metal excretion. In some specific examples, the detoxification systems described herein can increase serum MT levels by at least about 5%, at least about 10%, or at least about 15% as compared to a baseline serum MT level prior to using a detoxification system as described herein in an effective dosage regimen. Additionally, in some specific examples, the detoxification systems described herein can increase urinary heavy metal excretion by at least about 5%, at least about 10%, at least about 20%, at least about 30%, at least about 40%, or at least about 50% as compared to a baseline urinary heavy metal excretion level prior to using a detoxification system as described herein in an effective dosage regimen.

Additionally, the structural protein zonulin functions as the modulator of intestinal permeability. The intestinal wall—the single-cell-thick layer of epithelial cells lining the inside of the gut—is the largest barrier between the human body and the outside world. Maintaining control of this barrier is important for regulation of the immune system and protection against pathogens. There are two routes from gut lumen to the bloodstream—across the enterocyte brush border via transporters (the "transcellular" route, as in absorption of most nutrients), or through gaps between the cells (the "paracellular" route, through which ions, water-soluble molecules, and occasional microbes passively flow). The paracellular route is finely controlled by intricate protein "gates" called tight junctions. These dynamic structures open and close in tune with dietary state, physical activity, hormonal and neural signals, and inflammatory mediators.

A key physiological and reversible modulator of tight junctions is zonulin, a protein produced in the mucosa that directly controls intestinal permeability. In response to stimuli such as luminal bacteria or food-derived triggers (e.g., gluten), zonulin is released into the lumen and binds to receptors on the epithelial cells' apical surface, activating signaling pathways that cause disassembly of the tight junction. This zonulin-driven opening of the paracellular pathway may be a defense mechanism, as it allows secretion of water into the lumen, flushing out microorganisms to prevent their colonization.

Prolonged zonulin upregulation from environmental triggers can lead to increased intestinal permeability and an uncontrolled flow of intestinal antigens into the submucosa, which can cause chronic inflammation and autoimmune disorders in genetically susceptible individuals—both in the gut (e.g., celiac disease, inflammatory bowel disease) and throughout the body (e.g., type 1 diabetes, rheumatoid arthritis, multiple sclerosis).

Intestinal hyperpermeability is also associated with chronic conditions of unclear etiology, such as irritable bowel syndrome (IBS). Translocation of bacteria (or bacterial products such as lipopolysaccharide) into the circulation plays a causative role in many metabolic conditions, such as fatty liver disease, type 2 diabetes, and cardiovascular disease, by promoting inflammation in the liver. Gut-derived bacterial products and cytokine cascades resulting from gut barrier breach have also been linked to neuroinflammation and the development of depression.

Clinical studies have shown that zonulin levels correlate strongly with the "gold standard" lactulose-mannitol test for intestinal permeability. Zonulin is thus an excellent biomarker of impaired gut barrier function. There may be advantages to measuring zonulin in stool vs. serum when assessing intestinal permeability, as serum zonulin also reflects its release from other tissues such as lung and brain.

Increased intestinal permeability has been linked to many chronic conditions, and activation of the zonulin pathway has been implicated in the pathogenesis of celiac disease and metabolic disorders. For example, zonulin upregulation in patients with celiac disease reflects the increased intestinal permeability that is a key feature of the disorder. Elevated zonulin in patients with dermatitis herpetiformis who have only minimal mucosal damage suggests an early role for abnormal zonulin-dependent intestinal permeability in the pathogenesis of gluten-dependent diseases. Even in non-celiac patients, gluten-derived gliadin has been shown to stimulate zonulin release and increase intestinal permeability. Elevated zonulin levels have been demonstrated in a substantial proportion of patients with type 1 diabetes several years before disease onset. This is consistent with a causative role of intestinal hyperpermeability in autoimmune diabetes and a predictive role of zonulin in disease onset and progression. Preclinical studies also support a mechanistic role of zonulin-mediated hyperpermeability in the pathogenesis of type 1 diabetes. Compromised gut barrier function and increased zonulin levels have been associated with insulin resistance (independent of body mass index), and metabolic conditions such as type 2 diabetes. For example, increased intestinal permeability renders the patient more susceptible to luminal antigens, which may trigger the release of anti-inflammatory cytokines and auto-immune reactions against the beta-cells of the pancreas. Further, a link between zonulin level, insulin resistance, visceral adiposity, and severity of menstrual disorders in women with polycystic ovary syndrome suggests that zonulin may aid in risk stratification for cardiometabolic disease in such patients.

Diagnostic cut points have been established for fecal zonulin concentration on the basis of estimated disease prevalence and represent the 80th (85.1 ng/g) and 60th (65 ng/g) percentiles:
 (i) Zonulin values ≤64.9 ng/g suggest healthy tight junctions maintaining appropriate levels of intestinal permeability;
 (ii) Zonulin values from 65 to 85 ng/g may represent mild upregulation in zonulin-mediated intestinal permeability; and
 (iii) Zonulin values ≥85.1 ng/g are higher than the 80th percentile, consistent with increased intestinal permeability.

With this in mind, the present detoxification systems can help to decrease fecal zonulin levels of a subject. For example, in some cases, the present detoxification systems can help decrease fecal zonulin levels of a subject by about 10% or more, about 20% or more, about 30% or more, about 40% or more, or about 50% or more as compared to a baseline fecal zonulin level prior to using a detoxification system as described herein in an effective dosage regimen.

Calprotectin is a small calcium- and zinc-binding protein that derives mainly from neutrophils, constituting 60% of the cytosolic protein. Active inflammation in the gut that induces neutrophil influx into the mucosa will eventually disrupt the mucosal architecture, allowing neutrophils (with their cytosolic calprotectin) to leak into the intestinal lumen and be excreted with the feces. Fecal calprotectin correlates with the severity of intestinal inflammation, and is a sensitive biomarker of inflammatory bowel disease (IBD). Measurement of fecal calprotectin represents a reliable, accurate, and noninvasive method of detecting mucosal inflammation in the GI tract.

With this in mind, the present detoxification systems and methods can help to decrease fecal calprotectin levels of a subject. For example, in some cases, the present detoxification systems and methods can help decrease fecal calprotectin levels of a subject by at least about 15%, at least about 20%, at least about 25%, at least about 30%, at least about 35%, or at least about 40% as compared to a baseline fecal calprotectin level prior to using a detoxification system or method as described herein in an effective dosage regimen.

Further, lipopolysaccharide binding protein (LBP) is involved in the acute-phase immunologic response to gram-negative bacterial infections. Gram-negative bacteria contain a glycolipid, lipopolysaccharide (LPS), on their outer cell wall. Together with bactericidal permeability-increasing protein (BPI), the LPB binds LPS and interacts with the CD14 receptor, probably playing a role in regulating LPS-dependent monocyte responses. Studies in mice suggest that the encoded protein is necessary for the rapid acute-phase response to LPS but not for the clearance of LPS from circulation. LBP has a concentration-dependent dual role in the pathogenesis of gram-negative sepsis: low concentrations of LBP enhance the LPS-induced activation of mononuclear cells (MNC), whereas the acute-phase rise in LBP concentrations inhibits LPS-induced cellular stimulation. Among LBP, hs-CRP, TNF-alpha, and IL-6, plasma LBP has the greatest diagnostic accuracy for insulin resistance. With this in mind, the detoxification systems described herein can decrease serum LBP levels in a subject. In some examples, a detoxification system or method as described herein can decrease serum LBP levels by at least about 1%, at least about 2%, at least about 3%, at least about 4%, or at least about 5% relative to a baseline LBP level prior to using a detoxification system as described herein in an effective dosage regimen.

Nitric oxide (NO) is a free radical, actively produced in the human body, and is the smallest signaling molecule known. NO exerts crucial roles in vascular and neuronal signal transduction, smooth muscle contractility, bioenergetics, improved gut barrier function, platelet adhesion and aggregation, immunity, and cell death regulation (Table 1). Defective control of NO levels can result in pathologies such as hypertension, cardiovascular dysfunction, neurodegeneration, arthritis, asthma, and septic shock.

TABLE 1

Examples of Established Functions of Nitric Oxide in Physiological Systems

| System | Function |
| --- | --- |
| Cardiovascular | Controls vascular tone. |
| | Relaxes vascular smooth muscles and reduces blood pressure. |
| | Dilates vessels and relieves the pain of angina. |
| | Inhibits the aggregation of platelets within the vessels and prevents thrombotic event. |
| Nervous | Acts as a neurotransmitter, including in the autonomic nervous system. |
| | Increases cerebral blood flow and oxygenation to the brain. |
| | Important mediator in penile erection during sexual arousal. |
| Pulmonary | Dilates pulmonary vessels. |
| | Benefits Adult Respiratory Distress Syndrome, pulmonary hypertension and Chronic Obstructive Airway Disease. |
| | Produced in abnormal amounts in inflammatory lung conditions. |
| | Concentration of NO in exhaled air can be taken as a marker of airway inflammation. |
| Gastrointestinal | Regulates the relaxation of smooth muscles. |
| | Controls peristalsis and the function of sphincters. |
| | Improve gut barrier function |
| | Gut microbiome supports increasing NO3 production |
| Renal | Increases blood flow to the kidney due to its vasodilatory effect. |
| | Increases the glomerular filtration rate and the production of urine. |
| Immune | Modulates T cell-mediated immune response. |

One of the prevailing theories is that pulses of NO in the picomolar to low nanomolar range are by and large physiological; whereas, cell persistence at micromolar concentrations may become pathological. Evidence is growing that the dark side of NO resides in its concentration levels, the production of peroxynitrite and other reactive oxygen and reactive nitrogen species, the type of biomolecule reacting with the NO, and, when present, the cell bioenergetic changes that can be induced, which can strongly contribute to physiological or pathological outcomes (e.g. interactions with myeloperoxidase).

As depicted in FIG. 1, amino acid L-arginine, dietary nitrate ($NO_3$), and nitrite ($NO_2$) can serve as sources for production of NO(x) (a diverse group of metabolites NO, nitrosothiols, and nitroalkenes). The NO(x) production occurs via nitric oxide synthase enzymes (NOS), ultraviolet light exposure to skin, and mammalian nitrate/nitrite reductases in tissues, respectively. NO(x) are responsible for the hypotensive, anti-platelet, and cytoprotective effects of dietary nitrates and nitrites.

Enzymatically, NO is produced by nitric oxide synthases which utilize L-arginine and molecular oxygen as substrates and require the cofactors of reduced nicotinamide-adeninedinucleotide phosphate (NADPH), flavin adenine dinucleotide (FAD), flavin mononucleotide (FMN), and (6R-)5,6,7,8-tetrahydrobiopterin (BH(4)). All of the isoforms of NOS can bind calmodulin and contain heme.

Neuronal NOS (nNOS, NOS I) is constitutively expressed in central and peripheral neurons, as well as, some other cell types. Its functions include synaptic plasticity in the central nervous system (CNS), central regulation of blood pressure, smooth muscle relaxation, and vasodilatation via peripheral nitrergic nerves. These nitrergic nerves are of particular important in the relaxation of corpus cavernosum and penile erection. Phosphodiesterase 5 inhibitors (sildenafil, vardenafil, and tadalafil) require at least a residual nNOS activity for their action.

Inducible NOS (iNOS, NOS II) is involved in immune responses, binds calmodulin and produces NO as an immune defense mechanism. Inducible NOS can be expressed in many cell types and can be expressed in response to lipopolysaccharide, cytokines, or other agents. iNOS generates large amounts of NO that have cytostatic effects on parasitic target cells. iNOS contributes to the pathophysiology of inflammatory diseases and septic shock.

Endothelial NOS (eNOS, NOS III) is mainly expressed in endothelial cells. It keeps blood vessels dilated, controls blood pressure, and has numerous vasoprotective and anti-atherosclerotic effects. Pharmacologically, vascular oxidative stress can be reduced and eNOS functionality restored with renin- and angiotensin-converting enzyme-inhibitors, with angiotensin receptor blockers, and with statins. eNOS inhibitors, such as asymmetric-dimethyl-L-arginine (ADMA), inhibit NO synthesis in vivo by competing with L-arginine at the active site of eNOS. In addition, eNOS possesses the ability to be "uncoupled" to produce superoxide anion instead of NO. Reduced NO bioavailability may play an essential role in cardiovascular pathologies and metabolic diseases. Cardiovascular risk factors can lead to oxidative stress, eNOS uncoupling, and endothelial dysfunction in the vasculature.

Figure 2:
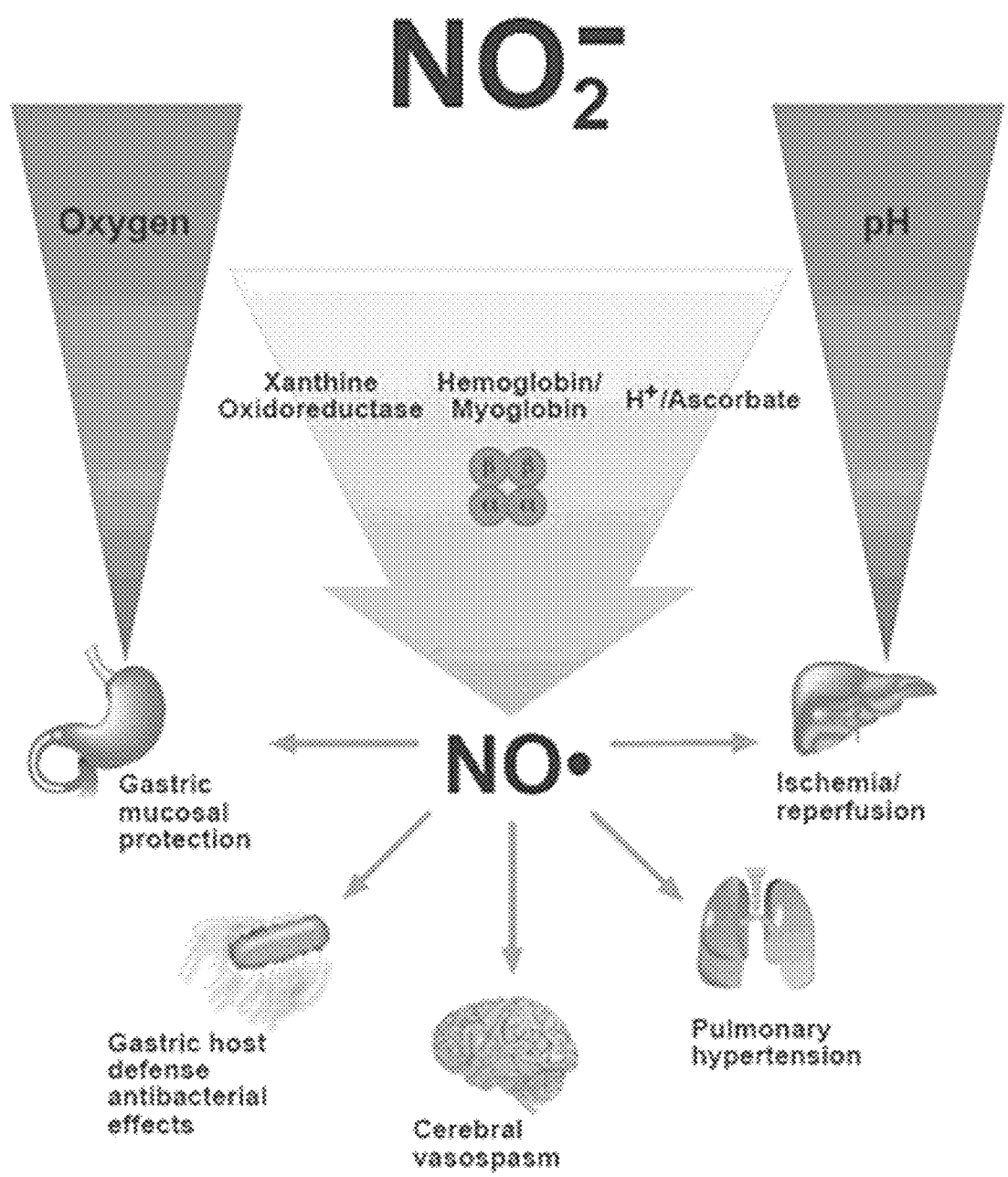
FIG. 2 schematically displays the dual enzymatic and non-enzymatic pathways for nitric oxide production from nitrite.

Endogenous synthesis is an important contributor to human's overall exposure of nitrate and ultimately production of NO. Once produced through NOS, NO has a half-life of approximately 1 second, can be quickly oxidized to nitrite and nitrate, or react with thiols or amines. Approximately 50% of the circulating levels of plasma nitrite reflect endogenous NO production, while steady-state levels of plasma nitrite and nitrate are determined primarily by diet. The bioavailability of dietary $NO_3$ can be 100%. Following absorption, $NO_3$ may be reduced by facultative anaerobic bacteria on the dorsal surface of the tongue to nitrite, which can be chemically (low pH) and enzymatically (xanthine oxidoreductase, myoglobin, cytochrome P450, complexes of the mitochondrial electron transport chain) further reduced to NO. See FIG. 2. How NO is released from $NO_3$, and $NO_2$ at specific sites when needed, however, is not completely understood.

Vegetables are the most abundant source of nitrates in the human diet; approximately 80% of dietary nitrates are derived from vegetable consumption; sources of nitrites include vegetables, fruit, and processed meats (See Table 2). Vegetables contribute more than 85% of the daily dietary intake of nitrate. The standard US diet contains 50 mg to 120 mg nitrate while the standard Mediterranean Diet provides an estimated 400 mg nitrate per day.

TABLE 2

Nitrate Content of Selected Vegetables in Mediterranean Diet

| Vegetable | Nitrate Content [mg/kg] |
|---|---|
| Beans | 400 |
| Beets | 1500 |
| Carrots | 170 |
| Eggplant | 460 |
| Fennel | 2,000 |
| Potatoes | 120 |
| Zucchini | 810 |

Orally consumed $NO_3$ reaches a peak plasma concentration in approximately 1 hour; the half-life of plasma $NO_3$ is approximately 5-8 hours. Because $NO_3$ is a relatively small anion and is not protein bound, its pharmacokinetics and half-life suggest that it is reabsorbed in the renal tubules. $NO_3$ is excreted in the urine directly or after conversion to urea. Clearance of $NO_3$ from blood to urine is approximately 20 mL/min in adults indicating considerable renal tubular reabsorption of the ion. It is estimated that 96% of the filtered $NO_2$ and $NO_3$ is reabsorbed in the renal tubules.

Physiological concentrations of L-arginine in healthy individuals are sufficient to saturate eNOS, which occurs at approximately 3 μmol arginine/L. Supplementation, however, may be beneficial in special conditions such as malnutrition, excessive ammonia production, burns, infections, peritoneal dialysis, rapid growth, urea synthesis disorders, and/or sepsis. Since serum concentrations of L-arginine are normally in excess with respect to eNOS formation of NO, it is likely that there is no change in plasma concentration of $NO_2$ and $NO_3$ as a result of L-arginine supplementation. Acute L-arginine supplementation of 6 g does not increase plasma concentration of NOx over 120 minutes in healthy individuals with normal plasma concentrations of ADMA. Despite this, L-Arginine deficiency syndromes in humans involve dysregulation of system functions described in Table 1. Further, L-arginine or L-citrulline supplementation may help treat individuals with atherosclerosis risk factors, such as hypercholesterolemia, hypertension, all forms of diabetes mellitus, kidney failure, hyperhomocysteinemia, smoking, and aging (See Table 1), all of which are conditions that are associated with reduced NO biosynthesis through eNOS.

In humans and other animals, dysregulation of NO is involved in the etiology of many diseases, such as Alzheimer's disease, angina, asthma, general congestive disorders, Crohn's disease, deep vein thrombosis, dementia, diabetes (types, 1, 2 and 3), diabetic foot disorders, diminished exercise capacity, endothelial dysfunction, endotoxemia, erectile dysfunction, fibromyalgia glomerulonephritis, heart attack, heart failure, hypertension, immune deficiency, inflammatory bowel disease, leaky gut, macular degeneration, monocyte-mediated arterial plaque formation, motor dysfunction, multiple sclerosis, obesity, oxidation of LDL, periodontal disease, peripheral arterial disease, platelet stickiness, portal hypertension, pregnancy/pre-eclampsia, premature ejaculation, pulmonary hypertension, Raynaud's disease, renal failure, sleep apnea, smooth muscle cell proliferation, stroke, vasculitis and diseases associated with skin such as slow wound healing, wrinkles, and premature signs of aging.

With this in mind, the detoxification methods and systems described herein can help decrease NO dysregulation. For example, in some cases, the detoxification systems described herein can increase salivary nitrites by at least about 5%, at about least 10%, at least about 20%, at least about 30%, or at least about 40% as compared to a baseline salivary nitrite level prior to using the detoxification systems described herein in an effective dosing regimen. In some additional examples, the detoxification systems described herein can increase serum arginine levels by at least about 5%, at least about 10%, at least about 15%, or at least about 20% as compared to a baseline serum arginine level prior to using the detoxification systems described herein in an effective dosing regimen. In still additional examples, the detoxification systems described herein can increase the amount of serum arginine relative to the amount of serum ADMA (i.e. the serum arginine/ADMA ratio) by at least about 5%, at least about 10%, at least about 15%, at least about 20%, or at least about 25% as compared to a baseline serum arginine/ADMA ratio prior to using the detoxification systems described herein in an effective dosing regimen.

In further detail, the detoxification systems described herein can include a probiotic component and a fiber component in combination with a circulation enhancing component, a high-protein meal replacement component having a minimum of about 15 grams of protein, or both. As described above, the detoxification systems can increase urinary heavy metal excretion, decrease a fecal zonulin level, decrease a fecal calprotectin level, decrease a serum lipopolysaccharide binding protein (LBP) level, increase at least one of a salivary nitrite level and a serum arginine level, or a combination thereof in a subject as compared to a baseline level prior to administration of the detoxification system.

Generally, the probiotic component can include at least one of *Bacillus* spp., *Lactobacillus* spp., *Bifidobacterium* spp., and *Streptococcus* spp. However, other probiotics can also be used in addition to or as alternatives to those listed herein. In some examples, the probiotic component can include *Bacillus* spp. Non-limiting examples of *Bacillus* spp. that can be suitable for use as a probiotic can include *B. subtilus*, *B. coagulans*, the like, or a combination thereof. In some specific examples, the probiotic component includes *B. coagulans*. In some additional examples, the probiotic component can include *Lactobacillus* spp. Non-limiting examples of *Lactobacillus* spp. that can be suitable for use as a probiotic can include *L. rhamnosus, L. acidophilus, L. brevis, L. bulgaricus, L. plantarum, L. casei, L. salivarius*, the like, or a combination thereof. In some further examples, the probiotic component can include *Bifidobacterium* spp. Non-limiting examples of *Bifidobacterium* spp. that can be suitable for use as a probiotic can include *B. bifidum, B. infantis, B. longum*, the like, or a combination thereof. In still further examples, the probiotic component can include *Streptococcus* spp. Non-limiting examples of *Streptococcus* spp. that can be suitable for use as a probiotic can include *Streptococcus thermophilus* or the like.

In one example, the probiotic component can include at least one of *Bacillus coagulans, Lactobacillus* spp., *Bifidobacterium* spp., and *Streptococcus* spp. In another example, the probiotic component can be a blend. It is noted that, in some examples, the probiotic component can include one or more individual supplements of individual genera or species. In other examples, a single composition can include a plurality of genera or species. In one example, the probiotic can comprise living cultures. In another example, the probiotic can comprise freeze-dried cultures.

The probiotic component can provide a variety of different daily doses. In one example, the probiotic component can provide a daily dose of about 2 billion to about 40 billion colony forming units (cfu) of probiotic. In another example, the probiotic component can provide a daily dose of about 1.5 billion to about 25 billion cfu of probiotic. In yet another example, the probiotic component can provide a daily dose of about 3.5 billion to about 45 billion cfu of probiotic. In a further example, the probiotic component can provide a daily dose of about 2 billion to about 9 billion cfu of probiotic. In still further examples, the probiotic component can provide a daily dose of about 3 billion cfu of probiotic. Consuming a probiotic can have additional benefits to the subject. In some instances, a daily dose of probiotics can regulate the microbiome of the users intestinal and digestive systems. In another example, consuming probiotics can help aid in the elimination of toxins from the body. In yet other examples, consuming probiotics can support healthy immune functioning.

In some examples, the probiotic component can include a variety of additional ingredients in addition to probiotic strains. For example, in some cases, the probiotic component can further include inulin, fructooligosaccharide, prebiotic fibers, natural or artificial flavorings, the like, or a combination thereof. In some examples, the probiotic component can be formulated as a solid oral dosage form, such as a capsule, gel capsule, or the like. In some examples, the probiotic component can be formulated as a powder, a gel, a confectionery (e.g. chewable gummy, for example), the like, or a combination thereof.

The fiber component can also include a variety of ingredients. Typically, the fiber component can include one or more of psyllium hulls, apple fruit fiber, flax seeds, guar gum, and acacia gum. However, the fiber component can also include a variety of additional ingredients. For example, the fiber component can include apple extract, grape extract, green tea extract, olive extract, and/or other suitable extracts.

Where the fiber component includes an apple extract, the apple extract can be or include an extract of *Malus domestica, Malus sieversii, Malus sylvestris, Malus pumila*, or a combination thereof. In one example, the apple extract can be an extract of *Malus pumila*. In another example, the apple extract can be an extract of *Malus domestica* and *Malus pumila*. In some embodiments, the apple extract can include an extract of the skin, flesh/fruit (exocarp, mesocarp, and/or endocarp), seed, stalk, stem, leaf, or a combination thereof. In one example, the apple extract can be or include an apple skin extract and an apple fruit extract. In some examples, the apple extract can be or include an extract of immature apples. The extraction solvent for the apple extract can typically be or include water, ethanol, or a mixture thereof.

Where the fiber component includes a grape extract, the grape extract can be or include an extract of *Vitis vinifera, Vitis labrusca, Vitis riparia, Vitis rotundifolia, Vitis rupestris, Vitis aestivalis, Vitis mustangensis*, the like, or a combination thereof. In one example, the grape extract can be or include an extract of *Vitis vinifera*. In some examples, the grape extract can include an extract of any or all parts of the grape, including but not limited to the skin, flesh/fruit, seed, vascular bundles, vine, leaves, the like, or a combination thereof. In one example, the grape extract can be or include a grape seed extract. In another example, the grape extract can be or include a grape skin extract. In yet another example, the grape extract can be or include a grape seed extract and a grape skin extract. In some examples, the grape extract can be or include a grape polyphenol extract. For example, in some cases, the grape polyphenol extract can include from about 75 wt % to about 95 wt % phenolics on a dry weight basis. In other embodiments, the grape polyphenol extract can include from about 80 wt % to about 97 wt % phenolics on a dry weight basis. The extraction solvent for the grape extract can typically be or include ethanol, water, or a mixture thereof.

Where the fiber component includes a green tea extract, the green tea extract can be or include an extract of *Camellia sinensis*. In some embodiments, the green tea extract can include any or all parts of the green tea including but not limited to the leaf, seed, stem, flower, the like, or a combination thereof. In one example, the green tea extract can be or include a green tea leaf extract. The extract solvent for the green tea extract can typically be or include water, ethanol, ethyl acetate, or a mixture thereof.

Where the fiber component includes an olive extract, the olive extract can typically include an extract of a subspecies of *Olea europea*, such as *europea, cuspidiata, guanchica, cerasiformis, maroccana, laperrinei, cerasiformis*, or a combination thereof. In some examples, the olive extract can include any or all parts of the olive including but not limited to the leaf, seed, pulp, fruit, stem, or a combination thereof. In one example, the olive extract can be or include an olive leaf extract. The extraction solvent can typically be or include water, ethanol, or a mixture thereof. In some specific examples, the extraction solvent can be a mixture of ethanol and water.

In some embodiments, the plant or herb to extract ratio in the fiber component can range from about 1 to about 10. In other examples, the raw plant or herb to extract ratio can be from about 2 to about 5, from about 4 to about 7, or from about 8 to about 10. In one example, at least one of the extracts in the fiber component can be present in a different amount than one or more of the other extracts. In another example, the extracts can all be present in the fiber component in the same amount.

As non-limiting examples, in some cases, one extract can be present in the fiber component at a weight ratio of from about 0.02 times to about 50 times the amount of another extract. In some specific example, the apple extract can be present in the formulation at a weight ratio of from about 0.02 times to about 50 times (including about 0.02 to about 1, about 1 to about 50, etc.) the amount of a grape extract, a green tea extract, an olive extract, and/or other suitable extract. In another specific example, an apple extract can be present in the fiber component at a weight ratio of from about 0.04 times to about 25 times (including about 0.04 to about 1, about 1 to about 25, etc.) the amount of a grape extract, green tea extract, olive extract, and/or other suitable extract. In another example, an apple extract can be present in the fiber component at a weight ratio of from about 0.1 times to about 10 times (including about 0.1 to about 1, about 1 to about 10, etc.) the amount of a grape extract, green tea extract, olive extract, and/or other suitable extract. In still another specific example, an apple extract can be present in the fiber component at a weight ratio of from about 0.2 times to about 5 times (including about 0.2 to about 1, about 1 to about 5, etc.) the amount of a grape extract, a green tea extract, an olive extract, and/or other suitable extract. In one specific example, an apple extract can be present in the fiber component at a weight ratio of about 1 to about 1 relative to individual amounts of a grape extract, a green tea extract, an olive extract, and/or other suitable extract. It is further noted that while these ranges are specifically described with reference to an apple extract, the same weight ratio ranges can be applied to any extract included in the fiber component relative to another extract. By way of example, where the fiber component includes a grape extract, the grape extract can similarly be present in the fiber component at a weight ratio of from about 0.02 to about 50, from about 0.04 to about 25, from about 0.1 to about 10, from about 0.2 to about 5, or from about 1 to about 1 relative to an apple extract, or other suitable extract included in the fiber component. The same can be true for any extract included in the fiber component.

In some specific examples, the fiber component can include an apple extract, a grape extract, a green tea extract, and an olive extract. Where this is the case, the amount of apple extract to grape extract to green tea extract to olive extract can be 1-25:1-25:1-25:1-25, respectively, or other suitable ratio as described herein. As a further example, the apple, grape, green tea, and olive extracts can be present in the fiber component at a weight ratio of about 1:1:1:1. In another example, the apple, grape, green tea, and olive extracts can be present in the fiber component at a weight ratio of about 6:1:3:1.

In some additional examples, the fiber component can further include turmeric extract. In one example, the turmeric extract can be obtained from *Curcuma longa*. In some embodiments, the turmeric extract can include an extract of the root, the rhizome, or a combination thereof. In another example, the turmeric extract can be obtained from a turmeric powder. In an additional example, the turmeric powder can have from about 1% to about 10% curcuminoids, from about 3% to about 5% curcuminoids, from about 2% to about 8% curcuminoids, or from about 4% to about 12% curcuminoids.

In yet additional examples, the fiber component can additionally include one or more of inulin, turmeric root, red beet root, cabbage leaf, chlorophyllin (e.g. sodium copper chlorophyllin, for example), broccoli flowers, L-glutamine, a fruit concentrate, zinc, rosemary leaf, tomato fruit, apple extract, grape extract, green tea extract, and olive extract. In another example, the fiber component can include one or more of vitamin B12, vitamin B6, and folic acid. In one example, the fiber component can further include one or more individual vitamins and/or minerals at the recommended daily values established by the Food and Drug Administration (FDA). In some specific examples, the fiber component can further include chlorophyllin. In some additional examples, the fiber component can further include L-glutamine. In some further examples, the fiber component can also include a fruit concentrate. In still additional examples, the fiber component can further include zinc.

In some examples, the detoxification systems described herein can include a circulation enhancing component. The circulation enhancing component can include one or more ingredients suitable to increase or improve cardiovascular circulation in a subject. As non-limiting examples, the circulation enhancing component can include an angiotensin-converting enzyme (ACE) inhibitor, a phosphodiesterase type 5 (PDE5) inhibitor, myeloperoxidase inhibitors, red beet root, L-arginine, L-glutamine, L-citrulline, inorganic nitrates, watermelon extract, apple extract, olive extract, green tea extract, grape extract, the like, or a combination thereof. Thus, the circulation enhancing component can include a variety of ingredients. In some examples, the circulation enhancing component can be a nitric oxide (NO)-generating component. In some specific examples, the circulation enhancing component can include one or more of red beet root, L-arginine, L-glutamine, L-citrulline, and grape extract. It is noted that red beet root, L-arginine, L-glutamine, L-citrulline, grape extract, and the like can aid in the natural production of NO and the associated benefits derived therefrom, as described elsewhere herein.

In one example, the circulation enhancing component can include grape extract. The grape extract can include an extract of *Vitis vinifera, Vitis labrusca, Vitis riparia, Vitis rotundifolia, Vitis rupestris, Vitis aestivalis, Vitis mustangensis*, the like, or a combination thereof. In one example, the grape extract can be or include an extract of *Vitis vinifera*. In some examples, the grape extract can include an extract of any or all parts of the grape, including but not limited to the skin, flesh/fruit, seed, vascular bundles, vine, leaves, the like, or a combination thereof. In one example, the grape extract can be or include a grape seed extract. In another example, the grape extract can be or include a grape skin extract. In yet another example, the grape extract can be or include a grape seed extract and a grape skin extract. In some examples, the grape extract can be or include a grape polyphenol extract. For example, in some cases, the grape polyphenol extract can include from about 75 wt % to about 95 wt % phenolics on a dry weight basis. In other embodiments, the grape polyphenol extract can include from about 80 wt % to about 97 wt % phenolics on a dry weight basis. The extraction solvent for the grape extract can typically be or include ethanol, water, or a mixture thereof.

In one example, the circulation enhancing component can include an apple extract, green tea extract, olive extract, the like, or a combination thereof. Where the circulation enhancing component includes an apple extract, the apple extract can be or include an extract of *Malus domestica, Malus sieversii, Malus sylvestris, Malus pumila*, or a combination thereof. In one example, the apple extract can be an extract of *Malus pumila*. In another example, the apple extract can be an extract of *Malus domestica* and *Malus pumila*. In some embodiments, the apple extract can include an extract of the skin, flesh/fruit (exocarp, mesocarp, and/or endocarp), seed, stalk, stem, leaf, or a combination thereof. In one example, the apple extract can be or include an apple skin extract and an apple fruit extract. In some examples, the apple extract can be or include an extract of immature apples. The extraction solvent for the apple extract can typically be or include water, ethanol, or a mixture thereof.

In one example, the circulation enhancing component can include a green tea extract. Where this is the case, in some examples, the green tea extract can be or include an extract of *Camellia sinensis*. In some embodiments, the green tea extract can include any or all parts of the green tea including but not limited to the leaf, seed, stem, flower, the like, or a combination thereof. In one example, the green tea extract can be or include a green tea leaf extract. The extract solvent for the green tea extract can typically be or include water, ethanol, ethyl acetate, or a mixture thereof.

In one example, the circulation enhancing component can include an olive extract. Where this is the case, the olive extract can include an extract of a subspecies of *Olea europea*, such as *europea, cuspidiata, guanchica, cerasiformis, maroccana, laperrinei, cerasiformis*, or a combination thereof. In some examples, the olive extract can include any or all parts of the olive including but not limited to the leaf, seed, pulp, fruit, stem, or a combination thereof. In one example, the olive extract can be or include an olive leaf extract. The extraction solvent can typically be or include water, ethanol, or a mixture thereof. In some specific examples, the extraction solvent can be a mixture of ethanol and water.

In some embodiments, the plant or herb to extract ratio (e.g. wt % ratio) in the circulation enhancing component can range from about 1 to about 10. In other examples, the raw plant or herb to extract ratio can be from about 2 to about 5, from about 4 to about 7, or from about 8 to about 10. In one example, at least one of the extracts in the circulation enhancing component can be present in a different amount than one or more of the other extracts. In another example, the extracts can all be present in the circulation enhancing component in the same amount.

As non-limiting examples, in some cases, one extract can be present in the circulation enhancing component at a weight ratio of from about 0.02 times to about 50 times the amount of another extract. In some specific examples, a grape extract, for example, can be present in the formulation at a weight ratio of from about 0.02 times to about 50 times (including about 0.02 to about 1, about 1 to about 50, etc.) the amount of an apple extract, a green tea extract, an olive extract, and/or other suitable extract. In another specific example, the grape extract can be present in the circulation enhancing component at a weight ratio of from about 0.04 times to about 25 times (including about 0.04 to about 1, about 1 to about 25, etc.) the amount of an apple extract, green tea extract, olive extract, and/or other suitable extract. In another example, the grape extract can be present in the circulation enhancing component at a weight ratio of from about 0.1 times to about 10 times (including about 0.1 to about 1, about 1 to about 10, etc.) the amount of an apple extract, green tea extract, olive extract, and/or other suitable extract. In still another specific example, the grape extract can be present in the circulation enhancing component at a weight ratio of from about 0.2 times to about 5 times (including about 0.2 to about 1, about 1 to about 5, etc.) the amount of an apple extract, a green tea extract, an olive extract, and/or other suitable extract. In one specific example, the grape extract can be present in the circulation enhancing component at a weight ratio of about 1 to about 1 relative to individual amounts of an apple extract, a green tea extract, an olive extract, and/or other suitable extract. It is further noted that while these ranges are specifically described with reference to the grape extract, the same weight ratio ranges can be applied to any extract included herein relative to another extract. By way of example, where the circulation enhancing component includes an apple extract, the apple extract can similarly be present in the circulation enhancing component at a weight ratio of from about 0.02 to about 50, from about 0.04 to about 25, from about 0.1 to about 10, from about 0.2 to about 5, or from about 1 to about 1 relative to a grape extract, a green tea extract, an olive extract, or other suitable extract included in the circulation enhancing component. The same can be true for any extract included in the circulation enhancing component.

In some specific examples, the circulation enhancing component can include a grape extract, an apple extract, a green tea extract, and an olive extract. Where this is the case, the amount of grape extract to apple extract to green tea extract to olive extract can be 1-25:1-25:1-25:1-25, respectively, or other suitable ratio as described herein. As a further example, the grape, apple, green tea, and olive extracts can be present in the circulation enhancing component at a weight ratio of about 1:1:1:1. In another example, the grape, apple, green tea, and olive extracts can be present in the circulation enhancing component at a weight ratio of about 6:1:3:1.

In some additional examples, the circulation enhancing component can further include one or more of stevia leaf extract, watermelon whole fruit extract, vitamin C, citric acid, vitamin B12, folic acid, inulin, magnesium oxide, malic acid, a natural or artificial flavoring (e.g. natural citrus sweetener, citrus blend natural flavor, natural cherry flavor, lemonade flavor, the like, or a combination thereof), vitamin B6, silicon dioxide, thiamin (B1), D-ribose, vitamin D3, apple extract, green tea extract, and olive extract. Watermelon whole fruit extract can be derived from *Garcinia mangosana*. The fruit extract can be derived from any part of the fruit including but not limited to the pulp, the rind, the seeds, or a combination thereof. In one embodiment, the watermelon extract can be prepared to have a standardized amount of citruline. In some examples, the antioxidant phytochemical composition can further include blueberry extract/concentrate, capsicum extract, turmeric extract, mangosteen extract, bergamot extract, or a combination thereof. In one embodiment, a mangosteen extract can be derived solely from the rind of the fruit. In one embodiment, the bergamot extract can be derived from *Citrus bergamia* Risso.

The circulation enhancing component can have a variety of mechanisms of action in addition to inducing detoxification. In one embodiment, the circulation enhancing component can quench free radicals. In another embodiment, the circulation enhancing component can modulate peroxynitrate formation. In one example, the circulation enhancing component can modulate stress signaling enzymes such as matrix metalloproteinases and myeloperoxidase. In yet another example, the circulation enhancing component can be used for modulating oxidative stress in a mammal in need thereof. In some embodiments, the circulation enhancing component can synergistically provide circulation enhancing, antioxidant support for gut microbiota and inhibition of peroxynitrite formation and gut inflammation.

The circulation enhancing component can be administered at any effective dose. In one example, the circulation enhancing component can be present in the therapeutic system in an amount of from about 5 grams (g) to about 30 g. In another example, the circulation enhancing component can be present in the therapeutic system in an amount of from about 7 g to about 30 g. In yet another example, the circulation enhancing component can be present in the therapeutic system in an amount of from about 8 g to about 50 g. In one example, the circulation enhancing component can be present in the therapeutic system in an amount of about 25 g.

In some additional examples, the detoxification systems can further include a high-protein meal replacement component. Typically, the high-protein meal replacement component can include at least 15 grams of protein. In other examples, the high-protein meal replacement component can include at least 20 grams of protein. In still other examples, the high-protein meal replacement component can include at least 40 grams of protein. In one example, the meal replacement component can be or include a protein supplement. In another example, the meal replacement component can include a weight loss shake. In one example, the meal replacement component can include about 20 g protein, from about 3 g to about 5 g fat, about 16 g carbohydrate, about 2 g of phytosterols, and about 180 calories. In another example, the meal replacement component can include a daily dose of about 20 g protein to about 60 g protein, from about 3 g to about 15 g fat, from about 32 g to about 96 g carbohydrate, from about 2 g to about 4 g of phytosterols, and from about 180 to about 540 calories. In yet another example, the meal replacement component can include a daily dose of about 40 g protein, from about 6 g to about 10 g fat, about 32 g carbohydrate, about 4 g of phytosterols, and about 360 calories.

In some examples, the detoxification systems described herein can include additional ingredients. In some examples, the additional ingredients can be part of one or more components (e.g. an herbal component, a vitamin/mineral component, an antioxidant component, etc.) of the detoxification systems in addition to the probiotic component, the fiber component, the circulation enhancing component, and/or the high-protein meal replacement component. In some other examples, the additional ingredients can be included in one or more of the probiotic component, the circulation enhancing component, and the fiber component when these components are separate supplements. In still additional examples, the probiotic component, the circulation enhancing component, and the fiber component can be formulated into a single supplement and the additional ingredients can be further included in the single supplement. Non-limiting examples of additional ingredients can include iron, docosahexaenoic acid (DHA), eicosapentaenoic acid (EPA), calcium, niacin, folic acid, biotin, panthothenic acid, phosphorus, iodine, magnesium, zinc, selenium, copper, manganese, chromium, potassium, inositol, p-Aminobenzoic acid (PABA), choline, bitartrate, lycopene, lutein, antioxidants, dandelion root, alfalfa aerial parts, asparagus stem, broccoli flowers, cabbage leaf, hesperidin bioflavonoid extract, lemon bioflavonoid extract, rutin, rose hips extract, chlorophyll, kelp leaf, kelp stem, cranberry fruit, mangosteen fruit, carrot root, spinach leaf, spinach stem, tomato fruit, acai berry, pomegranate fruit extract, leucine, lysine, citrulline, valine, isoluecine, phenyalanine, threonine, arginine, methionine, tyrosine, cysteine, the like, or a combination thereof. Additional ingredients can also include those ingredients listed elsewhere herein. For example, while psyllium hulls are specifically mentioned with reference to the fiber component, psyllium hulls can also be included in the probiotic component, the circulation enhancing component, the high-protein meal replacement component, and/or other additional component(s) of the detoxification systems. Psyllium hulls is only one example used for illustration and any ingredients listed herein, or the like, can also be used in one or more of the probiotic component, the fiber component, the circulation enhancing component, the high-protein meal replacement component, and any additional components of the detoxification systems, unless otherwise specified. It is also noted that, in some examples, one or more of the ingredients listed herein can be expressly excluded from one or more of the probiotic component, the fiber component, the circulation enhancing component, the high-protein meal replacement component, and any additional components of the detoxification systems. For example, in some cases, psyllium hulls can be expressly excluded from the probiotic component, the fiber component, the circulation enhancing component, the high-protein meal replacement component, and/or any additional component(s) of the detoxification systems. Again, psyllium hulls are listed as one non-limiting example for the sake of illustration, and the same extends to other ingredients listed herein.

The amount of additional ingredients/components per unit serving are a matter of design and will depend upon the total number of unit servings of each of the probiotic component, the fiber component, the circulation enhancing component, and/or the high-protein meal replacement component administered to the subject. The total amount of additional ingredients/components can also depend, in part, upon the health of the subject. In some embodiments, the additional ingredients/components in the detoxification systems can be chosen such that the additional ingredients/components do not exceed the FDA recommended daily values for the additional ingredients/components. In some examples, the amount of other ingredients/components can be a fraction or multiplier of the Reference Daily Allowance (RDA) or Reference Daily Intake (RDI) amounts.

In some aspects, the probiotic component, the fiber component, the circulation enhancing component, the high-protein meal replacement component, and/or other ingredients/components can further include a pharmaceutically acceptable excipient. In one example, pharmaceutically acceptable excipients can include coatings, isotonic and absorption delaying agents, binders, adhesives, lubricants, disintegrants, coloring agents, flavoring agents, sweetening agents, absorbents, detergents, emulsifying agents, diluents, the like, and combinations thereof. While the type of pharmaceutically acceptable carrier/vehicle employed in generating the compositions of the invention will vary depending upon the mode of administration of the composition, generally pharmaceutically acceptable carriers are physiologically inert and non-toxic.

In some embodiments, the probiotic component, the fiber component, the circulation enhancing component, the high-protein meal replacement component, and/or other ingredients/components can further include flavorings, coloring agents, spices, nuts, the like, or a combination thereof. Flavorings can be in the form of flavored extracts, volatile oils, chocolate flavorings (e.g., non-caffeinated cocoa or chocolate, chocolate substitutes such as carob), peanut butter flavoring, cookie crumbs, crisp rice, vanilla, or any commercially available flavoring. In some examples, flavorings can be protected with mixed tocopherols. Examples of useful flavorings can include, but are not limited to, pure anise extract, imitation banana extract, imitation cherry extract, chocolate extract, pure lemon extract, pure orange extract, pure peppermint extract, imitation pineapple extract, imitation rum extract, imitation strawberry extract, imitation or pure vanilla extract; volatile oils, such as balm oil, bay oil, bergamot oil, cedarwood oil, cherry oil, walnut oil, cinnamon oil, clove oil, or peppermint oil; peanut butter, chocolate flavoring, vanilla cookie crumb, butterscotch, toffee, the like, or a combination thereof. In a specific example, the probiotic component, the fiber component, the circulation enhancing component, the high-protein meal replacement component, and/or other ingredients/components contain berry or other fruit flavor. In some further examples, the probiotic component, the fiber component, the circulation enhancing component, the high-protein meal replacement component, and/or other ingredients/components may further be coated, for example with a yogurt coating if it is as a bar, or other suitable coating.

Emulsifiers may be added for stability of the final product. Examples of suitable emulsifiers include, but are not limited to, lecithin (e.g., from egg or soy), or mono- and di-glycerides. Other emulsifiers are readily apparent to the skilled artisan and selection of suitable emulsifier(s) will depend, in part, upon the formulation and final product.

Preservatives may also be added to the probiotic component, the fiber component, the circulation enhancing component, the high-protein meal replacement component, and/or other ingredients/components to extend product shelf life. Non-limiting examples can include potassium sorbate, sodium sorbate, potassium benzoate, sodium benzoate, calcium disodium EDTA, the like, or a combination thereof.

Additionally, one or more of the probiotic component, the fiber component, the circulation enhancing component, the high-protein meal replacement component, and/or other ingredients/components can further include natural or artificial sweeteners, e.g., glucose, sucrose, fructose, saccharides, cyclamates, aspartame, sucralose, aspartame, acesulfame K, sorbitol, the like, or a combination thereof.

In one example, the probiotic component, the fiber component, the circulation enhancing component, the high-protein meal replacement component, and/or other ingredients/components are in a single formulation. In another example, the probiotic component, the fiber component, the circulation enhancing component, the high-protein meal replacement component, and/or other ingredients/components are in multiple separate formulations.

In some examples, two or more of the probiotic component, the fiber component, the circulation enhancing component, the high-protein meal replacement component, and/or other ingredients/components can be combined into a single formulation. In other examples, the probiotic component, the fiber component, the circulation enhancing component, the high-protein meal replacement component, and/or other ingredients/components can be formulated into separate formulations. When combined in a single formulation, the formulation can include any combination of any or all of the probiotic component, the fiber component, the circulation enhancing component, the high-protein meal replacement component, and/or other ingredients/components. In some embodiments, two or more, or all, of the probiotic component, the fiber component, the circulation enhancing component, the high-protein meal replacement component, and/or other ingredients/components are in a co-formulation. A co-formulation is a single unit containing all active ingredients. A co-formulation can be a single powder in a container, all actives in a pill, softgel or capsule, etc. In some examples, the probiotic component, the fiber component, the circulation enhancing component, the high-protein meal replacement component, and/or other ingredients/components are in the form of multiple formulations in a kit or system.

When administered in an individual engaging in a caloric restricted diet and daily physical activity, the detoxification systems disclosed herein can stimulate weight loss in excess of the weight loss resulting from the caloric restricted diet and daily physical activity. In one example, the detoxification systems can stimulate weight loss of at least 3%. In some examples, the detoxification system can provide the subject with an amount of weight loss that is greater than an amount attributable to the additive effect of eating the caloric restricted diet and engaging in the daily physical activity.

The present disclosure also describes a detoxification method that accelerates detoxification in a subject. The method can include administering a probiotic component as described herein to the subject and administering a fiber component as described herein to the subject in combination with administering a circulation enhancing component as described herein to the subject, administering a high-protein meal replacement component to the subject, or both. The detoxification method can increase urinary heavy metal excretion, decrease a fecal zonulin level, decrease a fecal calprotectin level, decrease a serum lipopolysaccharide binding protein (LBP) level, increase at least one of a salivary nitrite level and a serum arginine level, or a combination thereof in the subject as compared to a baseline level prior to administration of the probiotic component and the fiber component in combination with administration of the circulation enhancing component, the high-protein meal replacement component, or both in an effective dosing regimen.

The probiotic component can be administered to the subject in a variety of doses. In some examples the administered daily dose can be any of the daily doses discussed elsewhere herein. In one example, the probiotic component can be administered to the subject at a daily dose of about 2 billion cfu to about 40 billion cfu. In another example, the probiotic component can be administered to the subject at a daily dose of about 3 billion cfu. The quantity of daily doses of the probiotic component can vary based on the formulation. In one example, the probiotic component can be administered to the subject once a day. In another example, the probiotic component can be administered to the subject twice a day. In some embodiments, the probiotic component can be administered to the subject three times a day.

The fiber component can be administered in a variety of amounts. In some examples, the fiber component can be administered in an amount to provide a daily dose of soluble fiber of from about 5 g to about 40 g. In other examples, the fiber component can be administered in an amount to provide a daily dose of soluble fiber of from about 7 g to about 30 g. In still other examples, the fiber component can be administered in an amount to provide a daily dose of soluble fiber of from about 8 g to about 20 g. In some examples, the fiber component can be administered once per day. In other examples, the fiber component can be administered twice daily. In still other examples, the fiber component can be administered three times daily. In some further examples, the fiber component can be administered in the morning. In other examples, the fiber component can be administered in the evening.

The administration of the circulation enhancing component can vary. The administered daily dose can be any of the daily doses discussed elsewhere herein. In one example, the circulation enhancing component can be administered to the subject in a daily amount a daily dose ranging from about 5 g to about 25 g. In another example, the circulation enhancing component can be administered to the subject at a daily dose ranging from about 7 g to about 30 g. In yet another example, the circulation enhancing component can be administered to the subject at a daily dose of about 25 g. The quantity of daily doses of the circulation enhancing component can vary based on the formulation. In one example, the circulation enhancing component can be administered to the subject once a day. In one example, the circulation enhancing component can be administered in the morning. In another example, the circulation enhancing component can be administered in the evening. In another example, the circulation enhancing component can be administered to the subject twice a day.

In some embodiments, the detoxification methods can include replacing one or multiple meals with a meal replacement component. In one example, the meal replacement component can include a protein supplement. In another example, the meal replacement component can include a weight loss shake. In one example, the meal replacement component can include about 20 g protein, from about 3 g to about 5 g fat, about 16 g carbohydrate, about 2 g of phytosterols, and about 180 calories. In another example, the meal replacement component can include a daily dose of about 20 g protein to about 60 g protein, from about 3 g to about 15 g fat, from about 32 g to about 96 g carbohydrate, from about 2 g to about 4 g of phytosterols, and from about 180 to about 540 calories. In yet another example, the meal replacement component can include a daily dose of about 40 g protein, from about 6 g to about 10 g fat, about 32 g carbohydrate, about 4 g of phytosterols, and about 360 calories. This is approximately a meal replacement amount, but can also be considered a snack.

The probiotic component, the fiber component, the circulation enhancing component, the high-protein meal replacement component, and/or other ingredients/components can be administered in any suitable form. The probiotic component, the fiber component, the circulation enhancing component, the high-protein meal replacement component, and/or other ingredients/components can include those suitable for oral, enteral, inhalation, rectal, ophthalmic (including intravitreal or intracameral), nasal, topical (including buccal and sublingual), vaginal, or parenteral (including subcutaneous, intramuscular, intravenous, intradermal, and intratracheal) administration. In addition, the probiotic component, the fiber component, the circulation enhancing component, the high-protein meal replacement component, and/or other ingredients/components can be formulated as a depot preparation. Such long-acting compositions may be administered by implantation (e.g. subcutaneously, intra-abdominally, or intramuscularly) or by intramuscular injection. Thus, for example, the active ingredient(s) may be formulated with suitable polymeric or hydrophobic materials (for example, as an emulsion in a pharmaceutically acceptable oil), or an ion exchange resin.

In one example, the probiotic component, the fiber component, the circulation enhancing component, the high-protein meal replacement component, and/or other ingredients/components can be (an) oral formulation(s). In one example, the oral formulation can be in a capsule or tablet form. In another example, the oral formulation(s) can be in the form of one or more of a liquid (e.g. solution, suspension, emulsion, colloid, etc.), capsule, confectionery, powder, and a bar. In other examples an oral formulation can be formulated into a food or drink, and provided, for example, as a snack bar, a cereal, a drink, a gum, or in any other easily ingested form. In one embodiment, the nutritional supplement can be formulated into a nutritional beverage. Nutritional beverages can have consumer appeal, be easy to administer and incorporate into one's daily regimen. To manufacture the beverage, the ingredients are dried and made readily soluble in water. In some embodiments, the probiotic component, the fiber component, the circulation enhancing component, the high-protein meal replacement component, and/or other ingredients/components can be in a topical formulation. In some examples, the topical formulation can be a cream, lotion, or a patch. It will be recognized that one of ordinary skill in the art would be able to formulate the present composition into any of these convenient forms for oral or topical administration after a review of the present disclosure.

In some examples, the detoxification method can further include a caloric restricted diet with a minimum daily protein intake of about 3 ounces (oz.). Generally, the caloric restricted diet can include a total daily caloric intake of from about 1,250 calories to about 2,200 calories. In an additional example, the total daily caloric intake can be from about 1,250 calories to about 1,500 calories. In another example, the caloric restricted diet can comprise a total daily caloric intake from about 1,300 calories to about 1,450 calories. In yet another embodiment, the caloric restricted diet can comprise a total daily caloric intake of about 1,350 calories to about 1,800 calories. In a further embodiment, the caloric restricted diet can comprise a total daily caloric intake of about 1,400 calories to about 1700 calories.

In some embodiments, the caloric restricted diet can be a high phytonutrient and protein rich diet. In other embodiments, the caloric restricted diet can be a low fat diet. In some examples, the caloric restricted diet can include limiting intake of, or otherwise substantially eliminating, at least one of sugars, refined carbohydrates, and grains. In another example, the caloric restricted diet can include limiting at least two of sugars, refined carbohydrates, and grains. In yet another example, the caloric restricted diet can include limiting sugars, refined carbohydrates, and grains.

In some examples, the caloric restricted diet can include multiple small meals per day. In one example, the caloric restricted diet can include 5 meals per day plus snacks. In another example, the caloric restricted diet can include 6 meals per day plus snacks.

The subject's daily protein intake can also vary. In some embodiments, the caloric restricted diet can include a minimum daily protein intake of about 6 oz. In another embodiment, the caloric restricted diet can include a minimum daily protein intake of about 9 oz. In a further embodiment, the caloric restricted diet can include a minimum daily protein intake of about 12 oz. In some embodiments, the protein can be consumed in increments or servings of about 3 oz. In some embodiments, multiple 3 oz. servings can be given at each meal and/or snack, for example, two 3 oz. servings for a total of 6 oz. per meal. In some embodiments, the caloric restricted diet can include a minimum daily protein intake of about 6 oz. to about 80 oz. of protein.

In some embodiments, the caloric restricted diet can comprise a set amount of servings from different food groups. In one example, the caloric restricted diet can include a daily vegetable intake of about 3 cups to about 6 cups of vegetables, a daily minimum fresh greens intake of 5 ounces, and a daily minimum fluid intake of 48 fluid ounces. In one embodiment, the caloric restricted diet can include a daily vegetable intake of 4 servings, a daily minimum fresh greens intake of 7 ounces, and a daily minimum fluid intake of 64 ounces. In another embodiment, the caloric restricted diet further includes a single serving of fruit and/or legumes. In yet another embodiment, the caloric restricted diet can include a serving of dairy. In other embodiments, the caloric restricted diet can include a maximum of 5 total daily servings of oils and/or fats. Table 3 shows the different food groups and daily servings for one exemplary caloric restricted diet.

TABLE 3

Exemplary Caloric Restricted Diet

| Category | Total Daily Servings | Serving Size |
|---|---|---|
| Meal Protein | 3 | Palm sized |
| Snack Protein | 2 | ½ palm size |
| Vegetables | 6 | ½ cup to 1 cup |
| Fresh Greens | 5 ounces | Varies |
| Fruit | 1 | Varies |
| Legumes | 1 | ½ cup (can replace fruit) |
| Dairy | 1 | Varies (can replace one snack protein) |
| Oils/Fats | 5 | Varies |
| Beverages | At least 6-8 | 8 fluid ounces |

In some additional examples, the detoxification method can further include daily physical activity. In some examples, the daily physical activity can include the subject taking at least 5,000 steps per day or engaging in an activity that burns an equivalent amount of calories as the subject taking at least about 5,000 steps per day. In another example, the daily physical activity can include the subject engaging in an activity that burns an equivalent amount of calories as the subject taking at least about 7,500 steps per day. In yet another example, the daily physical activity can include the subject engaging in an activity that burns an equivalent amount of calories as the subject taking at least about 10,000 steps a day. Physical activities can include any suitable aerobic activity, resistance training, strength training, flexibility exercises, the like, or a combination thereof. The physical activity can be any activity that burns an equivalent amount of calories; whether it be walking, running, lifting weights, hiking, dancing, playing sports, or any other multitude of physical activities.

In one example, the subject can engage in physical activities or exercise activities that daily expend from about 115 calories to about 300 calories 5 days a week. In another example, the subject can engage in physical activities or exercise activities that daily expend from about 150 calories to about 500 calories at least 3 days a week. In yet another example, the subject can engage in physical activities or exercise activities that daily expend from about 325 calories to about 600 calories at least 3 days a week.

In some examples, the detoxification method can further include a cognitive behavioral program. The cognitive behavioral program can be any activity designed to change the cognitive processes of the subject with respect to dieting, health, and/or exercise. In one example, the cognitive behavioral program can include a weekly seminar on mindfulness and teaching visualization techniques for stress reduction, relaxation, mind-body connectivity, and combinations thereof.

The detoxification method can be performed for a minimum period of time. In one example, the method can be performed for a period of at least 1 week. In another example, the method can be performed for a period of at least 2 weeks. In another example, the method can be performed for a period of at least 4 weeks.

Where the detoxification method is performed for a minimum period of time of at least 1 week, at least 2 weeks, or at least 4 weeks, a number of beneficial physiological effects can be achieved. In some specific examples, where the detoxification method is performed for a minimum period of time of at least 1 week, at least 2 weeks, or at least 4 weeks, serum MT levels can increase by at least about 5%, at least about 10%, or at least about 15% as compared to a baseline serum MT level prior to using a detoxification system as described herein in an effective dosage regimen. Additionally, in some specific examples, where the detoxification method is performed for a minimum period of time of at least 1 week, at least 2 weeks, or at least 4 weeks, urinary heavy metal excretion can be increased by at least about 5%, at least about 10%, at least about 20%, at least about 30%, at least about 40%, or at least about 50% as compared to a baseline urinary heavy metal excretion level prior to using a detoxification system as described herein in an effective dosage regimen.

In some additional examples where the detoxification method is performed for a minimum period of time of at least 1 week, at least 2 weeks, or at least 4 weeks fecal zonulin levels of a subject can decrease to about 90% or below, about 80% or below, about 70% or below, about 60% or below, or about 50% or below a baseline fecal zonulin level prior to using a detoxification system as described herein in an effective dosage regimen. In still additional examples where the detoxification method is performed for a minimum period of time of at least 1 week, at least 2 weeks, or at least 4 weeks, fecal calprotectin levels of a subject can be decreased by at least about 15%, at least about 20%, at least about 25%, at least about 30%, at least about 35%, or at least about 40% as compared to a baseline fecal calprotectin level prior to using a detoxification system as described herein in an effective dosage regimen. In yet additional examples where the detoxification method is performed for a minimum period of time of at least 1 week, at least 2 weeks, or at least 4 weeks, serum LBP levels can be decreased by at least about 1%, at least about 2%, at least about 3%, at least about 4%, or at least about 5% relative to a baseline LBP level prior to using a detoxification system as described herein in an effective dosage regimen.

In further examples where the detoxification method is performed for a minimum period of time of at least 1 week, at least 2 weeks, or at least 4 weeks, salivary nitrates can be increased by at least about 5%, at least about 10%, at least about 20%, at least about 30%, or at least about 40% as compared to a baseline salivary nitrate level prior to using the detoxification systems described herein in an effective dosing regimen. In some additional examples where the detoxification method is performed for a minimum period of time of at least 1 week, at least 2 weeks, or at least 4 weeks, serum arginine levels can be increased by at least about 5%, at least about 10%, at least about 15%, or at least about 20% as compared to a baseline serum arginine level prior to using the detoxification systems described herein in an effective dosing regimen. In still additional examples where the detoxification method is performed for a minimum period of time of at least 1 week, at least 2 weeks, or at least 4 weeks, the amount of serum arginine relative to the amount of serum ADMA (i.e. the serum arginine/ADMA ratio) can be increased by at least about 5%, at least about 10%, at least about 15%, at least about 20%, or at least about 25% as compared to a baseline serum arginine/ADMA ratio prior to using the detoxification systems described herein in an effective dosing regimen.

Also presented herein is a detoxification method of improving the health of a subject eating a caloric restricted diet with a minimum daily protein intake of about 3 ounces (oz.) and engaging in daily physical activity equivalent to at least about 5,000 steps per day. The method can include co-administering a high-protein meal replacement formulation designed to deliver a minimum of about 15 grams protein, and a therapeutic system as described herein (e.g. a probiotic component as described herein, a circulation enhancing component as described herein, and a fiber component as described herein). It is noted that in some examples, the therapeutic system can include a high-protein meal replacement formulation. Where this is the case, the present method can include administering a therapeutic system as disclosed herein to a subject. Each of these components is described elsewhere herein and can be administered as described elsewhere herein.

The caloric restricted diet and moderate physical activity can be as discussed elsewhere herein. In one embodiment, the detoxification method of improving health of the subject can comprise the subject consuming a caloric restricted diet with a minimum daily protein intake of at least 9 oz. and engaging in daily physical activity equivalent to at least 5,000 steps per day.

The method of improving the health of a subject can have a variety of health benefits to the subject. The improvement of health in the subject can be measured as determined by the health of the subject prior to participating in the method.

The improvement in health can be an improvement in the overall subjective assessment of health as assesses by the Short Form (36) Health Survey including (i) general health, (ii) physical functioning, (iii) physical health, (iv) emotional problems, (v) energy/fatigue or vitality, (vi) pain, (vii) emotional well-being, and (viii) social functioning. In one example, subjects can experience an improvement within one week in all eight categories.

The improvement in health can be an improvement in scoring based on a Medical Symptoms Questionnaire (MSQ). This questionnaire contains 71 questions relating to 15 areas of health with scores ranging from 0 to 284. These subdomains include: head, eyes, ears, nose, mouth/throat, skin, heart, lungs, GI tract, joint/muscles, weight, energy/activity, mind, emotions, and MSQ other. A decreasing score indicates improvement. Advantages include: (i) identifies symptoms in most parts of the body, ii) quantifies subject level of symptom, and (iii) provides a simple metric to track clinical improvement. In one example, subjects can experience an improvement within one week.

The improvement in health can be an improvement in symptoms of IBS as determined by the Rome III questionnaire. In one example, subjects can experience an improvement within one week.

The improvement in health can be an improvement in the subject's cardiovascular health. In one example, the subject can experience a reduction in blood pressure that is greater than a reduction attributable to consuming a caloric restricted diet and engaging in moderate physical activity alone. In one embodiment, the subject can experience about a 5.7% reduction in systolic blood pressure within one week. In another example, the subject can experience about a 2.8% reduction in diastolic blood pressure within one week. In yet another example, the subject can experience about a 12% reduction in blood pressure. The reduction in blood pressure can be to one or both of the subject's systolic and/or diastolic blood pressure.

In another example, the subject can experience an improvement in blood triglyceride and/or lipoprotein levels. In one example, the subject can experience a reduction in blood triglyceride levels that is greater than a reduction attributable to consuming a caloric restricted diet and engaging in moderate physical activity alone. In one embodiment, the subject can experience about a 25% reduction in blood triglyceride levels after 4 weeks of participating in the method.

In yet another example, the subject can experience a reduction in blood cholesterol levels. In one example, the subject can experience an improvement in total cholesterol levels. In one embodiment, the subject can experience a reduction in total cholesterol levels that is greater than a reduction attributable to consuming a caloric restricted diet and engaging in moderate physical activity alone. In one example, the subject can experience a reduction in total cholesterol levels of about 12%. In yet another example, the subject can experience a reduction in total cholesterol levels of about 20%. In other examples, the subject can experience a reduction in LDL cholesterol levels that is greater than a reduction attributable to consuming a caloric restricted diet and engaging in moderate physical activity alone. In one example, the subject's LDL cholesterol levels can reduce by about 10%, about 16%, about 17%, about 18%, about 19% or about 20% by engaging in the method.

The subject can also experience a reduction in the subject's overall fat mass. In one example, the subject can experience a reduction in a mass of fat that is greater than a reduction attributable to consuming a caloric restricted diet and engaging in moderate physical activity alone. In one embodiment, the subject can experience about a 5.0% reduction in fat after 4 weeks of participating in the method.

The subject can also experience an improvement in the subject's gut bacteria biome. In one example, the subject can experience a modification in gut bacteria biome that is greater than a modification attributable to consuming a caloric restricted diet and engaging in moderate physical activity alone. In one example, the subject can experience a reduction in nitrate gut levels that is greater than a reduction attributable to consuming a caloric restricted diet and engaging in moderate physical activity alone. In one example, the reduction in nitrate gut levels can occur by regulation of the nitric oxide pathway. In one example, the subject can experience a decrease in fecal zonulin excretion. In one example, the subject can experience a decrease in LBP serum levels. In one example, the subject can experience a decrease in fecal calprotectin.

The subject can also experience a reduction in the subject's metabolic age. In one example the subject can experience a reduction of about 7.3% after 4 weeks of participating in the detoxification method. In another example, the subject can experience a reduction in their metabolic age of between about 1 to about 10% after 4 weeks of participating in the method. In one embodiment, the subject can experience a reduction in their metabolic age that averages about 3 to 6% after participating in the detoxification method.

In one example, the subject can also experience a reduction in 10-year risk of a cardiovascular event of about 15 to 20% after about 1 to about 4 weeks of participating in the detoxification method. In a further example, the subjects can experience an improvement in systemic inflammation through an increase in serum chlorophyllin.

The subject can also experience an improvement in other faucets of their overall health. In one example, the subject can experience improved function in at least one of the cardiovascular, nervous, pulmonary, gastrointestinal, renal, and immune system. In another example, the subject can experience a reduction in their body mass index.

In one embodiment, the detoxification method can be utilized in a subject that is suffering from a physical ailment. In one example, the subject can be suffering from at least one of Alzheimer's disease, angina, asthma, general congestive disorders, Crohn's disease, deep vein thrombosis, dementia, diabetes (types, 1, 2 and 3), diabetic foot disorders, diminished exercise capacity, endothelial dysfunction, endotoxemia, erectile dysfunction, fibromyalgia glomerulonephritis, coronary artery disease, heart attack, heart failure, hypertension, immune deficiency, inflammatory bowel disease, leaky gut, macular degeneration, monocyte-mediated arterial plaque formation, motor dysfunction, oxidation of LDL, peridontal disease, peripheral arterial disease, platelet stickiness, portal hypertension, pregnancy/pre-eclampsia, premature ejaculation, pulmonary hypertension, Raynaud's disease, renal failure, sleep apnea, smooth muscle cell proliferation, stroke, vasculitis and diseases associated with skin such as slow wound healing, wrinkles, and premature signs of aging.

In another embodiment, the detoxification method can occur in an individual at risk for or currently obese. In one example, the co-administering the probiotic component, circulation enhancing component, and fiber component; consuming the caloric restricted diet; engaging in the moderate physical activity; engaging in the cognitive behavioral program; and substituting at least one of breakfast, lunch, or dinner with the meal replacement formulation can prevent the onset of a metabolic disorder associated with obesity. In another example, the metabolic disorder associated with obesity can be a member selected from the group consisting of: Alzheimer's disease, angina, asthma, general congestive disorders, Crohn's disease, deep vein thrombosis, dementia, diabetes (types, 1, 2 and 3), diabetic foot disorders, diminished exercise capacity, endothelial dysfunction, endotoxemia, erectile dysfunction, fibromyalgia glomerulonephritis, coronary artery disease, heart attack, heart failure, hypertension, immune deficiency, inflammatory bowel disease, leaky gut, macular degeneration, monocyte-mediated arterial plaque formation, motor dysfunction, oxidation of LDL, peridontal disease, peripheral arterial disease, platelet stickiness, portal hypertension, pregnancy/pre-eclampsia, premature ejaculation, pulmonary hypertension, Raynaud's disease, renal failure, sleep apnea, smooth muscle cell proliferation, stroke, vasculitis and diseases associated with skin such as slow wound healing, wrinkles, and premature signs of aging.

It is noted that when discussing detoxification systems and associated methods, each of these discussions can be considered applicable to each of these examples, whether or not they are explicitly discussed in the context of that example. Thus, for example, in discussing details about the detoxification systems per se, such discussion also refers to the various methods described herein, and vice versa.

Embodiments

In one example, there is provided a detoxification system including an effective amount of a probiotic component and a fiber component, wherein the detoxification system increases urinary heavy metal excretion, decreases a fecal zonulin level, decreases a fecal calprotectin level, decreases a serum lipopolysaccharide binding protein (LBP) level, increases at least one of a salivary nitrite level and a serum arginine level, or a combination thereof in a subject as compared to a baseline level prior to administration of the detoxification system in an effective dosing regimen.

In one example of the detoxification system, the probiotic component comprises at least one of *Bacillus* spp., *Lactobacillus* spp., *Bifidobacterium* spp., and *Streptococcus* spp.

In one example of the detoxification system, the probiotic component comprises *Bacillus* spp.

In one example of the detoxification system, the *Bacillus* spp. comprises *Bacillus coagulans*.

In one example of the detoxification system, the probiotic component includes *Lactobacillus* spp.

In one example of the detoxification system, the *Lactobacillus* spp. comprises *L. rhamnosus, L. acidophilus, L. brevis, L. bulgaricus, L. plantarum, L. casei, L. salivarius*, or a combination thereof.

In one example of the detoxification system, the probiotic component comprises *Bifidobacterium* spp.

In one example of the detoxification system, the *Bifidobacterium* spp. comprises *B. bifidum, B. infantis, B. longum*, or a combination thereof.

In one example of the detoxification system, the probiotic component comprises *Streptococcus* spp.

In one example of the detoxification system, the *Streptococcus* spp. comprises *Streptococcus thermophilus*.

In one example of the detoxification system, the probiotic component comprises a daily dose of about 2 billion colony forming units (cfu) to about 60 billion cfu of probiotic.

In one example of the detoxification system, the probiotic component further comprises inulin, fructooligosaccharide, cellulose, prebiotic fibers, or a combination thereof.

In one example of the detoxification system, the probiotic component is formulated as a solid oral dosage form.

In one example of the detoxification system, the detoxification system further comprises a circulation enhancing component.

In one example of the detoxification system, the circulation enhancing component includes one or more of red beet root, L-arginine, L-glutamine, and grape extract.

In one example of the detoxification system, the grape extract comprises grape polyphenol extract, grape seed extract, grape skin extract, or a combination thereof.

In one example of the detoxification system, the circulation enhancing component further comprises at least one of apple fruit extract, green tea leaf extract, olive leaf extract, stevia leaf extract, watermelon whole fruit extract, inulin, and pomegranate fruit juice concentrate.

In one example of the detoxification system, the circulation enhancing component further comprises apple extract, green tea extract, and olive extract.

In one example of the detoxification system, the apple extract, grape extract, green tea extract, and olive extract are present at a weight ratio of from about 1:1:1:1 to about 6:1:3:1.

In one example of the detoxification system, the circulation enhancing component further comprises at least one of vitamin C, vitamin B12, folic acid, vitamin B6, thiamin, and vitamin D.

In one example of the detoxification system, the circulation enhancing component further comprises at least one of natural citrus sweetener, citrus blend natural flavor, natural cherry flavor, lemonade flavor, and D-ribose.

In one example of the detoxification system, the circulation enhancing component further comprises at least one of citric acid, malic acid, magnesium oxide, and silicon dioxide.

In one example of the detoxification system, the fiber component comprises one or more of psyllium hulls, apple fruit fiber, flax seeds, guar gum, and acacia gum.

In one example of the detoxification system, the fiber component further comprises at least one of chlorophyllin, l-glutamine, and zinc.

In one example of the detoxification system, the fiber component further comprises at least one of cabbage leaf, broccoli flowers, rosemary leaf, tomato fruit, turmeric root, carrot root, and inulin.

In one example of the detoxification system, the fiber component further comprises at least one of apple extract, grape extract, green tea extract, and olive extract.

In one example of the detoxification system, the fiber component further comprises at least one of vitamin B1, vitamin B2, vitamin B6, vitamin B12, and vitamin D.

In one example of the detoxification system, the circulation enhancing component, the fiber component, or both further comprise one or more of iron, docosahexaenoic acid (DHA), eicosapentaenoic acid (EPA), calcium, niacin, folic acid, biotin, panthothenic acid, phosphorus, iodine, magnesium, zinc, selenium, copper, manganese, chromium, potassium, inositol, p-Aminobenzoic acid (PABA), choline, bitartrate, lycopene, lutein, antioxidants, dandelion root, alfalfa aerial parts, asparagus stem, broccoli flowers, cabbage leaf, hesperidin bioflavonoid extract, lemon bioflavonoid extract, rutin, rose hips extract, chlorophyll, kelp leaf, kelp stem, cranberry fruit, mangosteen fruit, carrot root, spinach leaf, spinach stem, tomato fruit, acai berry, pomegranate fruit extract, l-leucine, l-lysine, l-valine, l-isoluecine, l-phenyalanine, l-threonine, l-arginine, l-citrulline, l-methionine, l-tyrosine, l-cysteine, or combinations thereof.

In one example of the detoxification system, at least two of the probiotic component, the circulation enhancing component, and the fiber component are formulated as a single composition.

In one example of the detoxification system, the probiotic component, the circulation enhancing component, and the fiber component are each formulated as separate compositions.

In one example of the detoxification system, the separate compositions are formulated as oral dosage forms.

In one example of the detoxification system, the oral dosage forms are selected from a liquid, a capsule, a confectionery, a bar, a powder, and combinations thereof.

In one example of the detoxification system, the detoxification system further comprises a high-protein meal replacement component including a minimum of 15 grams of protein.

In one example of the detoxification system, the detoxification system further stimulates an increase in weight loss in a subject of about 3% as compared to a baseline level prior to administering the therapeutic system when the therapeutic system is administered daily for a period of at least about 4 weeks in combination with a caloric restricted diet including a minimum daily protein intake of about 3 oz. and daily physical activity equivalent to about 5000 steps per day.

In one example, there is provided a detoxification method that accelerates detoxification in a subject, comprising administering a probiotic component to the subject and administering a fiber component to the subject, wherein the detoxification method increases urinary heavy metal excretion, decreases a fecal zonulin level, decreases a fecal calprotectin level, decreases a serum lipopolysaccharide binding protein (LBP) level, increases at least one of a salivary nitrite level and a serum arginine level, or a combination thereof in the subject as compared to a baseline level prior to administration of the individual components in an effective dosing regimen.

In one example of the detoxification method, the method further comprises a caloric restricted diet with a minimum daily protein intake of about 3 ounces (oz.).

In one example of the detoxification method, the caloric restricted diet comprises a total daily caloric intake of from about 1250 calories to about 1500 calories.

In one example of the detoxification method, the minimum daily protein intake comprises about 7 oz. of protein.

In one example of the detoxification method, the minimum daily protein intake comprises about 12 oz. of protein.

In one example of the detoxification method, the caloric restricted diet comprises a daily vegetable intake of from about 3 cups to about 6 cups of vegetables, a daily minimum of fresh greens intake of about 5 ounces, and a daily minimum fluid intake of about 48 fluid ounces.

In one example of the detoxification method, the caloric restricted diet further comprises a daily intake of at least one serving of fruit or legumes.

In one example of the detoxification method, the method further includes daily physical activity of equivalent to at least about 5000 steps per day.

In one example of the detoxification method, the daily physical activity comprises physical activity that expends from about 115 calories to about 300 calories per day 5 days per week.

In one example of the detoxification method, the probiotic component, the circulation enhancing component, and the fiber component are administered as a single composition.

In one example of the detoxification method, at least two of the probiotic component, the circulation enhancing component, and the fiber component are administered as a single composition.

In one example of the detoxification method, the probiotic component, the circulation enhancing component, and the fiber component are administered as separate compositions.

In one example of the detoxification method, the probiotic component, the circulation enhancing component, and the fiber component are administered orally.

In one example of the detoxification method, the probiotic component, the circulation enhancing component, and the fiber component are administered as a liquid, a suspension, a powder, a tablet, a bar, or a combination thereof.

In one example of the detoxification method, the probiotic component is administered in an amount to provide a daily dose of from about 2 billion cfu to about 60 billion cfu of probiotic.

In one example of the detoxification method, the probiotic component is administered twice daily.

In one example of the detoxification method, the method further includes administering a circulation enhancing component.

In one example of the detoxification method, the circulation enhancing component is administered at a daily dose of from about 5 grams (g) to about 30 g.

In one example of the detoxification method, the circulation enhancing component is administered once daily.

In one example of the detoxification method, the circulation enhancing component is administered in the evening.

In one example of the detoxification method, the fiber component is administered in an amount to provide a daily dose of soluble fiber of from about 8 g to about 15 g.

In one example of the detoxification method, the fiber component is administered twice daily.

In one example of the detoxification method, the method further comprises administering a high-protein meal replacement component having a minimum of about 15 grams of protein.

In one example of the detoxification method, the steps of administering each of the probiotic component, the circulation enhancing component, and the fiber component are performed for a period of at least 1 week.

In one example of the detoxification method, the method further stimulates an increase in weight loss in the subject of about 3% as compared to a baseline level prior to daily administration of the probiotic component, the circulation enhancing component, and the fiber component for a period of at least about 4 weeks.

In one example of the detoxification method, the subject has a body mass index (BMI) of at least 25 kg/m$^2$.

In one example, there is provided a detoxification method of improving the health of a subject eating a caloric restricted diet with a minimum daily protein intake of about 3 ounces (oz.) and engaging in daily physical activity equivalent to about 5,000 steps per day, comprising co-administering to the subject a high-protein meal replacement formulation designed to deliver a minimum of 40 grams protein and a detoxification system as described herein.

In one example of the detoxification method of improving the health of a subject, the high-protein meal replacement formulation daily replaces at least one of breakfast, lunch, and dinner.

In one example of the detoxification method of improving the health of a subject, the high-protein meal replacement formulation comprises from about 20 g protein to about 60 g protein, from about 3 g fat to about 15 g fat, from about 32 g carbohydrates to about 96 g carbohydrates, and from about 180 total calories to about 540 total calories.

In one example of the detoxification method of improving the health of a subject, the high-protein meal replacement formulation is administered as a beverage.

In one example of the detoxification method of improving the health of a subject, co-administering is performed for a period of at least 1 week.

In one example of the detoxification method of improving the health of a subject, the caloric restricted diet comprises a total daily caloric intake of from about 1250 calories to about 1500 calories.

In one example of the detoxification method of improving the health of a subject, the caloric restricted diet comprises a minimum daily protein intake of about 12 oz. of protein.

In one example of the detoxification method of improving the health of a subject, the caloric restricted diet comprises a daily vegetable intake of from about 3 cups to about 6 cups of vegetables, a daily minimum of fresh greens intake of about 5 ounces, and a daily minimum fluid intake of about 48 fluid ounces.

In one example of the detoxification method of improving the health of a subject, the caloric restricted diet further comprises a daily intake of at least one serving of fruit or legumes.

In one example of the detoxification method of improving the health of a subject, the daily physical activity comprises physical activity that expends from about 115 calories to about 300 calories per day 5 days per week.

In one example of the detoxification method of improving the health of a subject, co-administering, in connection with the caloric restricted diet and moderate physical activity, provides improved function in at least one of the cardiovascular system, the nervous system, the pulmonary system, the gastrointestinal system, the renal system, and the immune system as compared to a function of said system is the subject prior to co-administering the high-protein meal replacement and the therapeutic system.

In one example of the detoxification method of improving the health of a subject, co-administering, in connection with the caloric restricted diet and moderate physical activity, prevents the onset of a metabolic disorder associated with obesity.

In one example of the detoxification method of improving the health of a subject, the metabolic disorder comprises at least one of Alzheimer's disease, angina, asthma, general congestive disorders, Crohn's disease, deep vein thrombosis, dementia, diabetes (types, 1, 2 and 3), diabetic foot disorders, diminished exercise capacity, endothelial dysfunction, endotoxemia, erectile dysfunction, fibromyalgia glomerulonephritis, coronary artery disease, heart attack, heart failure, hypertension, immune deficiency, inflammatory bowel disease, leaky gut, macular degeneration, monocyte-mediated arterial plaque formation, motor dysfunction, oxidation of LDL, periodontal disease, peripheral arterial disease, platelet stickiness, portal hypertension, pregnancy/pre-eclampsia, premature ejaculation, pulmonary hypertension, Raynaud's disease, renal failure, sleep apnea, smooth muscle cell proliferation, stroke, vasculitis, slow wound healing, wrinkles, and premature signs of aging.

In one example of the detoxification method of improving the health of a subject, the subject has at least one of Alzheimer's disease, angina, asthma, general congestive disorders, Crohn's disease, deep vein thrombosis, dementia, diabetes (types, 1, 2 and 3), diabetic foot disorders, diminished exercise capacity, endothelial dysfunction, endotoxemia, erectile dysfunction, fibromyalgia glomerulonephritis, coronary artery disease, heart attack, heart failure, hypertension, immune deficiency, inflammatory bowel disease, leaky gut, macular degeneration, monocyte-mediated arterial plaque formation, motor dysfunction, oxidation of LDL, periodontal disease, peripheral arterial disease, platelet stickiness, portal hypertension, pregnancy/pre-eclampsia, premature ejaculation, pulmonary hypertension, Raynaud's disease, renal failure, sleep apnea, smooth muscle cell proliferation, stroke, vasculitis, slow wound healing, wrinkles, and premature signs of aging.

EXAMPLES

Figure 3:
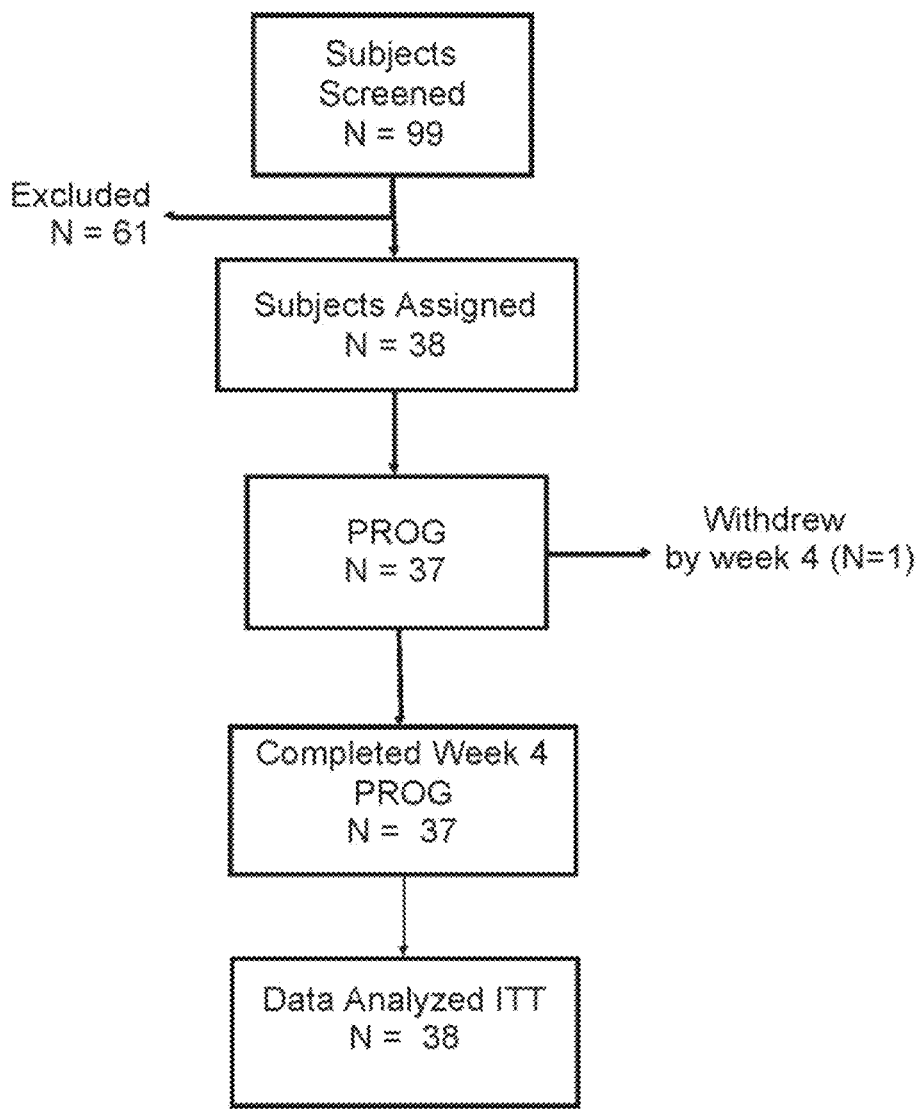
FIG. 3 is a flow chart displaying the subject selection and disposition in the Example.

Example 1—Evaluation of a Program for Healthy Weight, Improved Detoxification, Cardiometabolic Function and Gut and Microbiome Function This trial was a single-arm, open-label study to evaluate the safety and efficacy of a diet and life style modification program with targeted nutritional supplementation designed to enhance detoxification systems, initiate restoration of a healthy microbiome, and improve bowel function in generally healthy subjects. FIG. 3 illustrates a flow chart depicted the general flow of the trial.

All subjects received the nutritional supplement program outlined in Table 4. Subjects were offered a choice of four unique protein shake formulations (Love & Peas Sugar Free and Love and Peas containing pea protein, Nutri-Burn containing whey protein, SmartMeal containing mixed soy, pea and chlorella protein) and consumed 2 protein shakes per day. Additional supplements consumed were *Bacillus coagulans* 3 capsules once a day, Biome NO+ twice a day, and Purify twice a day as more fully described below.

TABLE 4

Purify Clinical Study Design

Recruiting and Screening

Recruit generally healthy, overweight and obese adults
Measure anthropometric, lipid, glycemic variables and blood pressure
Treatment Weeks 1-4

High phytonutrient protein rich food plan
Choose foods that are protein-rich
High phytonutrient content
Count servings of food, not calories
5 meals and snacks daily
Limit sugars and refined carbohydrates
Physical activity - 5,000 steps per day
20 g Protein meal replacement shakes containing carbohydrates, fats, vitamin and minerals. Daily serving size was 2 scoops twice a day, delivering 40 g of protein per day.
Biome NO+ formulation of amino acids, combined with red beet root, polyphenol fruit concentrates, vitamins and minerals was taken twice per day.
Purify fiber Supplement containing chlorophyllin, psyllium hulls, inulin, L-glutamine, fruit concentrates and zinc providing 6 grams of fiber per serving taken twice per day.
*Bacillius coagulans* supplement probiotic was administered as three capsules once a day.
Subject Assessment Baseline, Weeks 1, 2 & 4

Subjective Assessments: Short Form Health Survey (SF-36) and Medical Screening Questionnaire (MSQ)
Anthropometric: Gender, age, weight, height, BMI, body fat mass, % body fat, % visceral fat, waist circumference, waist/hip, muscle mass, bone mass and metabolic age.
Lipids: Total cholesterol, LDL Cholesterol, HDL Cholesterol, Triglycerides, Cholesterol/HD, LDL/HDL, and TG/HDL.
Glycemic: Glucose, insulin, HbA1C, HOMA-IR, valine, isoleucine and leucine
Vascular Biomarkers: Blood pressure, salivary nitrite, serum arginine, dimethylasymmetric arginine.
Liver Function/Detoxification: Fatty Liver Index, GGT, AST, ALT, AST/ALT, ALP, bilirubin, albumin, total protein, and metallothionein.
Urinary Heavy Metals: Aluminum, antimony, arsenic, barium, beryllium, bismuth, cadmium, cesium, gadolinium, lead, mercury, nickel, palladium, platinum, tellurium, thallium, thorium, tin, tungsten, and uranium.
Gut Functioning: Lipopolysaccharide binding protein, fecal zonulin, serum zonulin, fecal calprotectin, bowel movements per day, daily Bristol Stool Scoring averages.

Screening Visit: The purpose of the screening visit was to determine volunteer eligibility for study participation. Before the onsite screening, the potential subjects were required to answer the Purify Readiness Scale over the phone or through email (Table 5). Upon review of screening data acceptable for inclusion, a telephone interview with a study investigator was completed to confirm eligibility, and document absence of contraindications to participation. Subjects meeting screening criteria were rank ordered on the basis of their Purify Readiness Scale scores. Subjects with higher scores were selected preferentially for inclusion.

Subjects whose scores met the inclusion criteria were asked to participate in onsite screening. Prior to any study procedures being conducted, Informed Consent was signed and witnessed. Onsite screening included measurement of height, weight, waist circumference, and vital signs; completion of medical history questionnaire; review of medical history and current medications by clinician; and collection of fasting blood for testing for: Complete Blood Count (CBC) and Comprehensive Metabolic Profile (CMP) as well as a pregnancy test in females of child-bearing potential. Screening labs were performed within 8 weeks of beginning the trial. Fasting was defined as greater than 8 hours and less than 12 hours of refraining from consumption of food and beverages though unlimited consumption of water was allowed and encouraged.

TABLE 5

Purify Readiness Scale A score of ≥8 points on the Purify Readiness Scale was a required inclusion criteria Body Mass Index (BMI):

| | |
|---|---|
| 20 kg/m2 ≤ BMI ≤ 25 kg/m2 | 0 points |
| 25 kg/m2 ≤ BMI ≤ 30 kg/m2 | 1 point |
| 30 kg/m2 ≤ BMI ≤ 35 kg/m2 | 2 points |
| 35 kg/m2 ≤ BMI ≤ 50 kg/m2 | 3 points |

Number of Silver Amalgam Dental Fillings:

| | |
|---|---|
| 0 | 0 points |
| 1 to 3 | 1 point |
| 4 to 6 | 2 points |
| >6 | 3 points |

Hypercholesterolemia:
Most recently, have you been told your cholesterol levels are:

| | |
|---|---|
| Normal | 0 points |
| Previously high, currently | 1 point |
| Currently high | 2 points |

Hyperglycemia:
Most recently, have you been told your blood sugar levels are:

| | |
|---|---|
| Normal | 0 points |
| Previously high, currently | 1 point |
| Currently high | 2 points |

Hypertension:
Most recently, have you been told your blood pressure

| | |
|---|---|
| Normal | 0 points |
| Previously high, currently | 1 point |
| Currently high | 2 points |

Non-alcoholic Fatty Liver Disease:
Have you been told you have "Fatty Liver

| | |
|---|---|
| No | 0 points |
| Yes | 2 points |

Irritable Bowel Syndrome:
Have you been told you have "Irritable Bowel Syndrome"?

| | |
|---|---|
| No | 0 points |
| Yes | 2 points |

Are you satisfied with your bowel habits"?

| | |
|---|---|
| No | 0 points |
| Yes | 2 points |

How many days per week do you have a normal bowel movement?

| | |
|---|---|
| 7 days | 0 points |
| 5-6 days | 1 point |

TABLE 5-continued

Purify Readiness Scale A score of ≥8 points on the
Purify Readiness Scale was a required inclusion criteria

| | |
|---|---|
| 3-4 days | 2 points |
| 0-2 days | 3 points |
| Quality of Life/Fatigue: | |
| Do you wake up feeling fatigued? | |
| Never | 0 points |
| Some mornings | 1 point |
| Most or all mornings | 2 points |
| Quality of Life/Depression: | |
| Do you feel out-of-sorts or even depressed? | |
| Never | 0 points |
| Some mornings | 1 point |
| Most or all mornings | 2 points |
| Quality of Diet: | |
| Do you eat fried of fast foods? | |
| Never | 0 points |
| Some days | 1 point |
| Most or all days | 2 points |
| Quality of Diet: | |
| Do you eat 2 or more servings of vegetables per day? | |
| Never | 0 points |
| Some days | 1 point |
| Most or all days | 2 points |

High phyto-nutrient protein rich food plan: Subjects were provided with information on a specific food plan to be followed through the 4-week study. The plan promoted achieving health goals by counting servings of food and not calories. The food plan ensures that the required number of servings each day provides a balanced blend of protein, carbohydrates, and fat and that the subjects received a diet packed with vitamins, minerals, and nutrients from plants. The plan encompassed five meals and snacks daily along with limiting sugars, refined carbohydrates, and grains to provide an estimated 1,440 calories per day. See Table 6.

TABLE 6

HyPro Food Plan for Purify Program

| Food Category | Daily Servings | Serving Size |
|---|---|---|
| Meal Protein | 3 | Palm size |
| Vegetables | 6 | One-half to 1 cup |
| Fresh Greens | 5 ounces | Varies |
| Fruit | 1 | Varies |
| Legumes (optional, replaces fruit serving) | 1 | One-half cup |
| Dairy (optional, replaces one snack protein) | 1 | Varies |
| Oils and Fats | 5 | Varies |
| Beverages | 6 to 8 (at least) | Eight fluid ounces |

Moderate physical activity: All subjects received instruction and were required to follow the lifestyle change program consisting of the food plan (above), including Meal Replacement and Detoxification Stimulating Supplements (See Table 7), and exercise recommendations. The exercise requirements included (1) using a pedometer, (2) keeping a log of daily steps aiming for at least 5,000 steps per day (about 2.5 miles), with at least 30 minutes of moderate intensity focusing on aerobic movement exercising, and (3) adding resistance training and flexibility exercises at least twice a week.

TABLE 7

Meal Replacement and Detoxification Stimulating Supplements

| Meal Supplement | Daily Servings | Function |
|---|---|---|
| Meal Replacement | 2 scoops 2× per day | Protein, antioxidants, and micronutrients |
| Detoxification and Gut Supporting Supplements | | |
| Bacillus coagulans | 3 capsules once per day (3 billion cfu) | Limit excessive growth of harmful gut bacteria |
| Biome NO+ | One scoop with meal twice a day | Generate NO, which plays an important role in the protection against the onset and progression of cardiovascular disease. |
| Purify Fiber | 1 stick pack with a meal twice a day | Support purification of the gut and helps restore balance to the microbiome. |

Meal Replacement Formulation: Subjects consumed a meal replacement formulation (MR) twice per day. The meal replacement formulation provided a minimum of 40 g protein, about 6 to 10 g fat, about 32 g carbohydrate, about 360 calories per day (See Table 8) and contained the following ingredients: ascorbic acid, biotin, *Chlorella/Chlorella vulgaris*, chromium nicotinate, copper citrate, D-calcium pantothenate, cyanocobalamin, flax seed/*Linum usitatissimum*, folic acid, fructooligosaccharide (fiber), magnesium oxide, manganese citrate, maltodextrin, medium chain triglycerides, natural vanilla flavor, niacinamide, non-dairy creamer (contains milk, soy), potassium citrate potassium iodide, riboflavin, sugar cane (*Saccharum officinarum*), sodium molybdate dihydrate, sodium selenate (selenium), stevia leaf extract/*Stevia rebaudiana*, thiamin HCl, tricalcium phosphate, vitamin a palmitate, vitamin D3, xanthan gum, zinc citrate, cellulose gum, guar gum, pyridoxine hydrochloride, salt, and vitamin E tocopherol.

TABLE 8

Meal Replacement Formulations (MR) Taken Twice per Day†

| Ingredient | MR1 | MR2 | MR3 | % Daily Value |
|---|---|---|---|---|
| Serving Size (g) | 46 | 45 | 45 | |
| Calories | 184 | 180 | 173 | |
| Fat (g) | 5 | 3 | 5 | |
| Saturated Fat (g) | 2 | 1 | 1 | |
| Trans Fat (g) | 0 | 0 | 0 | |
| Cholesterol (mg) | 32 | 0 | 0 | |
| Sodium (mg) | 104 | 150 | 307 | |
| Potassium (mg) | 368 | 95 | 187 | |
| Carbohydrate (g) | 14 | 16 | 16 | |
| Dietary Fiber (g) | 5 | 3 | 3 | |
| Sugars (g) | 5 | 9 | 8 | |
| Protein (g) | 20 | 20 | 20 | |
| Phytosterols (mg) | 2000 | 2000 | 2000 | * |
| Vitamin A (IU) | 48 | 75 | 47 | 35% |
| Vitamin C (mg) | 48 | 75 | 47 | 100% |
| Calcium (mg) | 96 | 2 | 33 | 60% |
| Iron (mg) | 0 | 0 | 0 | 20% |
| Vitamin A (IU) | 48 | 75 | 47 | 35% |
| Vitamin D (IU) | 0 | 75 | 47 | 10% |
| Vitamin E (IU) | 48 | 0 | 47 | 35% |
| Vitamin K (mcg) | 0 | 0 | 0 | |
| Thiamin (mg) | 48 | 75 | 47 | 50% |
| Riboflavin (mg) | 48 | 75 | 47 | 50% |
| Niacin (mg) | 48 | 75 | 47 | 50% |
| Vitamin B6 (mg) | 48 | 75 | 47 | 1250% |
| Folate (as folic acid and L-5-methyltetrahydrofolate) (mcg) | 104 | 75 | 47 | 100% |

TABLE 8-continued

Meal Replacement Formulations (MR) Taken Twice per Day†

| Ingredient | MR1 | MR2 | MR3 | % Daily Value |
|---|---|---|---|---|
| Vitamin B12 (as cyanocobalamin) (mcg) | 48 | 75 | 47 | 500% |
| Biotin (mcg) | 48 | 75 | 47 | 50% |
| Pantothenic Acid (mg) | 48 | 75 | 47 | 50% |
| Phosphorus (mg) | 48 | 0 | 20 | 55% |
| Iodine (mcg) | 0 | 75 | 47 | 50% |
| Magnesium (mg) | 72 | 0 | 33 | 60% |
| Zinc (mg) | 0 | 75 | 47 | 60% |
| Selenium (mcg) | 0 | 75 | 47 | |
| Copper (mg) | 0 | 75 | 47 | 50% |
| Manganese (mg) | 0 | 75 | 47 | 25% |
| Chromium (mcg) | 176 | 75 | 47 | 80% |
| Molybdenum | 0 | 75 | 0 | |
| Chloride (mg) | 0 | 0 | 0 | 10% |

†Values in table represent single serving amounts and should be multiplied by two to determine total daily supplementation (e.g. calories per day = 368, 360 and 348, respectively).

*Bacillus coagulans*: The *Bacillus coagulans* supplement was manufactured by Nature's Sunshine Products in Spanish Fork, Utah. It contained 3 billion cfu per 3 capsules. Subjects were instructed to take 3 capsules per day at dinner.

Biome NO+: The Biome NO+ phytochemical supplement was manufactured by Nature's Sunshine Products in Spanish Fork, Utah. Biome NO+ provides a blend of amino acids, specifically l-arginine and l-glutamine, combined with red beet root, grape polyphenol extract, vitamins and minerals. L-arginine and l-glutamine are converted into nitric oxide in the body. Red beet root's high inorganic nitrate content (250 mg/kg of fresh weight) may be reduced to nitrite by symbiotic bacteria in the body, and subsequently converted enzymatically in the gut to Nitric Oxide (NO). Nitric oxide is a gaseous lipophilic free radical cellular messenger generated by nitric oxide synthase. NO plays an important role in the protection against the onset and progression of cardiovascular disease. Mechanistically, vascular dysfunction is characterized by a reduced bioavailability of endothelium-derived vasoprotective NO. NO is a vasodilator with associated antiplatelet, anti-inflammatory, and antiproliferative effects.

TABLE 9

Biome NO+ Formulation Taken Twice per Day†

| Ingredient Description | % Formula | g/Formula |
|---|---|---|
| Red Beet Root (Nitrate 2%) (KR) | 27.645% | 2.9856 |
| Inulin (chicory root extract) [HD food grade] | 18.624% | 2.0114 |
| Citric Acid | 11.519% | 1.2440 |
| L-Arginine [granular] | 9.215% | 0.9952 |
| L-Glutamine | 9.215% | 0.9952 |
| Xylitol [bulk] | 4.607% | 0.4976 |
| Pomegranate Fruit Juice Concentrate | 4.147% | 0.4478 |
| Natural Citrus Sweetener [CitriSweet(TM)] | 4.147% | 0.4478 |
| Malic Acid | 2.534% | 0.2737 |
| Silicon Dioxide [Syloid ® 244] | 1.382% | 0.1493 |
| Thiamin (B1) (thiamine mononitrate) [100%] | 0.009% | 0.0010 |
| Citrus Blend Natural Flavor [WONF] | 0.921% | 0.0995 |
| Natural Cherry Flavor | 1.382% | 0.1493 |
| Magnesium Oxide [60% Mg, powder] | 0.774% | 0.0836 |
| Vitamin C (ascorbic acid) [100%, fine powder] | 0.691% | 0.0746 |

TABLE 9-continued

Biome NO+ Formulation Taken Twice per Day†

| Ingredient Description | % Formula | g/Formula |
|---|---|---|
| Stevia Leaf Extract | 0.645% | 0.0697 |
| Grape Skin Extract | 0.369% | 0.0398 |
| Apple Fruit Extract [75% polyphenols] | 0.276% | 0.0299 |
| D-Ribose | 0.276% | 0.0299 |
| Watermelon Whole Fruit Extract [20% Citrulline] | 0.212% | 0.0229 |
| Vitamin D3 (cholecalciferol) [100,000 IU/g, 100 | 0.147% | 0.0159 |
| Green Tea Leaf Extract [80%, decaffeinated] | 0.138% | 0.0149 |
| Red Grape Polyphenol Extract [ExGrape(TM) red wine extract] | 0.046% | 0.0050 |
| Grape Seed Extract [MegaNatural ®] | 0.046% | 0.0050 |
| Olive Leaf Extract [12%, 7:1] | 0.046% | 0.0050 |
| Folic Acid [10%, trituration] | 0.028% | 0.0030 |
| Vitamin B6 (pyridoxine hydrochloride) [82% B6] | 0.028% | 0.0030 |
| Vitamin B12 (cyanocobalamin) [1%, trituration] | 0.008% | 0.0009 |
| Lemonade NAT WONF Flavor LeLemon | 0.921% | 0.0995 |

Purify Program: The Purify Program primes detoxification pathways, preparing the body to eliminate pollutants, restore, and balance the microbiome. Purify was manufactured by Nature's Sunshine Products in Spanish Fork, Utah. It functions as a microbiome and detoxification supplement formula with nutrients that support purification of the gut and help restore balance to the microbiome. This formula supports the integrity and function of the microbiome, cleanses the digestive tract, detoxifies the body and provides sustained energy. Additionally, Purify is a source of glutamine, an important amino acid that supports healthy epithelial function in the gut, along with a phytonutrient blend to provide superior free-radical protection. Other ingredients included zinc, broccoli, chlorophyll, synergistic antioxidant phytonutrient blend, inulin (prebiotic), soluble and insoluble fiber. One serving of Purify supplied 6 grams of soluble fiber from inulin, psyllium, apple fruit fiber, flax seed, guar gum and acacia gum. Two servings were consumed daily—one between breakfast and lunch and one between lunch and dinner.

TABLE 10

Typical Purify Formulations Taken Twice per Day

| Ingredient Description | 17368 | 92514 | 21949 | 21401† |
|---|---|---|---|---|
| Psyllium Hulls [50] | 22.5% | 19.3% | 23.7% | 24.0% |
| L-Glutamine | 17.9% | 15.6% | 18.9% | 19.1% |
| Inulin (chicory root extract) [HD food grade] | 17.9% | 15.2% | 18.9% | 19.1% |
| Apple Fruit Fiber [40 mesh] | 12.9% | 10.0% | 13.6% | 13.8% |
| Flax Seed | 4.3% | 3.8% | 4.5% | 4.6% |
| Guar Gum [Tico-LV] | 4.3% | 3.8% | 4.5% | 4.6% |
| Gum Arabic (Talha) | 4.3% | 3.8% | 4.5% | 4.6% |
| Citric Acid | 3.6% | 5.8% | 2.5% | 2.5% |
| Broccoli Flowers | 2.2% | 6.3% | 2.3% | 2.3% |
| Fructose | 7.2% | | | |
| Turmeric Root | 0.1% | 6.3% | 0.1% | 0.1% |
| Citrus Blend Natural Flavor [WONF] | 1.3% | 2.3% | 0.9% | 0.9% |
| Natural Orange Flavor Powder | | | 2.3% | 2.3% |
| Raspberry Natural Flavor [WONF] | | 3.4% | | |

TABLE 10-continued

Typical Purify Formulations Taken Twice per Day

| Ingredient Description | 17368 | 92514 | 21949 | 21401† |
|---|---|---|---|---|
| Xanthan Gum [Keltrol(TM) Tf] | | 2.3% | | |
| Sodium Copper Chlorophyllin | 0.7% | | 0.8% | 0.8% |
| Silicon Dioxide [Syloid ® 244] | | 1.0% | 1.0% | |
| Stevia Leaf Extract [97% RebA powder] | | 0.7% | 0.4% | 0.4% |
| Apple Fruit Extract [75% polyphenols] | 0.2% | 0.2% | 0.2% | 0.2% |
| Zinc Citrate [32% Zn, dihydrate] | 0.0% | | 0.2% | 0.2% |
| Green Tea Leaf Extract [80%, decaffeinated] | 0.1% | 0.1% | 0.1% | 0.1% |
| Cabbage Leaf | 0.1% | 0.1% | 0.1% | 0.1% |
| Carrot Root | 0.1% | 0.1% | 0.1% | 0.1% |
| Red Beet Root | 0.1% | 0.1% | 0.1% | 0.1% |
| Rosemary Leaf | 0.1% | 0.1% | 0.1% | 0.1% |
| Tomato Fruit | 0.1% | 0.1% | 0.1% | 0.1% |
| Stevia Leaf Extract | 0.2% | | | |
| Grape Seed Extract [MegaNatural ®] | 0.0% | 0.0% | 0.0% | 0.0% |
| Olive Leaf Extract [12%, 7:1] | 0.0% | 0.0% | 0.0% | 0.0% |

†Formulation used in Example

Clinical Visits: There were 4 Clinical Visits (Clinical Visits 1-4) during the 4-week study. The clinical visits were individual appointments and were held during weeks 0, 1, 2, and 4. The focus of the clinical visits was the collection of safety, tolerance and acceptability data as well as data pertaining to healthy bowel function and individually focused diet instruction and counseling.

All subjects were asked to make dietary changes during the 4-week study. Subjects were instructed to follow the High PhytoPro Food Plan (Table 6). Subjects were asked to make no changes in prescription and OTC medications and nutritional supplements (except for the administration of nutritional supplements as supplied) during the study.

During the clinical visits, the study clinician reviewed questionnaires including (i) 2-day food recall, (ii) MOS-SF 36 questionnaires [Patel A A, Donegan D, Albert T: The 36-item short form. J Am Acad Orthop Surg 2007; 15:126-34], (iii) Gastrointestinal Quality of Life questionnaire with Bristol Stool Chart Scores—Baseline and Follow-up Visits [Borgaonkar M R, Irvine E J: Quality of life measurement in gastrointestinal and liver disorders. Gut 2000; 47:444-54], Medical Symptoms Questionnaire [Nature's Sunshine], (iv) clinical visit questionnaire [Nature's Sunshine], and (v) food plan compliance questionnaire [Nature's Sunshine], for signs and symptoms of adverse events, compliance to the study product and the dietary program and to answer any questions from the subject.

Physical measurements were conducted at all visits. Phlebotomy was conducted at Week 0, 1, 2 and 4. Stool samples were collected during Week 0, 1, 2 and 4. Twenty-four hour urine collections were made at Week 0, 1, 2 and 4. On Day 2 of the study and on every Wednesday thereafter during the study, the subjects were required to use the nitrite strip tests four times: 1 hour before and 1 hour after the BiomeNO+ consumption.

Group Clinical Visits 1-5 (weeks 0, 1, 2, 3 and 4): Subjects met collectively with the study clinician in small groups each Tuesday during the study. During these visits, study staff presented education and experiential content to support healthy lifestyle changes. Data collection (limited to weight and BP measurement) was conducted at Group Clinical Visits 1-5 (weeks 0, 1, 2, 3 and 4). Subjects received electronic reminders and the opportunity to participate in a social media forum limited to study subjects and study staff.

Concomitant Medications and Procedures: All concomitant medications taken during study participation were recorded on the visit progress note. A prescription medication was defined as a medication that can be prescribed only by a properly authorized/licensed clinician. Medications to be reported were concomitant prescription medications, over-the-counter medications, medical foods, and nutritional supplements taken during the course of the study.

Prohibited Medications and Procedures: No concomitant prescription medications, over-the-counter medications, medical foods, and nutritional supplements were to be started or doses changed during the study unless they were prescribed by the PI (or the subject's primary care giver) for treatment of a specific clinical event.

Inclusion criteria: (1) Men and women ≥18 and ≤69 years old; (2) generally healthy, yet meeting criteria; (3) Score ≥8 points on the Purify Readiness Scale—Table 5; (4) willingness to make required lifestyle changes during study participation; and (5) ability to understand and the willingness to sign a written informed consent document.

Exclusion criteria: (1) change in prescription medications, over-the-counter medications, medical foods, and nutritional supplements within 30 days prior to Day 1 and for the duration of the study; (2) use of medications classified as narcotics 15 days prior to Day 1 and for the duration of the study; (3) use of prescription medications and/or over-the-counter medications (Acetaminophen permitted) for acute and semi-acute medical conditions 15 days prior to Day 1 and for the duration of the study (use of acetaminophen was permitted on an as-needed basis); (4) use of an investigational drug or participation in an investigational study within 30 days prior to Day 1 and for the duration of the study; (5) use of oral or injectable corticosteroids within 30 days prior to Day 1 and for the duration of the study; (6) use of anticoagulant medications (heparin compounds, platelet inhibitors or warfarin) within 30 days prior to Day 1 and for the duration of the study (use of aspirin 81 mg or 325 mg once daily is permitted); (7) use of neuro-active prescription medications including major and atypical antipsychotic medications, anti-depressants, anti-anxiolytics, and epilepsy medications within 30 days prior to Day 1 and for the duration of the study; (8) use of prescription medications, over-the-counter medications, medical foods, and nutritional supplements for the treatment of hyperlipidemia within 30 days prior to Day 1 and for the duration of the study: and (9) use of prescription medications, over-the-counter medications, medical foods, and nutritional supplements for the treatment of hyperglycemia within 30 days prior to Day 1 and for the duration of the study.

Medical History and Concurrent Diseases: Subjects were not allowed to discontinue prohibited prescription medications, over-the-counter medications, medical foods, and nutritional supplements to meet enrollment criteria. Exclusionary criteria relating to medical history included: (1) a history of allergy or intolerance to study products; (2) clinically significant vital sign abnormalities (systolic blood pressure <90 mm Hg or >160 mm Hg, diastolic blood pressure <50 mm Hg or >100 mm Hg or resting heart rate of <50 or >100 bpm) at Screening; (3) a serious, unstable illness including cardiac, hepatic, renal, gastrointestinal, respiratory, endocrinologic, neurologic, immunologic, or hematologic disease; (4) known infection with HIV, TB or Hepatitis B or C; and (5) a current diagnosis or personal history of: (i) any cardiovascular disease including myocardial infarction, angina, cardiovascular surgery, congestive heart failure, cardiac arrhythmias or conduction abnormalities, cerebrovascular accident, transient ischemic attack (TIA), or peripheral vascular disease, deep vein thrombosis, or pulmonary embolus; (ii) type 1 or type 2 Diabetes Mellitus; (iii) any autoimmune disease such as inflammatory bowel disease (including Crohn's Disease and/or ulcerative colitis), multiple sclerosis, rheumatoid arthritis, systemic lupus erythematosus, polymyositis, scleroderma and/or thyroiditis; (iv) any significant liver or kidney disease such as cirrhosis or non-alcoholic fatty liver disease, glomerulonephritis, and/or ongoing dialysis treatment; (v) any malignancy (with the exception of basal or squamous cell carcinoma of the skin if adequately treated and no recurrence for >5 years); (vi) any serious mental illness including a history of attempted suicide.

Substance Use: Exclusionary substance use included: (1) use of drugs of abuse (such as marijuana, cocaine, phencyclidine [PCP], and methamphetamine) 15 days prior to Day 1 and for the duration of the study; or (2) history of regular intake of >14 alcoholic drinks per week for females, and >21 drinks per week for males (1 drink=12 oz. beer, 4 oz. wine, or 1.0 oz. hard liquor).

Other Exclusionary Criteria: (1) inability to comply with study and/or follow-up visits; (2) any concurrent condition (including clinically significant abnormalities in medical history, physical examination or laboratory evaluations) which, in the opinion of the PI, would preclude safe participation in this study or interfere with compliance; (3) any sound medical, psychiatric and/or social reason which, in the opinion of the PI, would preclude safe participation in this study or interfere with compliance; and (4) abnormal laboratory findings including: Abnormal blood counts (Hematocrit≤33% or >47%; WBC<3.0 or >12.0×103/mm3; platelets<140 or >500×109/L); abnormal kidney function test(s) (BUN>30 mg/dL or creatinine>1.5 mg/dL) or liver function test(s) (AST, ALT)>3× the upper limit of normal; serum calcium (≥11 mg/dL); serum K≤3.5 mEq/L; Na≤134 or ≥148 mEq/L.

Data Collection at Baseline, Week 1, Week 2 and Week 4: (i) vital signs (including blood pressure and heart rate), (ii) Physical Measurements (Weight and Waist Circumference), (iii) Body Impedance Analysis and Metabolic age, (iv) Clinical assessment (completion of Visit questionnaire, Gastrointestinal Quality of Life questionnaire w/ Bristol Stool Chart Scores, Food Plan Compliance questionnaire, MOS-SF 36 questionnaire, Medical Symptoms Questionnaire and visit with study clinician), (v) nitric oxide strip tests; subjects received instruction in measuring technique and were asked to obtain data the day after their first visit before beginning study therapies (vi) urine pregnancy test for women of child bearing potential, (vii) fasting phlebotomy for Complete Blood Count, Complete Metabolic Profile, gamma-glutamyl transferase (GGT), high sensitivity C-reactive protein (hs-CRP), lipopolysaccharide binding protein (LBP), myeloperoxidase (MPO), total branch chain amino acids, asymmetric dimethylarginine (ADMA), chlorophyllin, metallothioneine protein, and serum zonulin, (viii) urine collection for 24-hour Lactulose/Mannitol (L/M) ratio and toxic elements, (ix) Stool collection for fecal zonulin, fecal calprotectin, short-chain fatty acids (SCFAs) including n-butyrate, propionate and acetate, and (x) 2 mL plasma sample for repeat analyses and additional assays to further define safety, tolerability and acceptability.

Clinical Assays: CMPs were performed at Quest Diagnostics, 500 Plaza Drive, Secaucus, NJ 07094; and urine heavy metal assays were performed at Dr. Data, 3755 Illinois Avenue, St. Charles, IL 60174-2420: zonulin (fecal and serum) and fecal calprotecin were performed at Salveo Diagnostics, 4355 Innslake Drive, Glen Allen, VA.

Assay of Nitrite in Saliva: Salivary NO strips, which detect salivary $NO_2$ as a biomarker for NO, have been shown to be useful as a reliable indicator of physiological NO levels. Nitric Oxide Test Strips (Berkeley Test, Berkeley, CA) were used in this study to measure the appearance of the NO biomarker $NO_2$ in saliva. Subjects recorded morning, lunch and dinner strip scores 1 hour post meal-time once per week on the day of the clinical visit.

Lipopolysaccharide Binding Protein Assay: The lipopolysaccharide binding protein assay was performed using the R&D Systems (Minneapolis, MN) Magnetic Luminex Assay Kit (2-plex) according to instructions supplied with the kit.

Assay of Serum Arginine, Leucine, Isoleucine, and Valine: Amino acid standards, fluorenylmethyloxycarbonyl chloride (FMOC-Cl), potassium chloride (KCl), sodium hydroxide (NaOH), 1-adamantanamine HCl (ADAM), and boric acid were purchased from Sigma (Catalog #A9906, 23186, 793590, S318 and B7901, St. Louis, Mo.); ammonium formate, ammonium hydroxide, hydrochloric acid, and acetonitrile (AcN) were purchased from Fisher Scientific (Catalog #A11550, A470, A144SI, 153818 and A955, Hanover Park, IL); L-leucine-5,5,5-d3 (Leu-d3) was purchased from Cambridge Isotope Laboratory (Catalog #DLM-1259-1, Tewksbury, MA).

Clinical samples: Blood samples were collected in to K2-EDTA blood collection tubes at baseline, 1-, 2- and 4-week. Plasma was separated by centrifuging at 3000 rpm for 15 minutes, aliquoted and kept at −80° C. until use.

Sample preparation: Briefly, 10 µl plasma sample or amino acid calibration solution was added to 300 µl 50% AcN containing 1 µg/ml Leu-d3, followed by the addition of 150 µl borate buffer (0.4M, in 0.4M KCl solution, pH adjusted to 9 with NaOH solution), and 150 µl 20 mM FMOC-Cl AcN solution. The solution was mixed well and allowed to react at room temperature for 20 min. The reaction was stopped by adding 50 µl ADMA solution containing 50% AcN and 0.2 N HCl. The sample was further diluted with 600 µl AcN and the reaction mixture was centrifuged at 4000 rpm for 20 min. The supernatant was transferred to a 96-well sample plate for LC-MS analysis.

Chromatography: The system was a Waters Acuity I Class UPLC consisting of a binary pump, an autosampler, a column manager, and a Waters Xevo G2XS QTOF equipped with an ESI source (Waters Corp., Milford, MA) used as the detector. Accucore C18 bonded phase column (2.6 µm, 100 mm×2.1 mm, Thermo Fisher Scientific, Inc., Waltham, MA) was used, with mobile phase solvents (A) 2 mM ammonium formate, pH=9.5, and (B) AcN. One microliter samples were injected onto the column. Gradient elution was performed at 40° C.: 0-0.5 min, 95% A and 5% B; 0.5-5 min, linear gradient from 5 to 50% B; 5-5.1 min, linear gradient from 50 to 95% B; 5.1-7 min, held at 95% B; 7-7.1 min, B went back to 5%, and then held for 1 min. The flow rate was held at 0.6 ml/min. The ESI source was operated at negative sensitivity mode, with a capillary voltage of 0.8 kV, cone voltage 40V, source offset 80V, source temperature 120° C., desolvation temperature 550° C., cone gas flow 100 L/h and desolvation gas flow 1000 L/h. Leu-enkephalin was used as the lockspray reference. The branched chain amino acids valine, leucine and isoleucine were monitored at m/z values: 116.09, 130.08 and 130.08, respectively, and Leu-d3 as internal standard at 133.10. Arginine was monitored at m/z value 173.10 and Leu-d3 as internal standard at m/z 133.10.

Calculations: The amounts of arginine, leucine, isoleucine, and valine in the samples were calculated from respective calibration curves. The calculated concentrations were presented as µM in plasma.

Sodium Copper Chlorophyllin Assay: Cu (II) chlorin e4 disodium salt was purchased from Frontier Scientific (Catalog #41037, Logan, UT), reserpine was purchased from Sigma (Catalog #83580, St. Louis, Mo.); formic acid, ammonium formate, chloroform, methanol and isopropanol were purchased from Fisher Scientific (Catalog #A117, A11550, C607, A456 and A464, Hanover Park, IL).

Sample preparation: Briefly, 100 µl 0.1M ammonium formate solution (pH=4.0) was added to 100 µl serum or standard sample, followed by the addition of 600 µl of methanol:chloroform=1:1 (v/v) containing 0.5 ng/ml reserpine. The mixture was mixed well by vortex, and centrifuged at 13,000 rpm for 2 min. The lower phase was transferred to a glass vial and dried under a gentle stream of argon. The analytes were resuspended in 100 µl methanol and transferred to a LC-MS sample vial. Another 67 µl of water was added to the sample vial before the LC-MS analysis.

Chromatography: The system was a Waters Acuity I Class UPLC consisting of a binary pump, an autosampler, a column manager, and a Waters Xevo G2XS QTOF equipped with an ESI source (Waters Corp., Milford, MA) used as the detector. Accucore C18 bonded phase column (2.6 µm, 100 mm×2.1 mm, Thermo Fisher Scientific, Inc., Waltham, MA) was used, with mobile phase solvents (A) 2 mM ammonium formate and 0.1% formic acid in methanol:water=1:1 (v/v), and (B) 2 mM ammonium formate and 0.1% formic acid in methanol:isopropanol=1:1 (v/v). Nine microliters samples were injected on to the column. Gradient elution was performed at 55° C.: 0-0.5 min, 100% A and 0% B; 0.5-2 min, linear gradient from 0 to 15% B; 2-3 min, linear gradient from 15 to 60% B; 3-5 min, linear gradient from 60 to 80% B; 5-5.5 min, linear gradient from 80 to 95% B; 5.5-6.5 min, held at 95% B; 6.5-7 min, B went back to 0%, and then held for 1 min. The flow rate was held at 0.6 ml/min. The ESI source was operated at positive sensitivity mode, with a capillary voltage of 1.8 kV, cone voltage 60V, source offset 80V, source temperature 150° C., desolvation temperature 650° C., cone gas flow 160 L/h and desolvation gas flow 600 L/h. Leu-enkephalin was used as the lockspray reference. The analytes copper chlorin e6, copper chlorin e4 and copper chlorin e4 ethyl ester were monitored at m/z values: 657.18, 613.19 and 642.22, respectively, and reserpine as internal standard at m/z 609.28.

Calculations: Calibration curve of copper chlorin e4 was used to estimate the amount of copper chlorin e6, copper chlorin e4 and copper chlorin e4 ethyl ester in the sample. The calculated concentrations were expressed in ng/ml serum. Copper chlorin e6 was below detectable levels (<5 ng/ml). Total copper chlorophyllin was calculated by combining copper chlorin e4 and copper chlorin e4 ethyl ester.

Metallothionein (MT) Assay: Plasma MT concentrations were determined by enzyme-linked immunosorbent assay using commercially available sandwich ELISA kits (Cat #LS-F10296; LifeSpan Biosciences, Inc. Seattle, WA).

Results

Subject engagement: Of the 99 subjects screened for the study, 38 were selected (FIG. 3). Those 61 volunteers that were rejected either did not score ≥8 on the PRS, meet the inclusion criteria or declined to participate due to anticipated scheduling conflicts. One subject exited the study by week 4. Through phone calls it was determined that this subject had discontinued for personal reasons unrelated to the study. Overall 37 subjects completed the study—97% completion.

All statistical analysis was performed on an intent-to-treat basis and missing data were estimated by last visit forward.

Figure 4A:
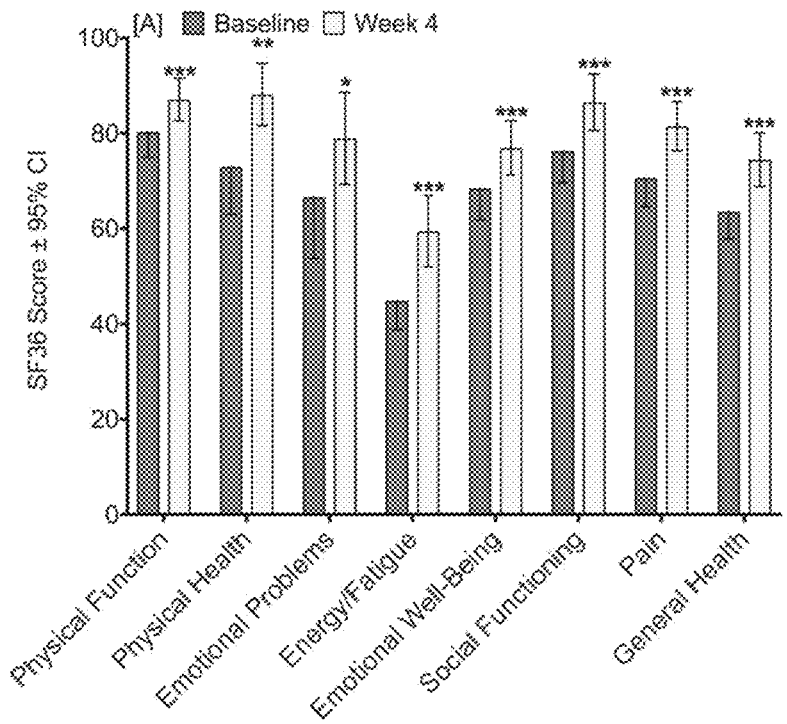
FIG. 4A is a graph displaying the mean scores±95% confidence intervals for the 8 categories of the 36-Item Short Form Health Survey (SF36) over the 4-week trial for N=38 subjects. *$P<0.05$; **$P<0.01$.
Figure 4B:
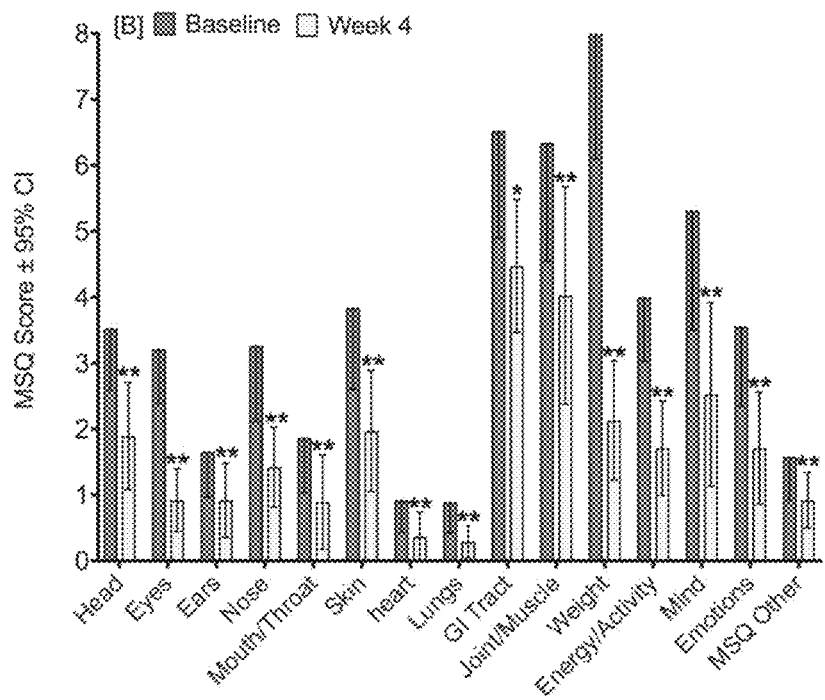
FIG. 4B graphically displays the mean scores±95% confidence intervals for the 15 domains of the Medical Screening Questionnaire over the 4-week trial for N=38 subjects. *$P<0.05$; **$P<0.01$.

Subjective Assessment of Health: The Short Form (36) Health Survey (SF-36) of subjective assessment of health was used to provide a quantitative representation of subject health over the course of the study. The SF-36 form consists of eight scaled scores, which are the weighted sums of the questions in their section. Each parameter is directly transformed into a 0-100 scale on the assumption that each question carries equal weight. The lower the score, the more disability. The higher the score the less disability i.e., a score of zero is equivalent to maximum disability and a score of 100 is equivalent to no disability. The eight sections are: (i) general health, (ii) physical functioning, (iii) physical health, (iv) emotional problems, (v) energy/fatigue or vitality, (vi) pain, (vii) emotional well-being, and (viii) social functioning. Subjects reported a significant trend toward improvement (P<0.01) in all eight categories of health in the SF-36 questionnaire and all 15 domains of the Medical Screening Questionnaire (MSQ) with no serious adverse events (FIGS. 4A and 4B, respectively).

Anthropometric Variables: BMI (1.8%, 2.7%, and 4.2%, respectively, for weeks 1, 2 and 4), body fat mass (2.2%, 3.5%, and 9.0%), visceral fat (2.7%, 5.1%, and 9.3%), and waist circumference (0.88%, 1.8%, and 3.1%), were all significantly reduced from baseline by week 1 with continued decreases through week 4. Waist/Hip ratio and metabolic age decreased, respectively, 1.0% and 4.2% at week 2 followed by decreases of 1.8% and 9.6% at week 4. Percent body fat decreased 5.0% only at week 4. Muscle and bone mass decreased similarly at weeks 1, respectively, 1.7% and 1.9% with 2.2% for both at week 2, while returning to baseline at week 4 (Table 11).

Lipid Biomarkers: At week 1, total cholesterol, LDL cholesterol, and triglycerides were decreased 11, 11 and 25%, respectively, 15, 17, and 24% at week 2 and 14, 15, and 25% at week 4. HDL cholesterol was reduced 4% relative to baseline only at week 4. The lipid ratios total cholesterol/HDL, LDL/HDL and TG/HDL were all decreased at all sampling times relative to baseline, respectively, 9.0, 9.7, and 23% at 1 week, 12, 14, and 20% at week 2, and 9.5, 11 and 19% at week 4 (Table 11).

Glycemic Biomarkers: Glucose, insulin, and HOMA-IR were all reduced at week 1, respectively, 8.6%, 20%, and 26%. Through week 4, all three variables retained those differences from baseline. The branch chain amino acids leucine, isoleucine and valine were elevated from baseline 18%, 21%, and 17% at week 1 and returned to baseline at 2 and 4 weeks (Table 11).

Vascular Biomarkers: Decreases in systolic blood pressure of 5.7%, 6.2%, and 6.4% were noted at weeks 1, 2 and 4, respectively. Diastolic blood pressure showed nonsignificant, graded decreases at weeks 1 and 2, which at 5.6% became significant at week 4. The mean % change in $NO_2$ salivary strip scoring following consumption of BiomeNO+ was elevated from baseline only at weeks 2 and 4 for the AM scoring, 54% and 44% respectively, while the afternoon mean % change was elevated 30% only at week 2 (Table 11). Serum arginine increased 21% at week 4 and the arginine/asymmetric dimethylarginine ratio was increased in concert with decreases in blood pressure, but with statistical significance achieved only at week 4.

Cardiovascular Risk: The percentage of subjects meeting diagnostic criteria for cardiometabolic syndrome dropped 26% in week 1 relative to baseline and remained at that level through 4 weeks. The decrease in 10-year cardiovascular risk based on lipids was 22% at 1 week and remained at that level at weeks 2 and 4, respectively, 26% and 23% (Table 11).

TABLE 11

| Percent change from baseline for anthropometric and metabolic variables | | | |
|---|---|---|---|
| Variable† | Week 1 (N = 38) | Week 2 (N = 38) | Week 4 (N = 38) |
| Anthropometric | | | |
| BMI (kg/m2) | −1.78*** | −2.69*** | −4.19*** |
| | (−2.13 to −1.42) | (−3.22 to −2.16) | (−4.93 to −3.46) |
| Body fat mass (kg) | −2.16*** | −3.46*** | −9.00*** |
| | (−3.3 to −1.01) | (−5.31 to −1.61) | (−10.7 to −7.26) |
| Body Fat (%) | −0.374 | −0.790 | −5.02*** |
| | (−1.59 to 0.844) | (−2.61 to 1.03) | (−6.68 to −3.36) |
| Visceral Fat (%) | −2.66* | −5.06*** | −9.33*** |
| | (−4.69 to −0.625) | (−7.78 to −2.33) | (−11.6 to −7.04) |
| Waist Circumference (cm) | −0.881* | −1.84*** | −3.09*** |
| | (−1.75 to −0.0147) | (−2.54 to −1.13) | (−4.16 to −2.02) |
| Waist/Hip | −0.881 | −1.01** | −1.82*** |
| | (−1.75 to −0.0147) | (−1.68 to −0.353) | (−2.84 to −0.794) |
| Muscle Mass (kg) | −1.67*** | −2.15*** | −1.16 |
| | (−2.59 to −0.743) | (−3.34 to −0.955) | (−2.51 to 0.178) |
| Bone Mass (kg) | −1.91*** | −2.17*** | −1.22 |
| | (−2.97 to −0.843) | (−3.35 to −0.993) | (−2.57 to 0.131) |
| Metabolic Age (yrs) | −2.27 | −4.19** | −9.60*** |
| | (−5.86 to 1.31) | (−6.57 to −1.82) | (−12.3 to −6.94) |
| Lipids | | | |
| Total Cholesterol (mg/dL) | −10.6*** | −14.9*** | −13.8*** |
| | (−14.2 to −6.91) | (−18.9 to −10.9) | (−18 to −9.69) |
| LDL Cholesterol (mg/dL) | −11.2*** | −16.8*** | −15.0*** |
| | (−17.2 to −5.21) | (−22.8 to −10.8) | (−21.2 to −8.78) |
| HDL Cholesterol (mg/dL) | −1.21 | −2.76 | −4.04* |
| | (−4.3 to 1.88) | (−6.46 to 0.943) | (−7.8 to −0.285) |
| Triglycerides (mg/dL) | −24.6*** | −23.9*** | −24.8*** |
| | (−32.6 to −16.6) | (−32.1 to −15.8) | (−33.4 to −16.2) |
| TC/HDL | −8.99*** | −11.7*** | −9.51*** |
| | (−12.8 to −5.13) | (−16.1 to −7.33) | (−13.9 to −5.11) |
| LDL · HDL | −9.68** | −13.7*** | −10.5** |
| | (−15.8 to −3.6) | (−20.1 to −7.29) | (−16.8 to −4.27) |
| TG/HDL | −22.5*** | −20.0*** | −19.3*** |
| | (−31.1 to −13.9) | (−29.5 to −10.6) | (−30 to −8.55) |
| Insulin Functioning | | | |
| Glucose (mg/dL) | −8.61*** | −6.21*** | −4.35** |
| | (−11.8 to −5.45) | (−9.72 to −2.69) | (−7.27 to −1.44) |
| Insulin (μIU/mL) | −20.1* | −20.8* | −24.5** |
| | (−36.4 to −3.76) | (−37.4 to −4.14) | (−38.6 to −10.3) |
| HOMA-IR (units) | −25.6** | −23.4* | −25.9** |
| | (−41.5 to −9.71) | (−41.4 to −5.51) | (−40.7 to −11) |
| Leucine (μM) | 18.4*** | 3.67 | −2.1 |
| | (9.14 to 27.6) | (−3.04 to 10.4) | (−7.68 to 3.49) |
| Isoleucine (μM) | 21.1*** | 4.56 | −0.199 |
| | (9.69 to 32.6) | (−3.48 to 12.6) | (−7.71 to 7.31) |
| Valine (μM) | 17.2** | 9.25 | 5.86 |
| | (7.43 to 26.9) | (−0.923 to 19.4) | (−2.9 to 14.6) |
| Vascular Biomarkers | | | |
| Systolic BP (mm Hg) | −5.74*** | −6.22*** | −6.35*** |
| | (−8.17 to −3.32) | (−8.85 to −3.59) | (−9.35 to −3.35) |
| Diastolic BP (mm Hg) | −2.79* | −3.03 | −5.60** |
| | (−5.39 to −0.188) | (−6.41 to 0.357) | (−8.88 to −2.32) |
| Salivary Nitrite (AM Ratio) | 61.4 | 54.0*** | 43.6*** |
| | (−19.4 to 142) | (24.1 to 83.9) | (17.9 to 69.4) |
| Salivary Nitrite (PM Ratio) | 12.1 | 29.7** | 42.5 |
| | (−7.44 to 31.6) | (9.75 to 49.7) | (−11.2 to 96.3) |
| Arginine (μM) | 3.11 | 1.5 | 20.6* |
| | (−10.4 to 16.6) | (−13.4 to 16.4) | (0.593 to 40.5) |
| Asymmetric dimethylarginine (μM) | −3.21 | −8.27*** | −5.00*** |
| | (−7.27 to 0.841) | (−11.1 to −5.45) | (−7.87 to −2.13) |
| Arg/ADMA | 5.20 | 11.3 | 27.5* |
| | (−5.26 to 15.7) | (−6.03 to 28.7) | (5.79 to 49.3) |
| Cardiovascular Risk (CR) | | | |
| Metabolic Syndrome Criteria (%) | −25.9*** | −23.4*** | −26.0*** |
| | (−37.1 to −14.8} | (−36.2 to −10.6) | (−39.5 to −12.6) |
| 10-Year Cardiac Risk/Lipids (%) | −21.6*** | −25.7*** | −22.9*** |
| | (−27.8 to −15.3) | (−32.2 to −19.2) | (−31.4 to −14.5) |

TABLE 11-continued

Percent change from baseline for anthropometric and metabolic variables

| Variable† | Week 1 (N = 38) | Week 2 (N = 38) | Week 4 (N = 38) |
|---|---|---|---|
| Inflammation/Oxidative Stress | | | |
| Myeloperoxidase (MPO) | −3.08 (−7.68 to 1.52) | −5.72* (−10.7 to −0.703) | −2.71 (−8.24 to 2.81) |
| Chlorophyllin (nM) | 4807*** (2536 to 7078) | 8494*** (3192 to 13795) | 6266*** (3014 to 9517) |
| Liver/Detoxification Functioning | | | |
| Fatty Liver Index (Score) | −12.0*** (−17.5 to −6.55) | −15.9*** (−21.5 to −10.3) | −21.1*** (−27 to −15.3) |
| GGT (IU/L) | −4.03 (−9.54 to 1.49) | −11.9*** (−18.4 to −5.48) | −16.9*** (−25.6 to −8.13) |
| AST (U/L) | 15.0** (5.16 to 24.8) | 11.7* (1.9 to 21.4) | 16.0* (1.64 to 30.4) |
| ALT (U/L) | 8.43 (−1.03 to 17.9) | 10.2 (−3.31 to 23.7) | 19.3 (−6.63 to 45.3) |
| AST/ALT | 7.30* (0.758 to 13.9) | 5.41 (−1.33 to 12.2) | 7.02 (−1.13 to 15.2) |
| AKP (U/L) | −4.49** (−7.08 to −1.90) | −3.65** (−5.84 to −1.45) | −4.13** (−7.15 to −1.11) |
| Bilirubin (mg/dL) | 9.78* (0.810 to 18.6) | 2.93 (−6.18 to 12.0) | 11.3* (1.12 to 21.5) |
| Albumin (g/dL) | 3.78*** (2.32 to 5.24) | 6.17*** (4.64 to 7.7) | 1.90* (0.448 to 3.37) |
| Total Protein (g/dL) | 0.630 (−0.679 to 1.94) | 1.01 (−0.0219 to 2.04) | 0.905 (−0.403 to 2.21) |
| Globulin (g/dL) | −4.24** (−6.68 to −1.80) | −6.96*** (−8.62 to −5.29) | −0.657 (−2.81 to 1.5) |
| A/G | 8.81*** (5.55 to 12.1) | 14.0*** (10.8 to 17.1) | 2.70* (0.120 to 5.27) |
| Metallothionein (pg/mL) | 17.7*** (10.9 to 24.5) | 11.7*** (5.48 to 17.9) | 5.66 (−1.22 to 12.5) |

AKP: Alkaline phosphatase; ALT = Alanine transaminase, AST = Aspartate aminotransferase, BMI: Body Mass Index; BP: Blood Pressure; GGT: Gamma-glutamyltransferase.
†Values are means with parenthetic 95% confidence intervals; differences from baseline determined by t-test
* = $P < 0.05$,
** = $P < 0.01$,
*** = $P < 0.001$ Inflammation/Oxidative Stress: MPO exhibited a decrease from baseline of 5.7% at week 2 and slight, nonsignificant decreases of 3.1% and 2.7% at weeks 1 and 4. Dramatic increases of 4807%, 8494%, and 6266% at weeks 1, 2, and 4 were noted for chlophyllin (Table 11).

Liver Functioning and Detoxification: A graded decrease of 12%, 16%, and 21% (P<0.001 for all 3 weeks) was observed for the fatty liver index (FLI) over weeks 1, 2, and 4. These decreases were paralleled by those seen for GGT of 4.0%, 12%, and 17% (P<0.001 for weeks 2 and 4). AST was elevated within the normal range at all 3 sampling times, while ALT was not changed from baseline throughout the study. The AST/ALT ratio was elevated 7.3% within the normal range at week 1 and returned to baseline at 2 and 4 weeks. AKP was reduced 4.4%, 3.7%, and 4.1% with P<0.01) at all sampling times. The increases in bilirubin of 9.8% and 11% noted at weeks 1 and 4, respectively, reflected values within the normal range. No change from baseline was seen for total protein, while albumin was elevated 3.8%, 6.2%, and 1.9% at 1, 2 and 4 weeks. Globulin decreased 4.2% and 7.0% at weeks 1 and 2 resulting in an increase in the A/G ratio of 8.8%, 14%, and 2.7% at weeks 1, 2 and 4, respectively. Serum metallothionein increased above baseline at weeks 1 and 2, respectively, 18% and 12% and returned to baseline at week 4.

Urinary Heavy Metal Excretion: Fifteen of the 20 metals assayed were sufficiently above the limit of quantitation to provide an acceptable assessment of excretion. Of those 15 that were quantitated at all sampling periods, 10 exhibited an increased excretion from baseline (P<0.05) during the four weeks of the study (Table 12). Overnight urinary excretion of cadmium, gadolinium, mercury, thallium and uranium was elevated over baseline at all three sampling times. Increases in urinary excretion of antimony, bismuth and cesium were noted in weeks 1 and 2, while arsenic and barium urinary excretion was elevated from baseline only in week 4. Overall, thallium exhibited the highest, consistent increase from baseline ranging from 65% at week 1 to 76% at week 4 (P<0.05 for all three sampling points).

TABLE 12

Percent change from baseline for urinary heavy metal concentrations

| Variable | Week 1 (N = 37) | Week 2 (N = 37) | Week 4 (N = 37) |
|---|---|---|---|
| Aluminum | −1.69† | 11.1 | 4.47 |
|  | (−16.7 to 13.3) | (−18.7 to 40.9) | (−16.0 to 25) |
| Antimony | 20.1* | 19.2* | 77.2 |
|  | (4.81 to 35.4) | (4.37 to 34.1) | (−46.2 to 201) |
| Arsenic | 101 | 100 | 54.9** |
|  | (−7.28 to 209) | (−4.25 to 205) | (21.5 to 88.2) |
| Barium | 76.2 | 105 | 68.3* |
|  | (−38.9 to 191) | (−57.9 to 267) | (4.05 to 133) |
| Bismuth | 28.1** | 22.1* | 79.8 |
|  | (8.30 to 47.9) | (4.1 to 40.1) | (−51.8 to 211) |
| Cadmium | 20.5* | 32.2** | 31.2* |
|  | (1.85 to 39.2) | (10.4 to 54.1) | (85.2 to 59.6) |
| Cesium | 13.4* | 15.7* | 15.8 |
|  | (0.925 to 26.0)* | (0.0153 to 31.30) | (−1.27 to 32.9) |
| Gadolinium | 19.6** | 23.1** | 21.4** |
|  | (5.98 to 33.2) | (7.87 to 38.3) | (5.97 to 36.8) |
| Lead | 4.84 | 7.11 | 18.7 |
|  | (−5.60- to 15.3) | (−6.94 to 21.2) | (−7.61 to 45.1) |
| Mercury | 18.5* | 21.5* | 22.3** |
|  | (3.76 to 33.2) | (4.74 to 38.2) | (6.49 to 38.1) |
| Nickel | 3.58 | 7.75 | 22.2 |
|  | (−12.6 to 19.7) | (−8.14 to 23.6 | (−0.396 to 44.7) |
| Thallium | 64.9** | 62.8** | 75.6** |
|  | (36.3 to 93.5) | (32.4 to 93.2) | (35.0 to 116) |
| Tin | −3.74 | 1.64 | −1.90 |
|  | (−15.3 to 7.82) | (−10.9 to 14.2) | (−22.7 to 19.0) |
| Tungsten | −16.4 | −14.5 | −0.374 |
|  | (−40.9 to 8.00) | (−35.1 to 5.99) | (−27.4 to 26.7) |
| Uranium | 19.2** | 17.5* | 36.9* |
|  | (6.35 to 32.0) | (3.22 to 31.8) | (5.82 to 68.0) |

†Values are mean percent increase from baseline with 95% confidence intervals.
*p < 0.05 and
**p < 0.01 for difference from baseline as determined by paired t-test with N = 37.

Figure 5:
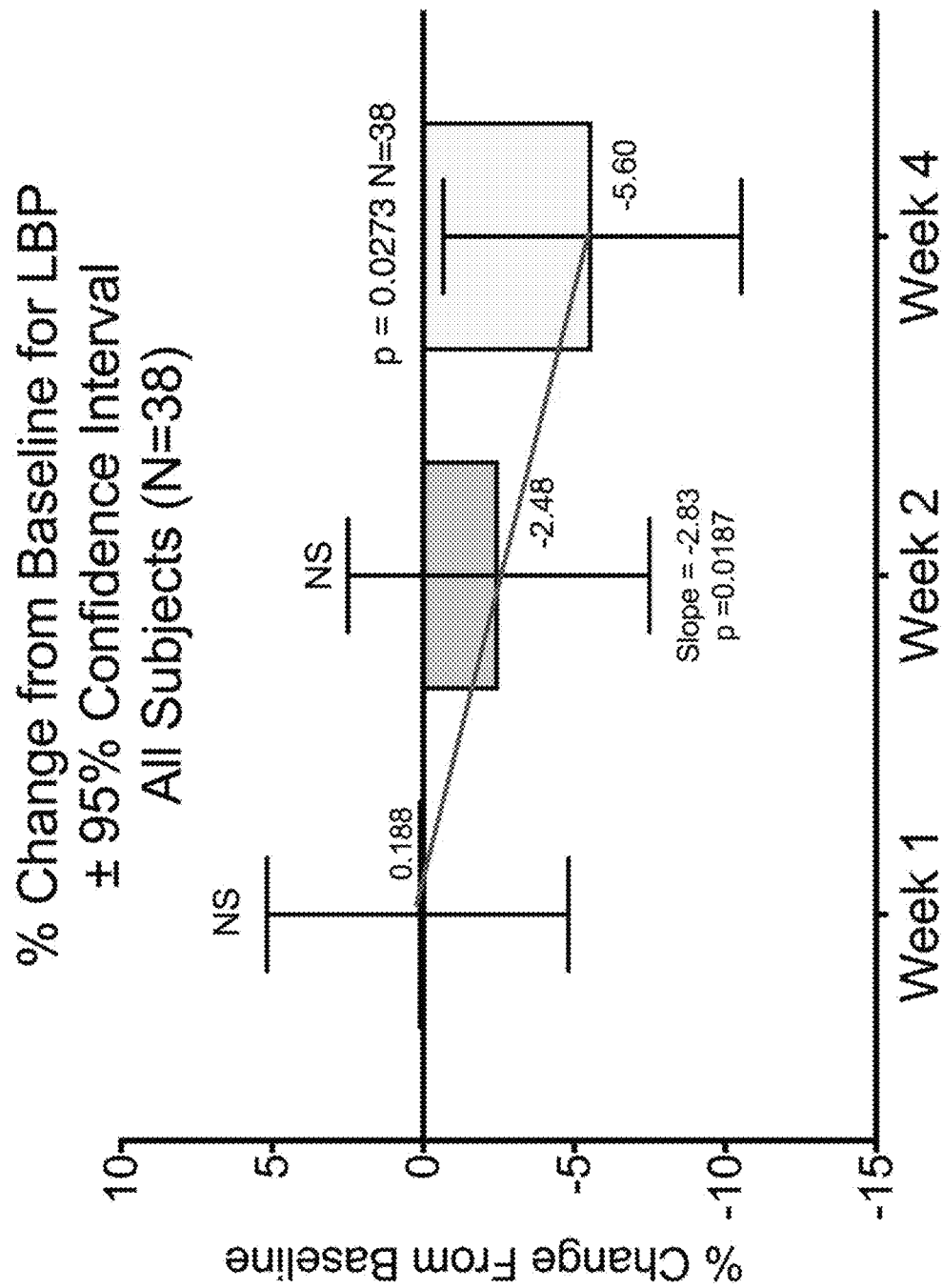
FIG. 5 is a graph displaying the mean percent change from baseline±95% confidence interval for lipopolysaccharide binding protein levels during weeks 1, 2 and 4 of the study.

Gut Functioning Biomarkers Serum Lipopolysaccharide Binding Protein, Fecal Zonulin, and Fecal Calprotectin: One of the most important crosstalks between gut microbiota and humans is recognized as 'endotoxemia', characterized by elevated circulating lipopolysaccharide (LPS), an endotoxin produced by Gram-negative bacteria. Intravenous infusion of LPS can induce systemic insulin resistance and elevation of inflammatory markers in adipose tissue. However, owing to its short half-life and interference in the blood, it is difficult to measure circulating LPS in large-scale population-based studies or clinical trials. By contrast, lipopolysaccharide binding protein (LBP), which is mainly synthesized in the liver, could specifically bind to and monomerize exogenous LPS, thereafter enabling the endotoxin to be recognized by Toll-like receptor 4 (TLR4) and cluster of differentiation 14 (CD14), which are responsible for consequent innate immunity. Therefore, circulating LBP levels, with a relatively long half-life, can be used as a variable to assess endotoxemia status and its immune responses. In this example, the Purify program reduced LBP 2.48% at week 2 (P>0.05, N=38) and 5.60% at week 4 (P<0.027, N=38) with no significant decrease at week 1 (FIG. 5).

Figure 6A:
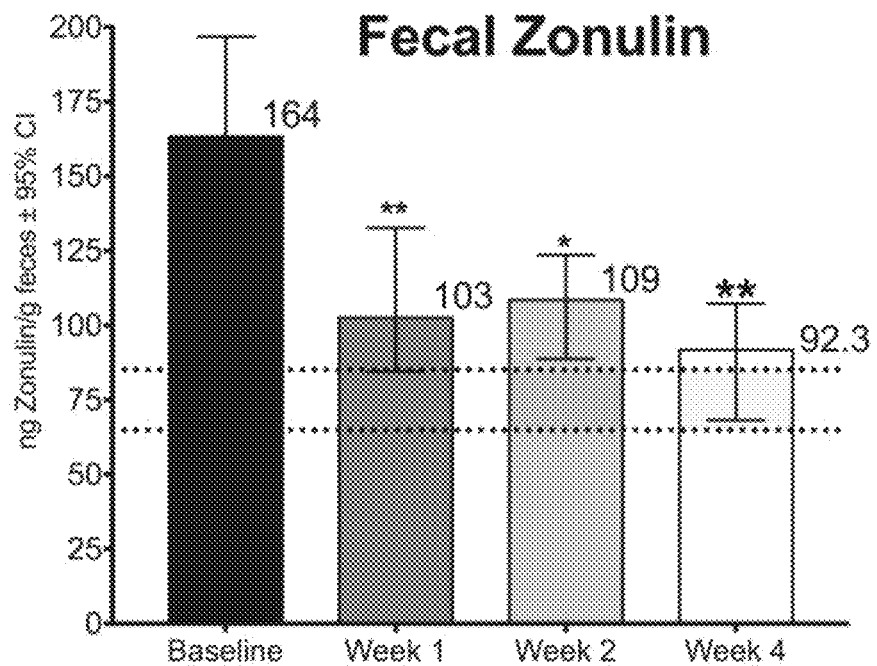
FIG. 6A is a graph illustrating the median±95% confidence intervals for fecal zonulin levels during weeks 1, 2 and 4 of the study.

Research to date has identified fecal zonulin as the only physiologically reversible regulator of the gut endothelial cell barrier. At baseline in this example, subjects exhibited elevated fecal zonulin (>85.1 ng zonulin/g feces) that was reduced by 37% at week 1 (P<0.05) and continued to decrease over the 4 weeks of the study (P<0.001 for trend; FIG. 6A). Serum zonulin, however, did not change with a nonsignificant (P>0.05) 2.0% (95% CI—12 to 16%) increase over baseline by week 4 (data not shown). Unlike fecal zonulin, serum zonulin can also reflect its release from other tissues such as lung and brain. Thus, fecal zonulin is a more selective biomarker of impaired gut barrier function and these results demonstrate rapid (within one week) and continued improvement of gut permeability through the 4 weeks of the study.

Calprotectin is a small calcium- and zinc-binding protein that derives mainly from neutrophils, constituting 60% of the cytosolic protein. Active inflammation in the gut that induces neutrophil influx into the mucosa will eventually disrupt the mucosal architecture, allowing neutrophils (with their cytosolic calprotectin) to leak into the intestinal lumen and be excreted with the feces. Fecal calprotectin correlates with the severity of intestinal inflammation, and is a sensitive biomarker of inflammatory bowel disease (IBD). Measurement of fecal calprotectin represents a reliable, accurate, and noninvasive method of detecting mucosal inflammation in the GI tract.

Figure 6B:
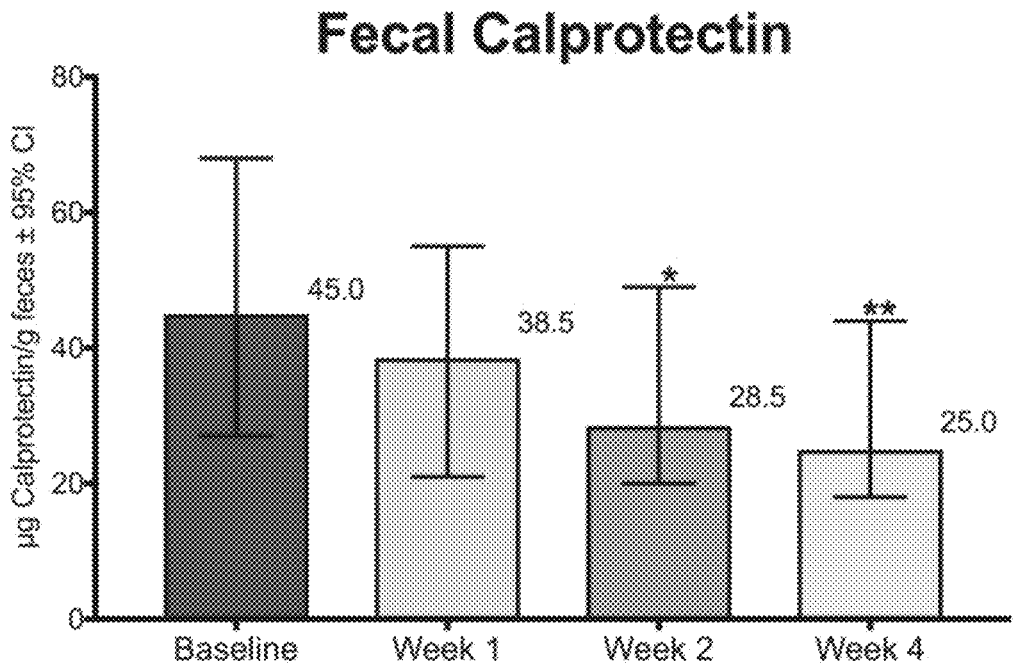
FIG. 6B is a graph illustrating the median±95% confidence intervals for fecal calprotectin levels during weeks 1, 2 and 4 of the study.

At baseline, subjects exhibited normal fecal calprotectin levels of <50 μg/g feces. While the 15% decrease observed in week 1 was not significant (P>0.05), the 37% and 44% decreases for weeks 2 and 4, respectively, were significant with P<0.05 and P<0.01 (FIG. 6B). These findings suggest a decrease in gut inflammation even in normal gut.

Figure 6C:
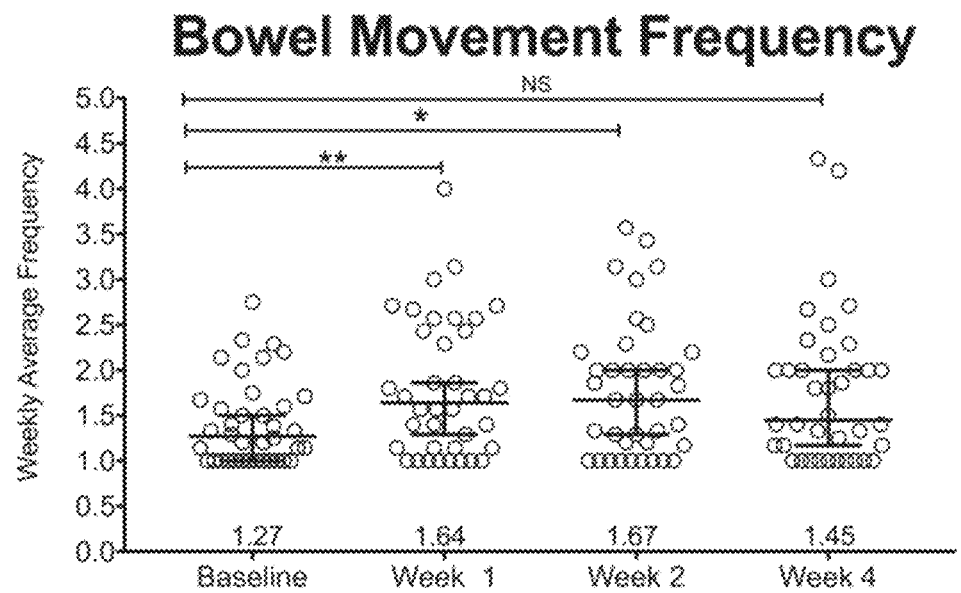
FIG. 6C is a graph illustrating the median±95% confidence intervals for weekly average bowel movement frequency during weeks 1, 2 and 4 of the study.

Bowel Movement Frequency and Form: The median number of bowel movements per day per subject increased slightly from baseline (1.27 per day) at weeks 1 (1.64 with P<0.01) and 2 (1.67 with P<0.05), but returned to baseline values at week 4 (1.48 per day with P>0.05) c,f, FIG. 6C.

The Bristol stool form scale represents a diagnostic medical tool designed to classify the form of human feces into seven categories. The seven types of stool are: Type 1: Separate hard lumps, like nuts (hard to pass); also known as goat feces; Type 2: Sausage-shaped, but lumpy; Type 3: Like a sausage but with cracks on its surface; Type 4: Like a sausage or snake, smooth and soft; Type 5: Soft blobs with clear cut edges (passed easily); Type 6: Fluffy pieces with ragged edges, a mushy stool; Type 7: Watery, no solid pieces, entirely liquid. Types 1 and 2 indicate constipation, with 3 and 4 being the ideal stools (especially the latter), as they are easy to defecate while not containing excess liquid, and 5, 6 and 7 tending towards diarrhea.

Figure 6D:
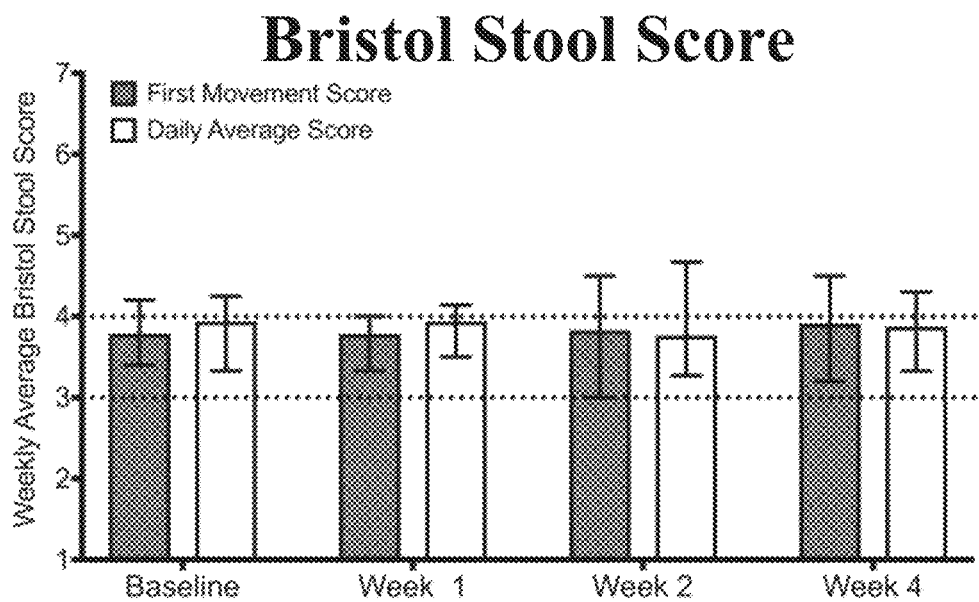
FIG. 6D is a graph illustrating the median±95% confidence intervals for weekly average Bristol Stool Score for first bowel movement and daily average bowel movements during weeks 1, 2 and 4 of the study.

Subjects were requested to score their stools daily using the standardized Bristol Stool Scale Scoring daily from 6 days prior to the start of the study and daily during the study. Median Bristol Scale scores and 95% confidence intervals were plotted (FIG. 6D) for all subjects (N=38). All median values for all four sampling times were not different from the ideal values of 3 to 4 as indicated by the dotted lines in the graph. Therefore, it can be concluded that the Purify program did not alter normal stool formation.

This example demonstrates the effectiveness and efficacy of the addition of a group of detoxification supplements to diet and lifestyle modifications for increased wellbeing, weight loss, improved cardiometabolic variables, liver functioning and enhanced intestinal patency.

Example 2—Evaluation of a Program (InForm1.1) for Healthy Weight and Cardiometabolic Function This trial was a randomized, two-arm, open-label study of diet and lifestyle modification (Arm A) against the same diet and lifestyle modification administered with a group of weight loss stimulating dietary supplements (Arm B) in generally healthy overweight subjects with cardiometabolic risk factors (See Table 13).

TABLE 13

Study Design Contrasting Arm A and Arm B in InForm1.1

| Activity | Details | |
|---|---|---|
| Recruiting and Screening | Recruit generally healthy, overweight and obese adults Measure waist, hip circumference, blood pressure, lipids and glucose. Randomize to an open-label, 2-arm study | |
| | Arm A | Arm B |
| Weeks 1-13 | High photonutrient protein rich food plan Physical activity Cognitive behavioral program | High photonutrient protein rich food plan Physical activity Cognitive behavioral program SNACK REPLACEMENT 40 g Protein 4 g Phytosterols 3 capsules Berberin-IR ® 2 capsules CardioxLDL ® (night) 2 capsules Probiotic 11 ® 2 softgels Super Omega-3 EPA ® 4 tablets Super Supplemental ® |

Volunteers were first screened to determine volunteer eligibility for study participation. Screening included a review and signing of the Screening Informed Consent form; measurement of height, weight, waist circumference and vital signs; completion of medical history questionnaire; review of medical history and current medications by clinician; and collection of fasting blood for testing of: Complete Blood Count (CBC), Comprehensive Metabolic Profile (CMP), standard lipid panel, insulin and hemoglobin A1c (HbA1c) as well as a pregnancy test in females of childbearing potential. Screening labs were performed within 8 weeks of beginning the trial. Fasting was defined as greater than 8 hours and less than 12 hours of refraining from consumption of food and beverages though unlimited consumption of water was allowed and encouraged. Upon review of screening data acceptable for inclusion, a telephone interview with a study investigator was completed to confirm eligibility, and document absence of contraindications to participation.

High phyto-nutrient protein rich food plan—Both Arms A and B were provided with information on a specific food plan to be followed through the 12-week study. The plan promoted achieving health goals by counting servings of food and not calories. The food plan ensures that the required number of servings each day provide a balanced blend of protein, carbohydrates and fat and that the subjects received a diet packed with vitamins, minerals and nutrients from plants. The plan encompassed five meals and snacks daily along with limiting sugars, refined carbohydrates, and grains to provide an estimated 1,635 calories per day. See Tables 14 and 15.

TABLE 14

Representative Diets† and Supplementation* Followed in A and B Arms

| A | B |
|---|---|
| Breakfast | |
| Eggs (2 large) Peppers (0.5 cup) Olive oil (1 tsp) | Eggs (2) Peppers (0.5 cup) Olive oil (1 tsp) Super Supplemental ® (2 tablets); Super Omega 3 EPA ® (1 capsule |

TABLE 14-continued

Representative Diets† and Supplementation* Followed in A and B Arms

| A | B |
|---|---|
| | containing 380 mg EPA, 190 mg DHA); Probiotic Eleven ® (1); Berberine IR ® (1capsule 333 mg) |

TABLE 14-continued

Representative Diets† and Supplementation*
Followed in A and B Arms

| A | B |
|---|---|
| \multicolumn{2}{c}{Snack} | |
| Mixed greens (2.5 oz) | Protein Supplement Shake (Soy, Pea, or Whey) |
| Olive oil (1 tsp) | Phytosterols (1 scoop 2 - g) |
| Almonds (16) | Mixed greens (2.5 oz) |
| Olives (6) | Olive oil (1 tsp) |
| \multicolumn{2}{c}{Lunch} | |
| Chicken breast (1 palm size) | Chicken breast (1 palm size) |
| Broccoli (2 cups) | Broccoli (2 cups) |
| Olive oil (1 tsp) | Olive oil (1 tsp) |
|  | Olives (6) |
|  | Berberine IR® (1capsule 333 mg) |
| \multicolumn{2}{c}{Snack} | |
| 1 Chicken leg (1) | Protein Supplement Shake (Soy, Pea, or Whey) |
| Apple (1, small) | Phytosterols (1 scoop - 2 g) |
| \multicolumn{2}{c}{Dinner} | |
| Turkey breast (1 palm sized) | Turkey breast (1 palm sized) |
| Bok choy (1 cup) | Bok choy (1 cup) |
| Carrots (0.5 cup) | Carrots (0.5 cup) |
| Mixed greens (2.5 oz) | Mixed greens (2.5 oz) |
| Olive oil (1 tsp) | Olive oil (1 tsp) |
| Cucumber (6 slices) | Cucumber (6 slices) |
| Avocado (⅛) | Avocado (⅛) |
|  | Super Supplemental ® (2 tablets); |
|  | Super Omega 3 EPA ® (1 capsule containing 380 mg EPA, 190 mg DHA); |
|  | Probiotic Eleven ® (1); Berberine IR ® (1capsule 333 mg); CardioxLDL ® (2 capsules) |
| \multicolumn{2}{c}{Beverages} | |
| \multicolumn{2}{c}{Water and Herbal teas: unlimited; coffee or tea (black, green, white): 1 cup caffeinated or decaffeinated} | |
| \multicolumn{2}{c}{Condiments/Sweeteners} | |
| \multicolumn{2}{c}{All fresh/dry herbs: dill, oregano, basil, lavender, tarragon, etc. All spices: cinnamon, chili powder, pepper, ginger, etc. Mustards, horseradish, lemon/lime juice, salsa, vinegars (all types) (unsweetened), soy sauce, fish sauce (unsweetened). Stevia.} | |

†Vegetables could be eaten raw or steamed and dressed with one of their fats as primary cooking method.
*Shaded areas denote differences between arms.

Moderate physical activity—All subjects received instruction and were required to follow the lifestyle change program consisting of the food plan (above) and exercise recommendations. The exercise requirements included (1) using a pedometer, (2) keeping a log of daily steps aiming for at least 5,000 steps per day (about 2.5 miles), with at least 30 minutes of moderate intensity focusing on aerobic movement exercising, and (3) adding resistance training and flexibility exercises at least twice a week.

Cognitive behavioral program—All subjects were required to attend weekly, short seminars on mindfulness and visualization techniques designed for stress reduction, relaxation and mind-body connectivity.

TABLE 15

Snack Replacement and Weight Loss Stimulating Supplements for Arm B Only

| PROG Supplementation | Daily Servings | Function |
|---|---|---|
| Snack Replacement | 2 scoops 2× | Amino acids/antioxidants |
| Weight Loss Stimulating Supplements | | |
| Phytosterols | 1 scoop 2× | Biomatrix enrichment |
| Berberine IR | 3 capsules at dinner | Antimicrobial |
| CardioxLDL ® | 2 capsules/dinner | Antioxidant |
| Probiotic 11 | 1 capsule 2× | Repairing dysbiosis |
| Super Omega-3 EPA | 1 capsule 2× | Anti-inflammatory |
| Super Supplemental Vitamins & Minerals and Minerals | 2 tablets 2× | Biomatrix enrichment |

Phytosterols—The phytosterol supplement was manufactured by Nature's Sunshine Products in Spanish Fork, Utah and contained 2000 mg phytosterols per serving.

Berberine IR®—The berberine IR supplement was manufactured by Nature's Sunshine Products in Spanish Fork, Utah. It contained: 333 mg berberine HCl. Subjects in Arm B were instructed to take 3 capsules per day at dinner (total=1 g berberine)

CardioxLDL—The cardiox LDL supplement was manufactured by Nature's Sunshine Products in Spanish Fork, Utah. It contained: blueberry fruit concentrate, apple fruit extract, capsicum fruit, bergamot orange fruit extract, grape seed extract, grape skin extract, green tea leaf extract (decaffeinated), olive leaf extract, turmeric root & rhizome extract, and mangosteen pericarp extract. Subjects were instructed to take two capsules per day with a meal.

Probiotic 11—The probiotic 11 supplement was manufactured by Nature's Sunshine Products in Spanish Fork, Utah. It contained: *Bifidobacterium bifidum, B. infantis, B. longum, Lactobacillus rhamnosus, L. acidophilus, L. bulgaricus, L. brevis, L. plantarum, L. salivarius, L. casei, Streptococcus thermophiles*, inulin, fructooligosaccharide, and prebiotic fibers. Subjects were instructed to take one capsule two times per day.

Super Omega-3 EPA—The super omega 3-EPA supplement was manufactured by Nature's Sunshine Products in Spanish Fork, Utah, it contained 360 mg eicosapentaenoic acid (EPA and 190 mg docosahexaenoic acid (DHA).

Super Supplemental Vitamins and Minerals—The super supplemental vitamin and mineral supplement was manufactured by Nature's Sunshine Products in Spanish Fork, Utah. It contained biotin, chromium amino acid chelate, copper gluconate, vitamin B12 (cyanocobalamin), cellulose, folic acid, magnesium amino acid chelate, manganese amino acid chelate, potassium iodide, vitamin B6 (pyridoxine hydrochloride), riboflavin (B2), selenium amino acid chelate, thiamin (B1) (thiamine mononitrate), vitamin A Palmitate, vitamin D3 (cholecalciferol), asparagus stem/*Asparagus officinalis*, acai berry/*Euterpe oleracea*, broccoli flowers/*Brassica oleracea*, carrot root/*Daucus carota*, cranberry fruit/*Vaccinium macrocarpon*, L-arginine, L-isoleucine, L-leucine, L-lysine, L-methionine, L-tyrosine, L-phenylalanine, L-threonine, L-valine, Pomegranate fruit extract/*Punica granatum*, fruit blend eight, spinach leaf & stem/*Spinacia oleracea*, tomato fruit *Solanum lycopersicum*, choline bitartrate, L-cysteine HCl [anhydrous], inositol, mangosteen fruit [freeze dried]/*Garcinia mangostana*, alfalfa aerial parts/*Medicago sativa*, cabbage leaf/*Brassica oleracea* var. *capitata*, kelp leaf & stem/*Ascophyllum nodo-* sum, *Laminaria digitata*, hesperidin bioflavonoid extract, cellulose, lemon bioflavonoid extract, magnesium stearate (vegetable), rose hips extract [4:1]/*Rosa canina*, rutin, dandelion root/*Taraxacum officinale*, lutein, cellulose [croscarmellose sodium, modified cellulose gum], dicalcium phosphate, vitamin C, beta-carotene, calcium amino acid chelate, pantothenic acid, calcium citrate, choline bitartrate, vitamin E (d-alpha tocopheryl acetate), ferrous fumarate, stearic acid (vegetable), inositol, lycopene, magnesium oxide, magnesium stearate (vegetable), niacinamide, para-aminobenzoic acid (PABA), potassium citrate, sodium copper chlorophyllin, silicon dioxide, and zinc gluconate.

High Protein, Low Glycemic Index Snack/Meal Formulation—Subjects in Arm B substituted 2 snacks with a snack/meal replacement formulation (MR). The meal replacement formulation provides a minimum of 40 g protein, about 6 to 10 g fat, about 32 g carbohydrate, about 4 g of phytosterols and about 360 calories per day (Table 16) and contained the following ingredients: ascorbic acid, biotin, *Chlorella/Chlorella vulgaris*, chromium nicotinate, copper citrate, D-calcium pantothenate, cyanocobalamin, flax seed/*Linum usitatissimum*, folic acid, fructooligosaccharide (fiber), magnesium oxide, manganese citrate, maltodextrin, medium chain triglycerides, natural vanilla flavor, niacinamide, non-dairy creamer (contains milk, soy), potassium citrate potassium iodide, riboflavin, sugar cane (*Saccharum officinarum*), sodium molybdate dihydrate, sodium selenate (selenium), stevia leaf extract/*Stevia rebaudiana*, thiamin HCl, tricalcium phosphate, vitamin a palmitate, vitamin D3, xanthan gum, zinc citrate, cellulose gum, guar gum, pyridoxine hydrochloride, salt, and vitamin E tocopherol.

TABLE 16

Snack/Meal Replacement Formulations (SR) Used in Arm B†

| Ingredient | SR1 | SR2 | SR3 | % Daily Value |
|---|---|---|---|---|
| Serving Size (g) | 46 | 45 | 45 | |
| Calories | 184 | 180 | 173 | |
| Fat (g) | 5 | 3 | 5 | |
| Saturated Fat (g) | 2 | 1 | 1 | |
| Trans Fat (g) | 0 | 0 | 0 | |
| Cholesterol (mg) | 32 | 0 | 0 | |
| Sodium (mg) | 104 | 150 | 307 | |
| Potassium (mg) | 368 | 95 | 187 | |
| Carbohydrate (g) | 14 | 16 | 16 | |
| Dietary Fiber (g) | 5 | 3 | 3 | |
| Sugars (g) | 5 | 9 | 8 | |
| Protein (g) | 20 | 20 | 20 | |
| Phytosterols (mg) | 2000 | 2000 | 2000 | * |
| Vitamin A (IU) | 48 | 75 | 47 | 35% |
| Vitamin C (mg) | 48 | 75 | 47 | 100% |
| Calcium (mg) | 96 | 2 | 33 | 60% |
| Iron (mg) | 0 | 0 | 0 | 20% |
| Vitamin A (IU) | 48 | 75 | 47 | 35% |
| Vitamin D (IU) | 0 | 75 | 47 | 10% |
| Vitamin E (IU) | 48 | 0 | 47 | 35% |
| Vitamin K (mcg) | 0 | 0 | 0 | |
| Thiamin (mg) | 48 | 75 | 47 | 50% |
| Riboflavin (mg) | 48 | 75 | 47 | 50% |
| Niacin (mg) | 48 | 75 | 47 | 50% |
| Vitamin B6 (mg) | 48 | 75 | 47 | 1250% |
| Folate (as folic acid and L-5-methyltetrahydrofolate) (mcg) | 104 | 75 | 47 | 100% |
| Vitamin B12 (as cyanocobalamin) (mcg) | 48 | 75 | 47 | 500% |
| Biotin (mcg) | 48 | 75 | 47 | 50% |
| Pantothenic Acid (mg) | 48 | 75 | 47 | 50% |
| Phosphorus (mg) | 48 | 0 | 20 | 55% |
| Iodine (mcg) | 0 | 75 | 47 | 50% |
| Magnesium (mg) | 72 | 0 | 33 | 60% |
| Zinc (mg) | 0 | 75 | 47 | 60% |
| Selenium (mcg) | 0 | 75 | 47 | |
| Copper (mg) | 0 | 75 | 47 | 50% |
| Manganese (mg) | 0 | 75 | 47 | 25% |
| Chromium (mcg) | 176 | 75 | 47 | 80% |
| Molybdenum | 0 | 75 | 0 | |
| Chloride (mg) | 0 | 0 | 0 | 10% |

†Taken twice per day; values in table represent single serving amounts and should be multiplied by two to determine total daily supplementation (e.g. calories per day = 368, 360 and 348, respectively).

Clinical Visits—During the study subjects in both arms A and B participated in clinical visits. Clinical visits took place once weekly during the 13 weeks of the study. Three of the clinical visits were individual appointments and 11 visits were group appointments. The individual clinical visits were visits 1, 10, and 14. The focus of the individual visits was the collection of safety, tolerance and acceptability data, and individually focused lifestyle instruction and counseling. Group clinical visits were visits 2, 3, 4, 5, 6, 7, 8, 9, 11, 12, and 13. The focus of the group visits was group focused lifestyle instruction and counseling. Attendance at the 14 clinical visits was required. Total length of participation in the study, including screening (up to 8 weeks) and optional follow-up for Adverse Events (AE) (up to 4 weeks), was approximately 25 weeks.

Individual Clinical Visits (Visits 1, 10, and 14): Subjects met with the study clinician. During the clinical visits, the study clinician reviewed questionnaires, assessed for signs and symptoms of adverse events, reviewed compliance to the study product and the dietary program and answered any questions from the subjects. Data collection (including physical measurements and phlebotomy for fasting laboratory assessments) was conducted at Visits 1, 10, and 14. Subjects received individual counseling and education pertinent to their assigned arm and the lifestyle change program at Visits 1 and 10.

Group Clinical Visits (Visits 2, 3, 4, 5, 6, 7, 8, 9, 11, 12, and 13): Subjects met collectively with the study clinician in small groups. During these visits, study staff presented education and experiential content to support healthy lifestyle change. Data collection (limited to weight measurement) was conducted at Visits 2, 3, 4, 5, 6, 7, 8, 9, 11, 12, and 13.

All concomitant medications taken during study participation were recorded on the visit progress note. A prescription medication was defined as a medication that can be prescribed only by a properly authorized/licensed clinician. Medications to be reported were concomitant prescription medications, over-the-counter medications, medical foods, and nutritional supplements taken during the course of the study.

No concomitant prescription medications, over-the-counter medications, medical foods, and nutritional supplements were to be started or doses changed during the study unless they were prescribed by the PI (or the subject's primary care giver) for treatment of a specific clinical event. Acetaminophen, however, was allowed for mild headache or myalgia at a dose of 650 mg three times daily as needed.

Inclusion criteria included: (1) Men and women ≥18 and ≤65 years old; (2) Generally healthy yet meeting criteria; (3) Body Mass Index (BMI)≥28.5 kg/m2 and <42 kg/m2. (4)

Visceral adiposity defined as a waist circumference≥35 inches for women and ≥40 inches for men; and (5) Elevated LDLc≥130 mg/dl.

In addition, subjects must have exhibited one of the following criteria: (1) decreased high density lipoprotein cholesterol (HDLc) defined as HDLc<50 mg/dl for women and <40 mg/dl for men; (2) elevated TG defined as TG≥130 mg/dl; (3) increased blood glucose defined as blood glucose ≥100 mg/dl; (4) elevated HbA1c defined as HbA1C≥5.7%; (5) elevated Homeostatic Model Assessment of Insulin Resistance (HOMA) score defined as ≥2.0; and (6) ability to understand and the willingness to sign a written informed consent document.

Exclusion criteria included: (1) change in prescription medications, over-the-counter medications, medical foods, and nutritional supplements within 30 days prior to Day 1 and for the duration of the study; (2) use of medications classified as narcotics 15 days prior to Day 1 and for the duration of the study; (3) use of prescription medications and/or over-the-counter medications (Acetaminophen permitted) for acute and semi-acute medical conditions 15 days prior to Day 1 and for the duration of the study (use of acetaminophen was permitted on an as-needed basis); (4) use of an investigational drug or participation in an investigational study within 30 days prior to Day 1 and for the duration of the study; (5) use of oral or injectable corticosteroids within 30 days prior to Day 1 and for the duration of the study; (6) use of anticoagulant medications (heparin compounds, platelet inhibitors or warfarin) within 30 days prior to Day 1 and for the duration of the study (use of aspirin 81 mg or 325 mg once daily is permitted); (7) use of neuro-active prescription medications including major and atypical antipsychotic medications, anti-depressants, anti-anxiolytics, and epilepsy medications within 30 days prior to Day 1 and for the duration of the study; (8) use of prescription medications, over-the-counter medications, medical foods, and nutritional supplements for the treatment of hyperlipidemia within 30 days prior to Day 1 and for the duration of the study: and (9) use of prescription medications, over-the-counter medications, medical foods, and nutritional supplements for the treatment of hyperglycemia within 30 days prior to Day 1 and for the duration of the study.

Subjects were not allowed to discontinue prohibited prescription medications, over-the-counter medications, medical foods, and nutritional supplements to meet enrollment criteria.

Exclusionary criteria relating to medical history included: (1) a history of allergy or intolerance to study products; (2) clinically significant vital sign abnormalities (systolic blood pressure <90 mm Hg or >160 mm Hg, diastolic blood pressure <50 mm Hg or >100 mmHg or resting heart rate of <50 or >100 bpm) at Screening; (3) a serious, unstable illness including cardiac, hepatic, renal, gastrointestinal, respiratory, endocrinologic, neurologic, immunologic, or hematologic disease; (4) known infection with HIV, TB or Hepatitis B or C; and (5) a current diagnosis or personal history of: (i) any cardiovascular disease including myocardial infarction, angina, cardiovascular surgery, congestive heart failure, cardiac arrhythmias or conduction abnormalities, cerebrovascular accident, transient ischemic attack (TIA), or peripheral vascular disease, deep vein thrombosis or pulmonary embolus; (ii) type 1 or type 2 Diabetes Mellitus; (iii) any autoimmune disease such as inflammatory bowel disease (including Crohn's Disease and/or ulcerative colitis), multiple sclerosis, rheumatoid arthritis, systemic lupus erythematosus, polymyositis, scleroderma and/or thyroiditis; (iv) any significant liver or kidney disease such as cirrhosis or non-alcoholic fatty liver disease, glomerulonephritis, and/or ongoing dialysis treatment; (v) any malignancy (with the exception of basal or squamous cell carcinoma of the skin if adequately treated and no recurrence for >5 years); (vi) any serious mental illness including a history of attempted suicide.

Exclusionary substance use included: (1) use of drugs of abuse (such as marijuana, cocaine, phencyclidine [PCP] and methamphetamine) 15 days prior to Day 1 and for the duration of the study; or (2) history of regular intake of >14 alcoholic drinks per week for females, and >21 drinks per week for males (1 drink=12 oz. beer, 4 oz. wine, or 1.0 oz. hard liquor).

Other exclusionary criteria included: (1) inability to comply with study and/or follow-up visits; (2) any concurrent condition (including clinically significant abnormalities in medical history, physical examination or laboratory evaluations) which, in the opinion of the PI, would preclude safe participation in this study or interfere with compliance; (3) any sound medical, psychiatric and/or social reason which, in the opinion of the PI, would preclude safe participation in this study or interfere with compliance; and (4) abnormal laboratory findings including: Abnormal blood counts (Hematocrit≤33% or >47%; WBC<3.0 or >12.0×103/mm3; platelets<140 or >500×109/L); abnormal kidney function test(s) (BUN>30 mg/dL or creatinine>1.5 mg/dL) or liver function test(s) (AST, ALT)>3× the upper limit of normal; serum calcium (≥11 mg/dL); serum K≤3.5 mEq/L; Na≤134 or ≥148 mEq/L.

Figure 7:
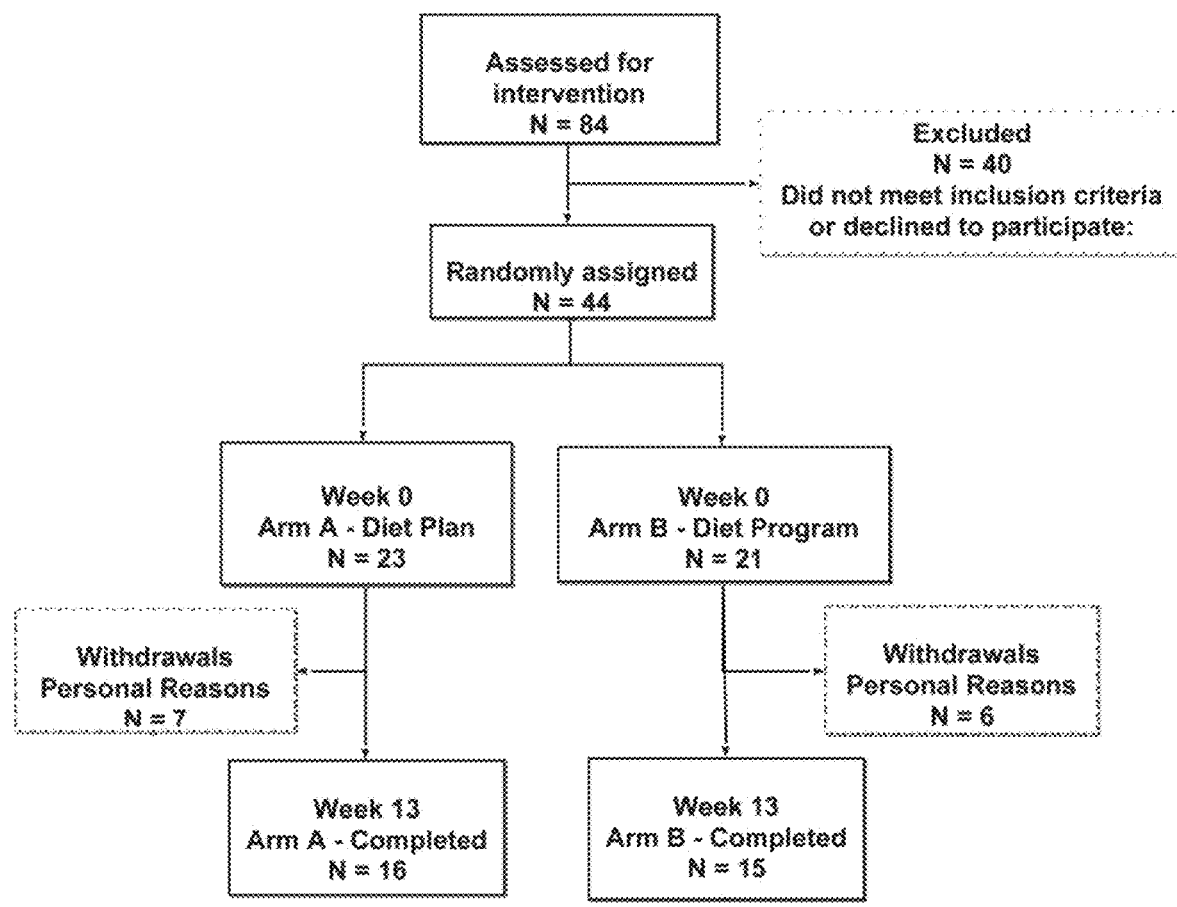
FIG. 7 is a schematic illustration of the subject selection and randomization into the InForm1.1 Diet (Arm A) and InForm1.1 Program (Arm B) in the open-labeled clinical trial conducted.

Subject recruitment and disposition—FIG. 7 graphically displays the subject selection and randomization into the DIET (Arm A) and PROG (Arm B) treatments.

Over the course of the study nitrite and nitrate levels were evaluated.

Assay of nitrite in saliva—Salivary NO strips, which detect salivary $NO_2$ as a biomarker for NO, have been shown to be useful as a reliable indicator of physiological NO levels. Nitric Oxide Test Strips (Berkeley Test, Berkeley, CA) were used in this study to measure the appearance of the NO biomarker $NO_2$ in saliva. Subjects recorded morning, lunch and dinner strip scores one hour post meal-time once per week on the day of the clinical visit.

Assay of nitrate in plasma—Nitrate/Nitrite (NOx) fluorometric assays were performed according to the manufacturer's instructions (Cayman Chemicals, Item No. 780051, Ann Arbor, MI). Plasma was filtered with 10 kDa MWCO VivaSpin 500 columns (Sartorius Stedim, VS0102). The microplate, with 10 µL of plasma per well, was incubated with nitrate reductase and cofactors at room temperature for 45 minutes before adding the 2,3-diaminonaphthalene (DAN) reagent. After a 10 minute incubation, 2.8 M sodium hydroxide was added and fluorescence was measured on a Cytation 5 plate reader (BioTek Instruments) with excitation and emission wavelengths of 375 and 417 nm, respectively.

Figure 8A:
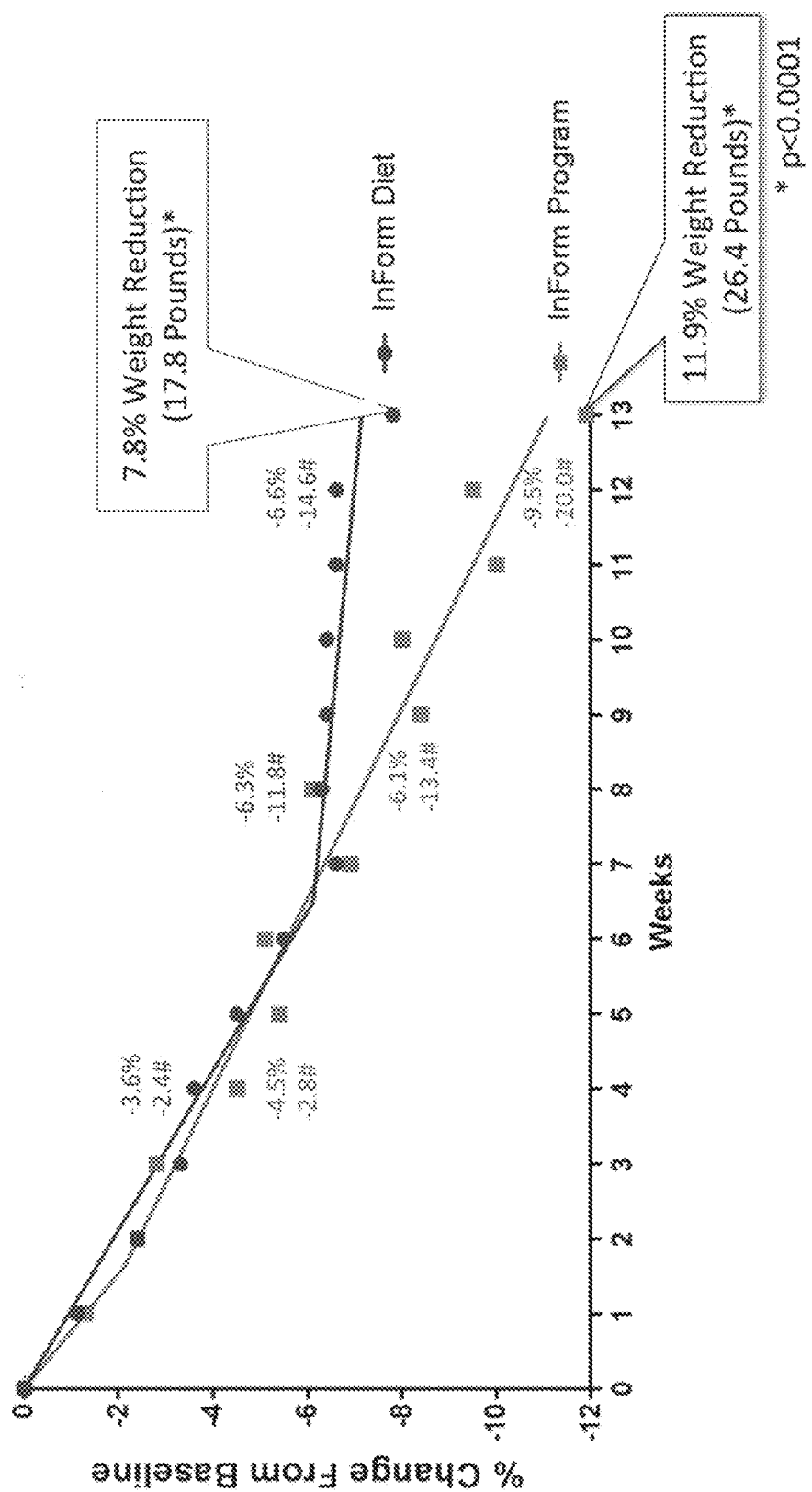
FIG. 8A graphically depicts the median percent change from baseline of weight loss of Arm A and Arm B subjects over the 13 weeks of the InForm1.1 clinical trial.
Figure 8B:
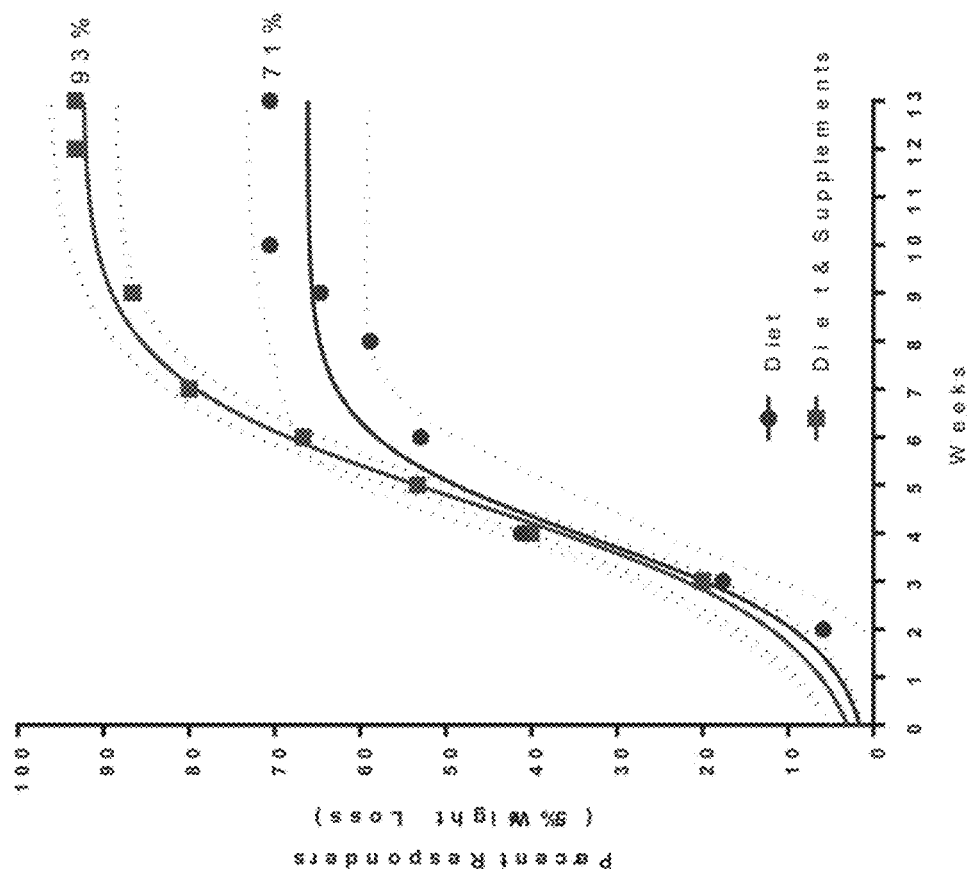
FIG. 8B graphically depicts the percent of Arm A and Arm B subjects that achieved a 5% reduction in weight over the 13 weeks of the InForm1.1 clinical trial.

Results weight and fat loss—Supplementation with the meal replacement formulation and weight loss stimulating dietary supplements, Arm B (InForm1.1 System) produced an 11.9% weight loss (26.4 pounds) versus a 7.8% weight loss (17.8 pounds) in the non-supplemented, Arm A, a 56% difference in result with p=0.0172. See FIG. 8A. Ninety-three percent of the supplement group achieved the benchmark 5% body weight loss over the study, while only 71% of the non-supplement group was able to attain the 5% level of weight reduction (p–0.05 for group difference). See FIG. 8B. Current treatment guidelines recommend that obese individuals lose 5% to 10% of their starting weights to minimize the risk factors for cardiovascular disease and reduce the risk for developing type 2 diabetes or hypertension. Globally, regulatory agencies set this 5% figure above placebo as absolute criteria for approval. Table 17 illustrates the superior performance of the InForm1.1 Program (Arm B) relative to weight loss drugs in achieving the 5% weight loss response among subjects.

TABLE 17

Contrasting Percent Responders for Program, Diet and Prescription Products

| Test Material | Evaluation | Responders |
|---|---|---|
| Arm A - InForm Diet | 8 weeks | 59% |
| Arm B - InForm System | 8 weeks | 80% |
| Placebo† | 8 weeks | 8% |
| Bupropion (400 mg) | 8 weeks | 48% |
| Placebo†† | 12 weeks | 12% |
| Lorcaserin BID (10 mg) | 12 weeks | 36% |
| Arm A - InForm Diet | 12 weeks | 71% |
| Arm B - InForm System | 12 weeks | 93% |

Further, the number of subjects achieving either a 5% or 10% weight loss was substantially better for the Arm B versus prescription drugs. See Table 18. With 93% of the subjects exhibiting a 5% or greater weight loss during the trial period, the InForm1.1 System (Arm B) was 55% better than the next best performing agent liraglutide at 60% and 121% better than orlistat at 42%. Arm B showed even greater benefits versus prescription drugs when the number of subjects achieving a 10% or greater weight loss was considered; the InForm1.1 System was 300% better than orlistat and 94% better than liraglutide.

TABLE 18

Five and Ten Percent Responders for Program and Three Prescription Products

| Test Material | Period | ≥5% | ≥10% |
|---|---|---|---|
| Placebo | 56 weeks | 23% | 9% |
| Orlistat (Alli ®) | 24 weeks | 42% | 15% |
| Lorcaserin (Belviq ®) | 56 weeks | 47% | 22% |
| Liraglutide (Victoza ®) | 56 weeks | 60% | 31% |
| Arm B - InForm1.1 System | 12 weeks | 93% | 60% |

Figure 9:
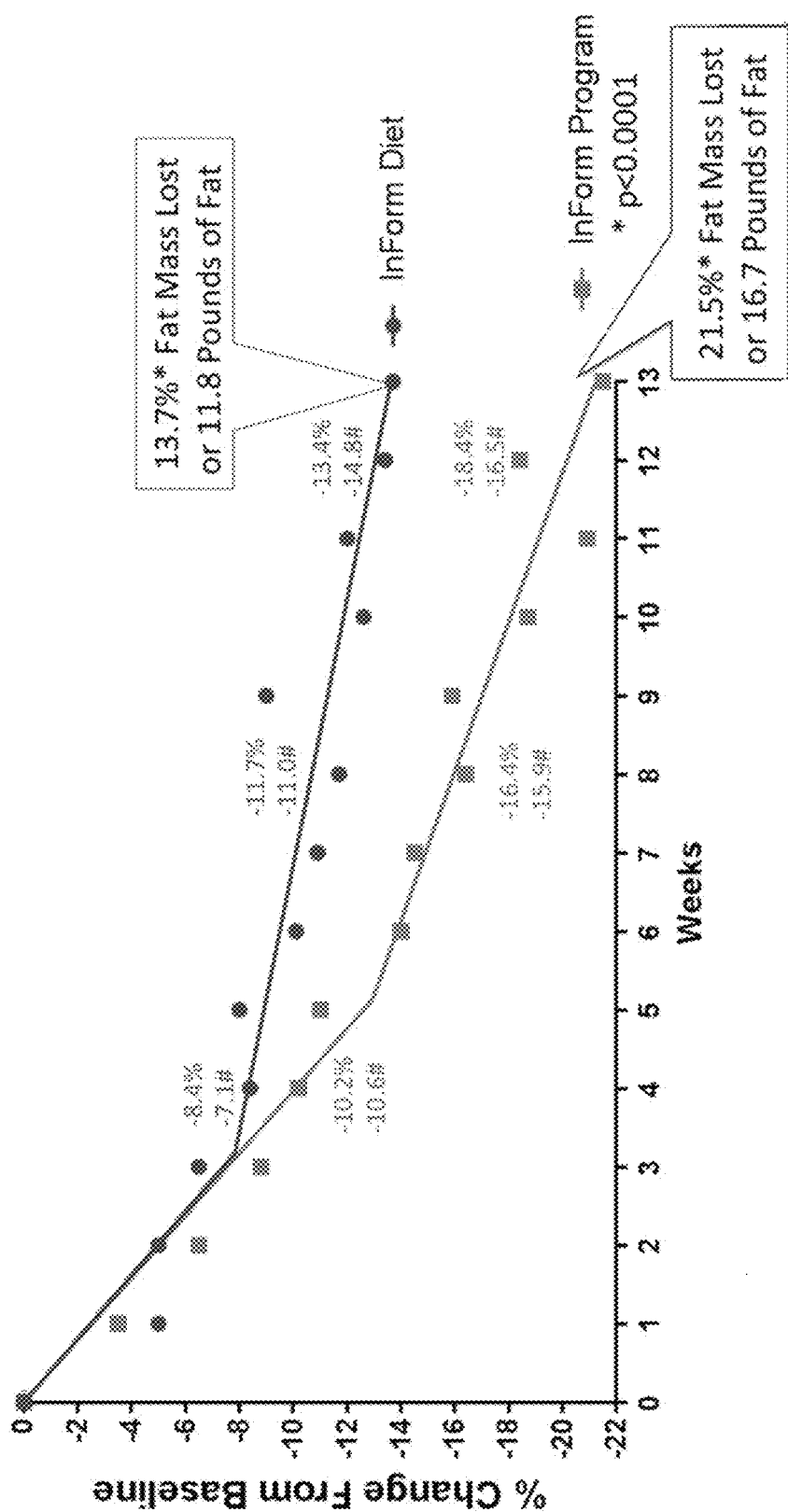
FIG. 9 graphically depicts the median percent change from baseline of fat mass loss of Arm A and Arm B subjects over the 13 weeks of the InForm1.1 clinical trial.

Similarly, the InForm1.1 System, Arm B, experienced a median 21.5% (16.7 pounds) fat mass loss over the study compared with a median 13.7% (11.8 pounds) for the non-supplemented group, Arm A, with p<0.0001. (See FIG. 9).

Figure 10:
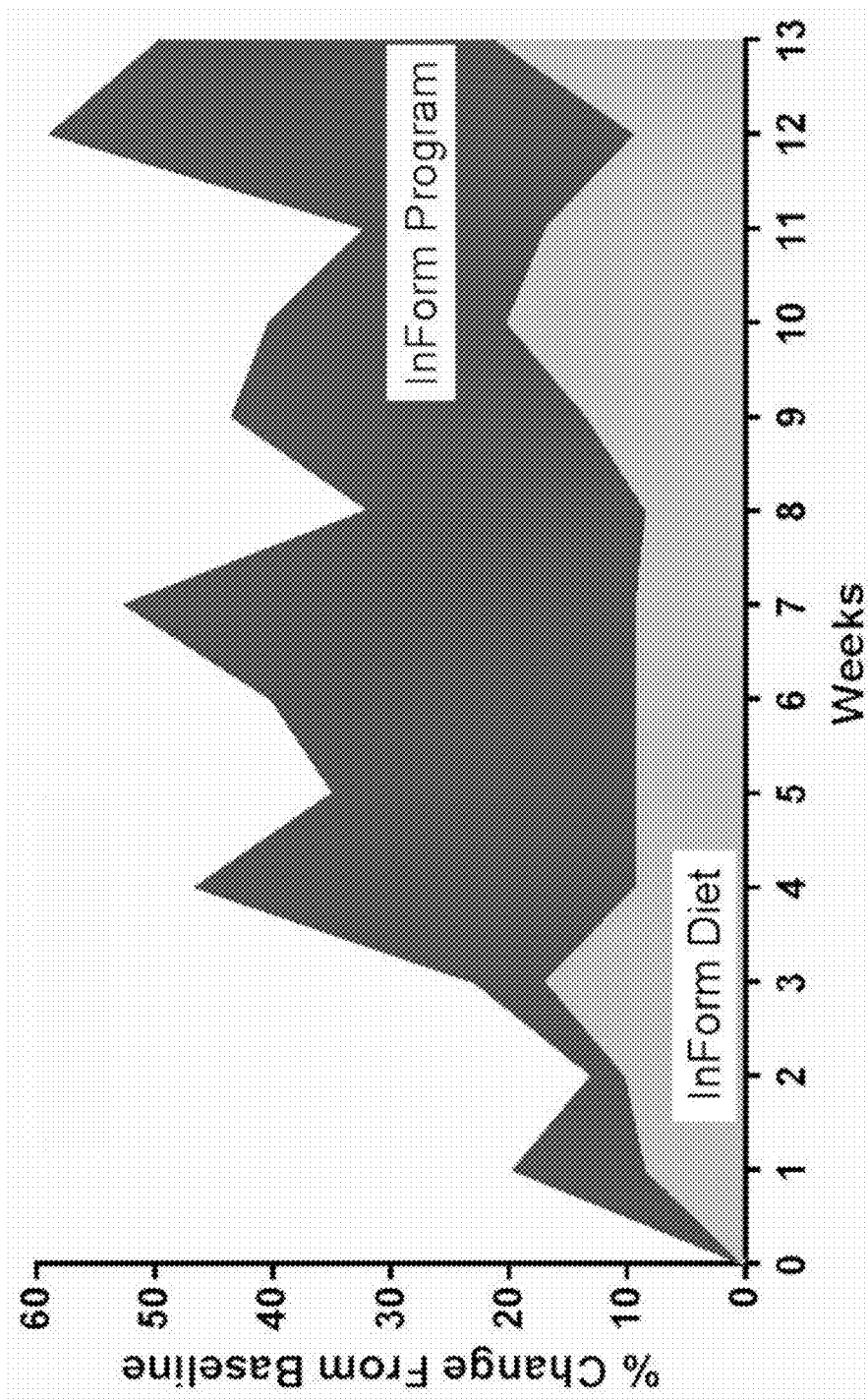
FIG. 10 graphically depicts the median percent change from baseline of salivary nitrite of Arm A and Arm B subjects over the 13 weeks of the InForm 1.1 clinical trial.
Figure 11:
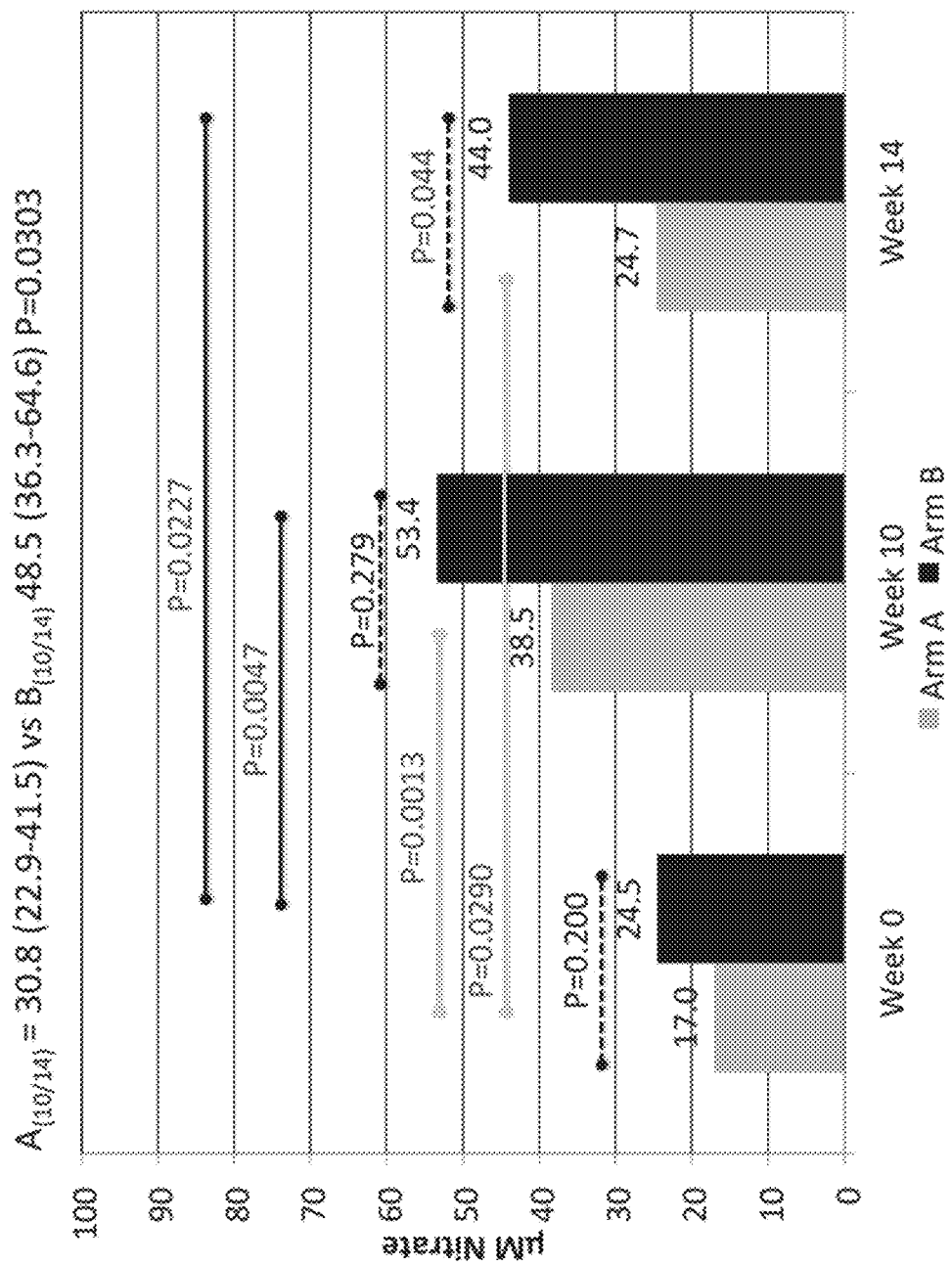
FIG. 11 graphically depicts the mean morning plasma nitrate concentrations at week 0, week 10 and week 14 clinic visits for Arm A and Arm B subjects in the clinical trial.

Results nitric oxide biomarker levels—While both arms of the study exhibited an increase in the salivary NO biomarker nitrite, supplementation with the weight loss stimulating dietary supplements resulted in a median percent increase of 110 percent in salivary NO biomarker production in Arm B over Arm A. See Table 19; FIG. 10. Similarly, plasma nitrate was increased by dietary modification in both arms at 10 and 14 weeks, but supplementation with the weight loss stimulating dietary supplements produced a 1.6-fold increase in overall mean plasma nitrate concentration over the study—30.8 µM (95% confidence interval: 22.9-41.5) vs 48.5 µM (36.3-64.6) with p=0.030. See FIG. 11.

TABLE 19

Median Salivary NO Biomarker Increase

| Treatment Arm | Median % Increase | P-Value |
|---|---|---|
| Arm A (Diet Only) | 21 | 0.0471 |
| Arm B (Diet and Program) | 49 | 0.0004 |
| Arm A vs B | 110 | 0.0003 |

Thus, it has been demonstrated that healthy gut modification through supplementation with the group of weight loss stimulating dietary supplements has led to increased plasma $NO_3$ and salivary $NO_2$, precursors of NO.

FIG. 10 schematically represents week 13 to baseline comparison of subjects scored NO biomarker strips one hour after dinner weekly.

Results Blood pressure changes—Coincident with increases in plasma $NO_3$ and the salivary NO biomarker $NO_2$, both diets decreased blood pressure values from week 1 initial clinic visits. See Table 20. There was a trend for a greater decrease in Arm B over Arm A, but the differences did not reach statistical significance.

TABLE 20

Median Percent Changes in Blood Pressure from Baseline

| | Median % Change† | | Median % Change | |
|---|---|---|---|---|
| | Systolic | Diastolic | Systolic | Diastolic |
| Arm A | −5* | −7* | — | |
| Arm B | −11† | −12† | −125 | −62§ |

From Baseline to Week 13;
*p < 0.05;
†p < 0.01;
§p = 0.06

Results Lipid biomarker changes—Overall, lipid biomarkers were more favorably improved in the Arm B than Arm A. See Table 21. Thus, in addition to increased weight loss, Arm B was more effective in the reduction of cardiovascular risk factors associated with lipid biomarkers. The improvement in TG/HDL ratio also indicates the potential of the diet program to modify risk of developing metabolic syndrome and type 2 diabetes.

TABLE 21

Median Percent Changes of Lipid Biomarkers (Arm A) versus (Arm B)

| Lipid Biomarker | Arm A | Arm B | Improvement |
|---|---|---|---|
| Total Cholesterol (TC) | −8.0** | −18** | −129** |
| LDL Cholesterol (LDL) | −10* | −19** | −80** |
| Triglycerides (TG) | −31** | −51** | −66* |
| High Density Lipoprotein (HDL) | −6 | −3 | −54 |
| TC/HDL | −4.0 | −16** | −268** |
| LDL/HDL | −0.9 | −16 | −1751** |
| TG/HDL | −26* | −47** | −80* |

*p < 0.05;
**p < 0.01 vs baseline within Arms and Program v Diet alone

Example 3—Evaluation of a Secondary Program for Healthy Weight and Cardiometabolic Function The Program as described in Example 2 is replicated with the substitution of three capsules of CurcuminBP per day for a total dose of about 1,568 mg total curcuminoids for the BerberineIR used in Example 2. This substitution produces similar positive effects on health, cardiometabolic and body weight variables as described in Example 2.

Example 4—InForm1.2 an Additional Program for Healthy Weight and Cardiometabolic Function The Program as described in Example 2 was replicated with the following modifications: (1) the trail was a single-arm, observational study, (2) 1,000 mg of cinnamon divided over two doses was substituted for the 999 mg of berberine, and (3) one to three capsules of *Bacillus coagulans* per day for a total dose of about 3 to 9 billion cfu per day was substituted for the Probiotic 11 used in Examples 2 and 3. A complete outline of the clinical protocol is presented in Table 22. The food plan was that as described previously in Table 14.

TABLE 22

InForm1.2 Observational Study Design

| Activity | Details |
|---|---|
| Recruiting and Screening | Recruit generally healthy overweight and obese adults. Physical Measurements (height, weight and waist circumference). Clinical assessment (completion of medical history questionnaire, and visit with study clinician including limited physical examination) Phlebotomy for complete metabolic profile (CMP), HbA1c, insulin and serum pregnancy test for women of child bearing potential. |
| Week 0/ Visit 1 | Confirm cardiometabolic syndrome with repeat physical and clinical variables. Measurements included: Physical measurements (Height, Weight and Waist Circumference), Vital signs (including blood Pressure and heart Rate), Body Impedance Analysis, Peripheral Artery Tonometry, Metabolic age, Clinical assessment (completion of medical history questionnaire, and visit with study clinician), Urine pregnancy test for women of child bearing potential, Fasting phlebotomy for CBC, CMP, insulin, HbA1c, oxidized LDLc (oxLDL), myeloperoxidase (MPO), high sensitivity C-reactive protein (hs-CRP), advanced lipid panel including standard lipid panel, particle sizes and particle numbers (NMR) for all subjects. |
| Weeks 1-13 | Low-glycemic food plan Physical activity Cognitive Behavioral Program Protein Shakes (bid) 20 g protein 2 g Phytosterols Supplements Antioxidant formulation Probiotic Fish oil capsules |

TABLE 22-continued

InForm1.2 Observational Study Design

| Activity | Details |
|---|---|
| Weeks 1-8 and 10-13 | Cinnamon Fiber drinks All subjects met collectively with the study clinician for a cognitive behavioral program at 11 didactic/experiential group visits, the body weight, body composition and blood pressures were measured weekly. |
| Weeks 9 and 13 | Review questionnaires, assess for signs and symptoms of adverse events, review compliance to the study products and answer any participant questions. Measurements of baseline variables repeated. |

TABLE 23

Meal Replacement and Weight Loss Stimulating Supplements for InForm1.2

| | Daily Servings | Function |
|---|---|---|
| Meal Supplement | | |
| Meal Replacement | 2 scoops 2x | Amino acids/ antioxidants |
| Weight Loss Stimulating Supplements | | |
| Phytosterols | 1 scoop 2x | Biomatrix enrichment |
| Cinnamon | 500 mg bid with shake | Antimicrobial |
| CardioxLDL ® | 2 capsules/dinner | Antioxidant |
| *Bacillus coagulans* | 1 capsule 3 billion CFU/meal | Repairing dysbiosis |
| Super Omega-3 EPA | 1 capsule 2x | Anti-inflammatory |
| Super Supplemental Vitamins & Minerals and Minerals | 2 tablets 2x | Biomatrix enrichment |

Figure 12:
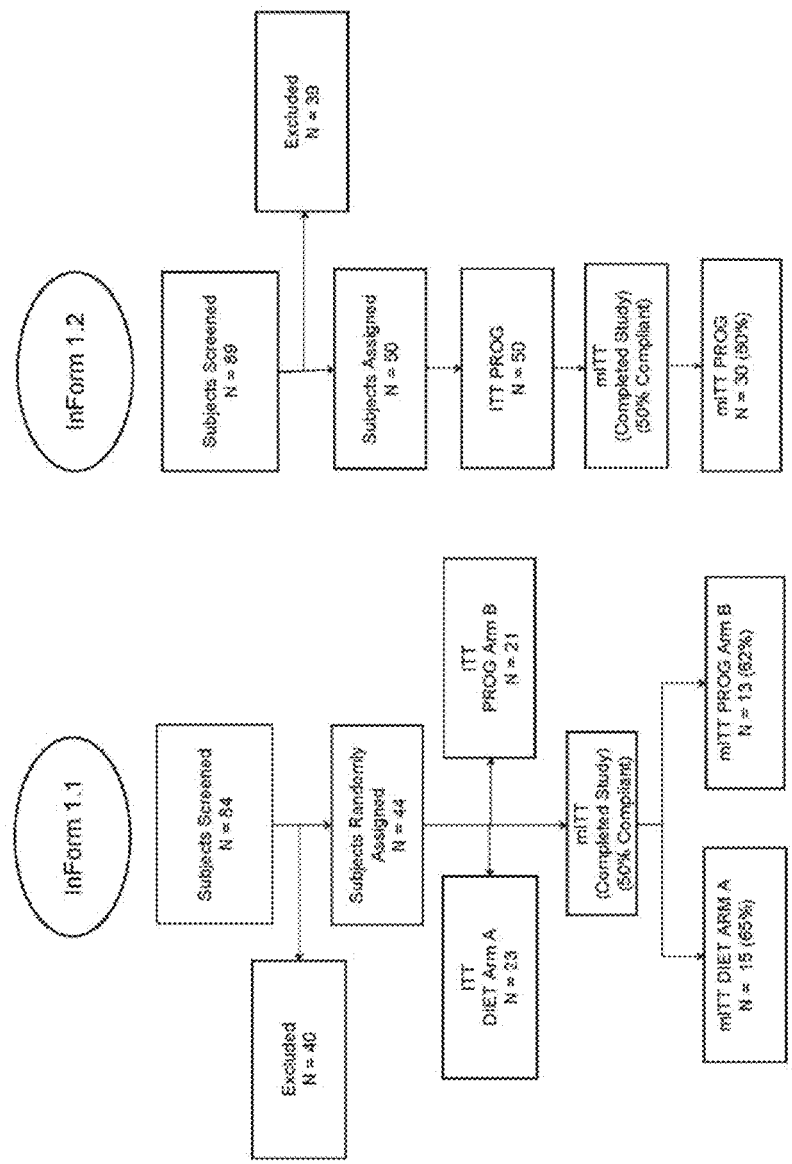
FIG. 12 is a schematic illustration of the disposition of subjects in both the InForm1.1 and InForm1.2 clinical trials on the intent-to-treat and modified intent-to-treat basis.

The clinical data from both studies were analyzed on both an intent-to-treat (ITT) and modified intent-to treat (mITT) basis (cf FIG. 12 for disposition of subjects by study and method of analysis).

Intent-To-Treat (ITT) Data Analysis—This analysis considers all subjects randomized into their respective treatments and estimates responses from dropouts through the last-observation-carry forward method. The ITT analysis is considered the most conservative estimate of effectiveness as it reflects conditions likely to be encountered in the market.

TABLE 24

Baseline Median Cardiometabolic Profiles of DIET, PROG1.1 and PROG1.2 Subjects for Intent-To-Treat Analysis

| Variable | DIET ONLY† (n = 23) | PROG1.1† (n = 21) | PROG1.2† (n = 50) |
|---|---|---|---|
| Gender, % Female | 60.9 | 66.7 | 60.0 |
| Age (yrs) | 47 (64-33)$^a$ | 46 (64-27)$^a$ | 45 (63-25)$^a$ |
| Weight (lb) | 229 (383-165)$^a$ | 229 (296-170)$^a$ | 231 (343-164)$^a$ |
| BMI (kg/m$^2$) | 34.6 (53.0-26.9)$^a$ | 35.4 (43.0-31.3)$^a$ | 35.9 (50.8-28.6)$^a$ |
| Body Fat Mass (lbs) | 92.8 (149-45.5)$^a$ | 96.7 (131-68.3)$^a$ | 93.9 (168-53.7)$^a$ |
| Waist circumference (in) | 44.0 (61.0-35.5)$^a$ | 44.5 (52.0-35.0)$^a$ | 44.3 (59.5-38.0)$^a$ |
| Systolic BP (mm Hg) | 136 (172-102)$^a$ | 133 (164-115)$^a$ | 130 (167-101)$^a$ |

TABLE 24-continued

Baseline Median Cardiometabolic Profiles of DIET, PROG1.1
and PROG1.2 Subjects for Intent-To-Treat Analysis

| Variable | DIET ONLY† (n = 23) | PROG1.1† (n = 21) | PROG1.2† (n = 50) |
|---|---|---|---|
| Diastolic BP (mm Hg) | 83 (99-71)$^a$ | 83 (99-73)$^a$ | 84 (108-66)$^a$ |
| Salivary Nitrite (Morning unit | 3.0 (7.0-0.10)$^a$ | 3.0 (7.5-1.0)$^a$ | 3.0 (5.0-0.10)$^a$ |
| Salivary Nitrite (Noon units) | 4.5 (6.8-0.10)$^a$ | 3.5 (6.5-0.10)$^a$ | 4.0 (7.0-1.0)$^a$ |
| Salivary Nitrite (Evening units | 5.3 (7.4-2.0)$^a$ | 4.0 (7.0-0.10$^a$ | 4.4 (7.0-1.5)$^a$ |
| Total Cholesterol (mg/dL) | 199 (256-149)$^a$ | 224 (320-137)$^a$ | 201 (423-139)$^a$ |
| LDL Cholesterol (mg/dL) | 128 (177-76)$^a$ | 138 (217-60)$^a$ | 121 (201-44)$^a$ |
| TG (mg/dL) | 173 (571-77)$^a$ | 184 (332-96)$^a$ | 171 (527-81)$^a$ |
| HDL Cholesterol (mg/dL) | 43 (67-25)$^a$ | 42 (81-26)$^a$ | 40 (64-24)$^a$ |
| oxLDL (U/L) | 47 (77-32)$^a$ | 50 (79-23)$^a$ | 52 (116-6.1)$^a$ |
| Cholesterol/HDL | 4.7 (7.5-2.7)$^a$ | 5.1 (7.9-3)$^a$ | 5.0 (12.4-2.8)$^a$ |
| LDL/HDL | 2.8 (5.2-1.2) | 2.8 (5.2-1.2) | 3.0 (4.8-1.3) |
| TG/HDL | 4.0 (23-1.5)$^a$ | 4.3 (11.4-1.2)$^a$ | 4.3 (22-1.5)$^a$ |
| oxLDL/HDL | 1.1 (1.9-0.61)$^a$ | 1.2 (1.8-0.36)$^a$ | 1.4 (3.4-0.16)$^a$ |
| Glucose (mg/dL) | 92 (121-71)$^a$ | 90 (103-79)$^a$ | 93 (121-64)$^a$ |
| Insulin (µIU/mL) | 7.5 (18-2.5)$^a$ | 7.5 (27-2.7)$^a$ | 9.4 (31-1.0)$^b$ |
| HbA1C (%) | 5.8 (7.0-5.7)$^a$ | 5.7 (6.2-4.8)$^a$ | 5.8 (6.8-5.2)$^a$ |
| HOMA-IR | 1.78 (4.25-0.50)$^a$ | 1.72 (5.80-0.54)$^a$ | 2.24 (8.21-0.21)$^b$ |
| HOMA-β | 90 (369-50)$^a$ | 104 (427-40.5)$^a$ | 116 (1656-17.1)$^a$ |
| hs-CRP (mg/L) | 2.6 (42-0.60)$^a$ | 2.9 (9.8-0.40)$^a$ | 3.3 (27-0.50)$^a$ |
| 10-Year Cardiac Risk/BMI (%) | 6.9 (23-2.3)$^a$ | 7.1 (23-2.0)$^a$ | 6.9 (19-0.89)$^a$ |
| 10-Year Cardiac Risk/Lipids (%) | 6.1 (15-2.6)$^a$ | 6.5 (18-1.4)$^a$ | 5.7 (20-0.80)$^a$ |

BMI: Body Mass Index; BP = Blood Pressure; LDL: Low Density Lipoprotein; HDL: High Density Lipoprotein; OxLDL: Oxidized Low Density Lipoprotein; Apo A: Apolipoprotein A1; Apo B: Apolipoprotein B; HbA1c: Glycated Hemoglobin; HOMA-IR: Homeostatic Model Assessment Insulin Resistance computed using the formula HOMA-IR = [(Glucose$_{mg/dL}$) × (Insulin$_{\mu IU/mL}$)]/405; hs-CRP: high sensitivity C-reactive protein.
†Tabulated values are medians with parenthetic minimum and maximum values, respectively; common superscript letters indicate P > 0.05 computed from Mann-Whitney U-Test.

Intent-to-treat analysis results—Groups representing the DIET only and PROG treatments from InForm1.1 and InForm1.2 were similar at baseline (Table 24). Insulin and HOMA-IR scores were statistically elevated compared to DIET and InForm1.1 arms but in the normal range.

Table 25 summarizes the effects of DIET, PROG1.1 and PROG1.2 on the clinical variables as median percent changes from baseline for the ITT analysis.

Overall results—In general, the DIET performed well and provided significant improvements from baseline for critical variables such as weight loss, fat mass, select lipid and glucose biomarkers and 10-year cardiovascular risk. Overall, however, PROG1.1 and PROG1.2 dramatically outperformed the DIET ONLY group in all of these variables. Several statistically significant differences between the two programs existed and are detailed in the following sections.

Figure 13A:
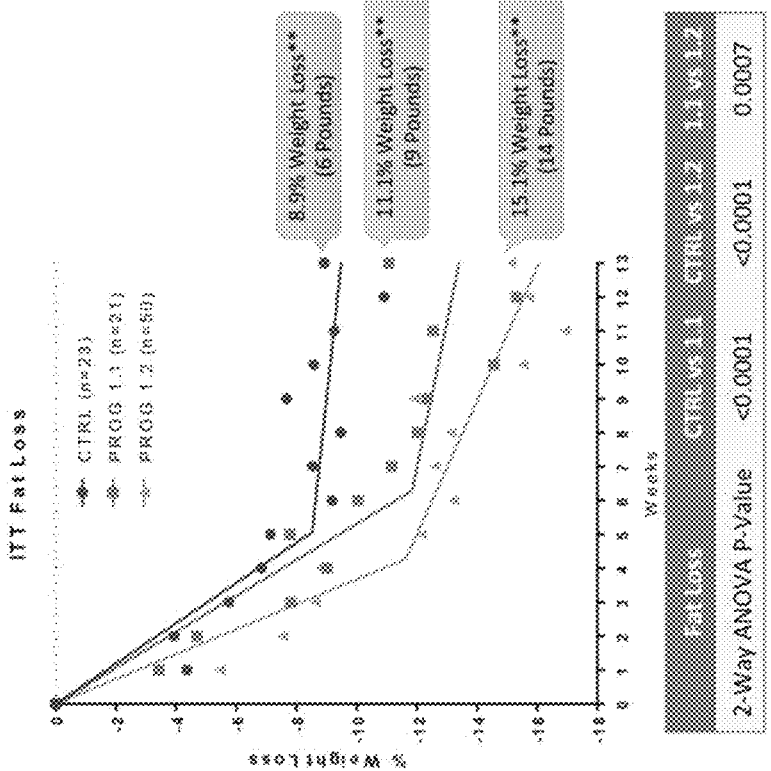
FIG. 13A graphically depicts the median percent change from baseline of weight loss of subjects over the 13 weeks of the InForm 1.1 clinical trial, InForm1.2 clinical trials and the control as based upon an intent-to-treat analysis.

Results weight and fat loss—Supplementation with the meal replacement formulation and weight loss stimulating dietary supplements, (PROG1.1 and PROG1.2 Systems) produced losses of 7.5% (17 pounds) and 8.4% (20 pounds), respectively versus a 4.4% (9 pounds) weight in the non-supplemented CTRL arm. (cf FIG. 13A). As expected, similar results were seen for BMI.

Figure 13B:
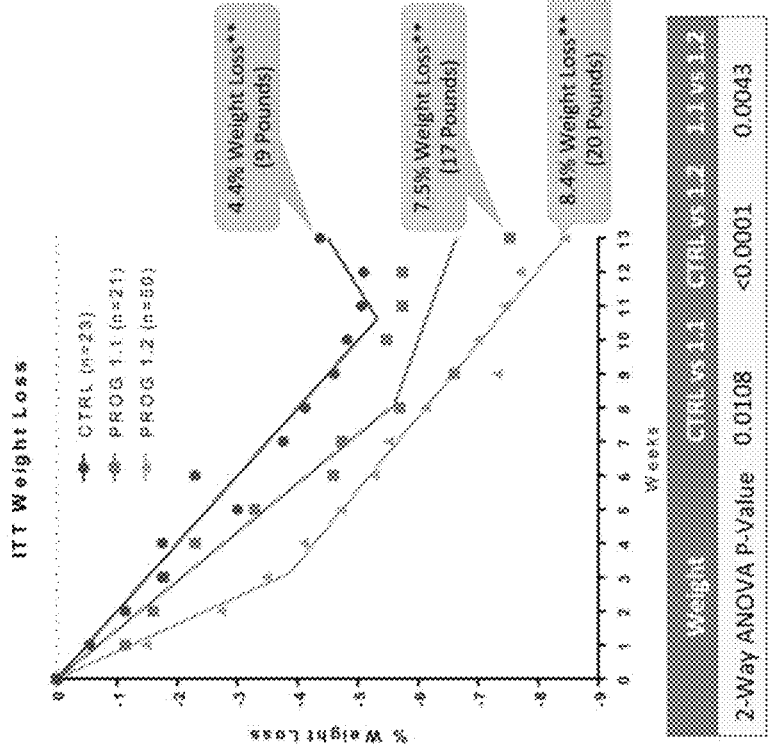
FIG. 13B graphically depicts the median percent change from baseline of fat loss of subjects over 13 weeks of the InForm 1.1 clinical trial, In Form 1.2 clinical trial, and the control as based upon an intent-to-treat analysis.

Loss of fat mass (lbs) was also significantly better in the PROG1.1 and PROG1.2 arms compared to the DIET ONLY with median percent decreases from baseline of 11.1% and 15.1%, respectively, compared to 8.9% in the CTRL arm. PROG1.2 was also significantly different from PROG1.1 (P<0.0007; FIG. 13B).

Figures 14A, 14B:
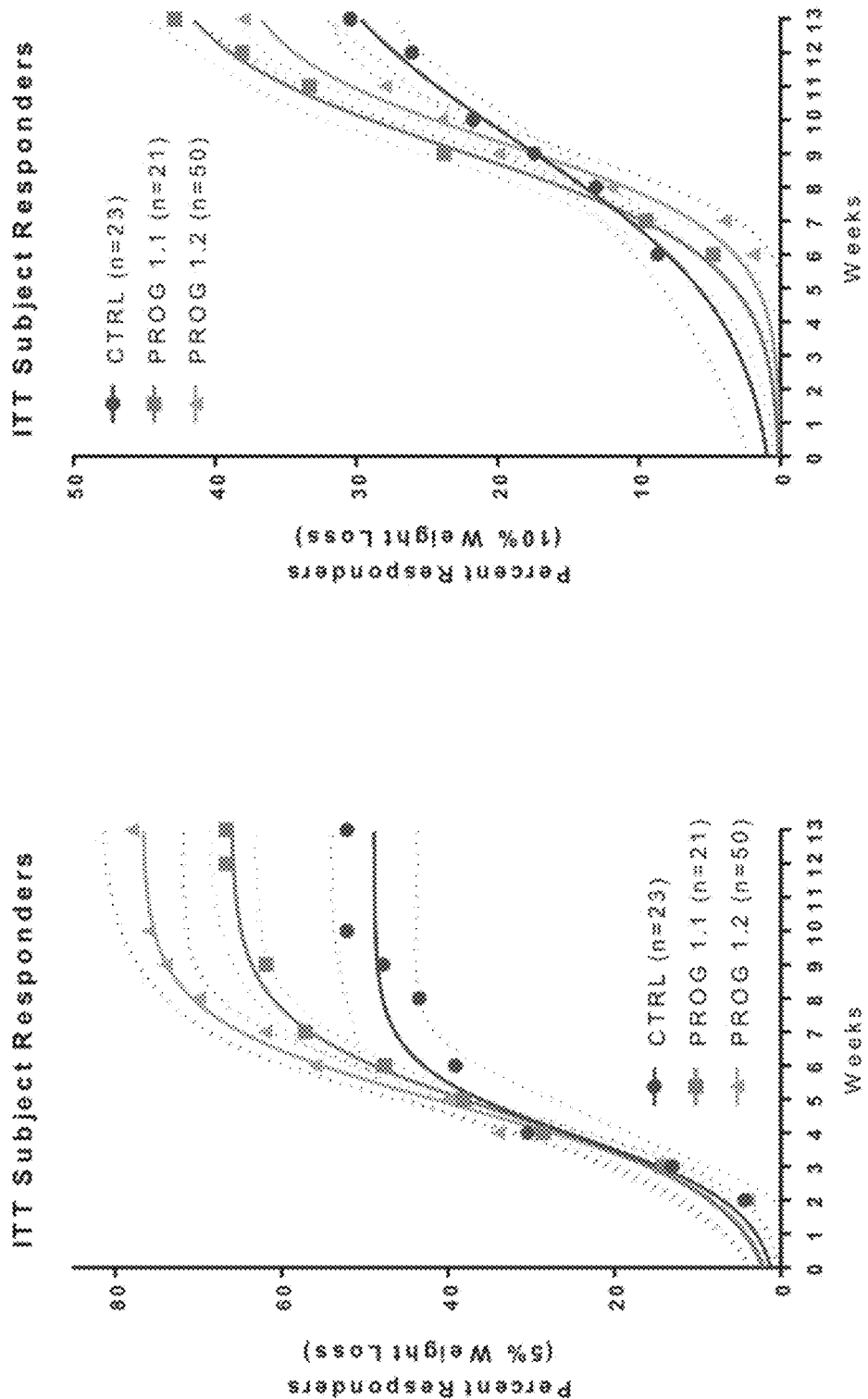
FIG. 14A graphically depicts the number of subjects overall achieving a 5% weight loss as determined from an intent-to-treat analysis.
FIG. 14B graphically depicts the number of subjects overall achieving a 10% weight loss as determined from an intent-to-treat analysis.
Figures 15A, 15B:
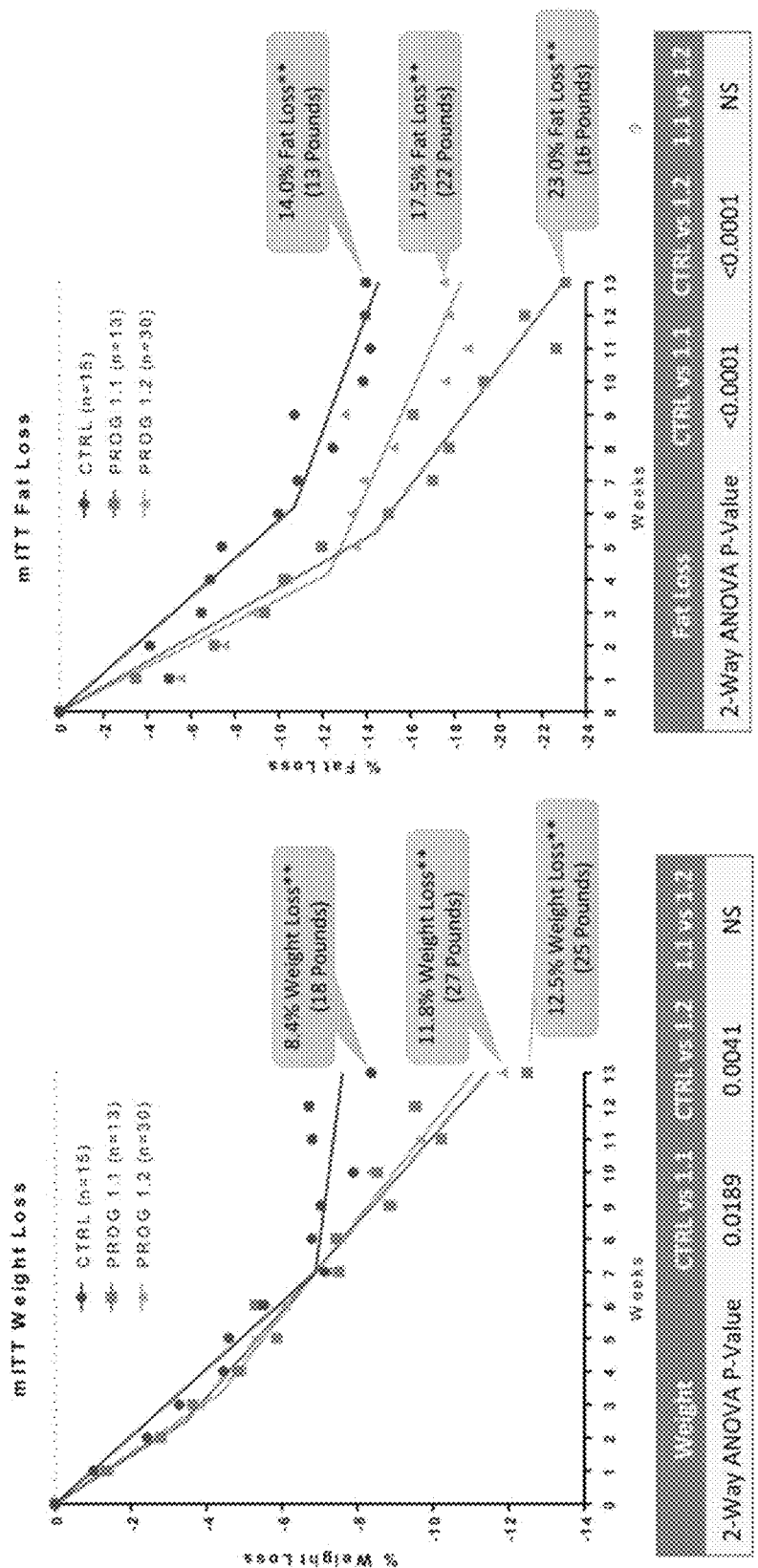
FIG. 15A graphically depicts the median percent change from baseline of weight loss of subjects over the 13 weeks of the InForm 1.1 clinical trial, the Inform 1.2 clinical trials and the control as based upon a modified intent-to-treat analysis.
FIG. 15B graphically depicts the median percent change from baseline of fat loss of subjects over the 13 weeks of the InForm 1.1 clinical trial, the Inform 1.2 clinical trials and the control as based upon a modified intent-to-treat analysis.
Figures 16A, 16B:
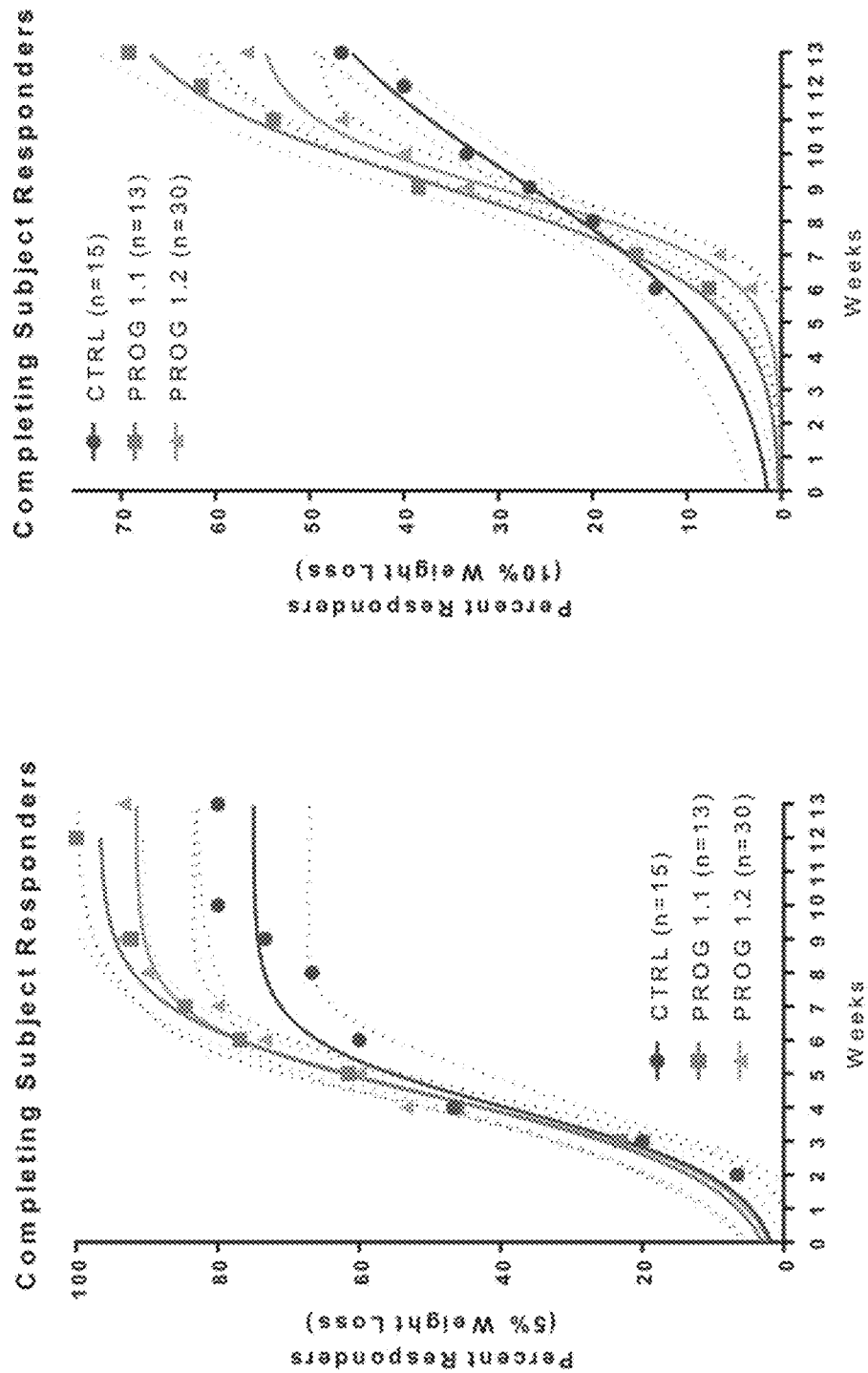
FIG. 16A graphically depicts the number of subjects overall achieving a 5% weight loss as determined from a modified intent-to-treat analysis.
FIG. 16B graphically depicts the number of subjects overall achieving a 10% weight loss as determined from a modified intent-to-treat analysis.

Further, the number of subjects achieving either a 5% or 10% weight loss was substantially better for both PROG arms relative to DIET ONLY, FIG. 14A and FIG. 14B, respectively. A greater number of subjects achieved a 5% weight loss in PROG1.2 than PROG1.1, but these results reversed for the percent of subjects achieving a 10% weight loss.

Results blood pressure—No change from baseline was observed for either systolic or diastolic blood pressure for the DIET ONLY arms, while both PROG1.1 and PROG1.2 produced similar decreases in blood pressure of 7.8% and 6.6% for systolic and 6.7% and 92% for diastolic, respectively. These changes in blood pressure were mirrored by increases in salivary nitrite observed in both PROG arms.

Lipid biomarkers—Total and LDL cholesterol were reduced from baseline to a greater extent in the supplement arms than in the DIET ONLY group. Triglycerides were decreases to a similar extent in all three arms, respectively, 27, 31 and 33% for DIET, PROG1.1 and PROG1.2.

Glucose biomarkers—Glucose, insulin, HbA1c and HOMA-IR were more dramatically reduced in the PROG1.2 arm than in the PROG1.1 or DIET ONLY arm.

Inflammation biomarkers—hs-CRP was reduced to a similar extent in the PROG1.1 and PROG1.2 arms, 18 and 19% from baseline respectively, while no change from baseline was noted for the DIET ONLY arm.

10-year Cardiovascular Risk—The decreases in 10-year cardiovascular risk based on BMI in the PROG1.1 and PROG1.2 arms were 2.9- and 3-fold times the 6.2% decrease in the DIET ONLY arm. Even more dramatic was the decrease seen in 10-year cardiovascular risk seen when estimated from serum lipid changes. PROG1.1 and PROG1.2 were 13- and 14-fold better than diet alone.

TABLE 25

DIET and PROG Cardio-Metabolic Risk Variables for ITT Analysis

| Variable | DIET ONLY (n = 23)† Median % Change† | PROG1.1 (n = 21)† Median % Change† | PROG1.2 (n = 50)† Median % Change† |
|---|---|---|---|
| Weight (lbs) | −4.4a (6 to −19.6) | −7.5b (0.0 to −16) | −8.4**c (0.0 to −21) |
| BMI (kg/m²) | −4.4a (6 to −20) | −7.5b (0.0 to −16) | −8.4**c (0.0 to −21) |
| Fat Mass (lbs) | −8.9a (3.8 to −27) | −11b (2.7 to −35) | −15**c (0.0 to −38) |
| Waist circumference (in) | 6.7a (0.0 to −17) | −9.5b (0.0 to −17) | −7.5**b (0 to −20) |
| Systolic BP (mm Hg) | 0.0a (13 to −24) | −7.8b (7.1 to −24) | −6.6b (11 to −32) |
| Diastolic BP (mm Hg) | 0.0a (8.2 to −19) | −6.7b (2.6 to −21) | −9.2b (7.7 to −27) |
| Nitrate Strip - Morning | 26a (1900 to −97) | 33b (140 to −13) | 33b (3900 to −67) |
| Nitrate Strip - Afternoon | 18a (5600 to −73) | 25b (7400 to −11) | 25 b (300 to −68) |
| Nitrate Strip - Evening | 9.1a (150 to −95) | 27b (7900 to −29) | 29b (233 to −43) |
| Total Cholesterol (mg/dL) | −3.6** (21 to −34) | −9.3** (0.0 to −31) | −12** (54 to −38) |
| LDL Cholesterol (mg/dL) | 0.0 (65 to −37) | −6.8* (33 to −35) | −11** (128 to −37) |
| TG (mg/dL) | −27** (7.7 to −55) | −31** (30 to −68) | −33** (27 to −80) |
| HDL Cholesterol (mg/dL) | 0.0 (18 to −19) | 0.0 (17 to −12) | 0.0 (57 to −34) |
| oxLDL (U/L) | −3.1* (37 to −41) | 0.0 (6.7 to −37) | −12** (507 to −56) |
| Cholesterol/HDL | −2.5 (30 to −41) | −13** (1.3 to −35) | −12** (21 to −55) |
| LDL/HDL | 0.0 (69 to −44) | −9.3** (15 to −42) | −11* (47 to −53) |
| TG/HDL | −25** (15 to −60) | −26** (34 to −73) | −32** (41 to −87) |
| oxLDL/HDL | 0.0 (27 to −45) | −7.8** (19 to −44) | −8.5** (450 to −69) |
| Glucose (mg/dL) | 0.0 (16 to −37) | 0.0 (12 to −16) | −1.6** (28 to −20) |
| Insulin (μIU) | −14* (31 to −72) | −6.7* (57 to −76) | −29** (305 to −82) |
| HbA1c (%) | 0.0 (8.6 to −14) | 0.0 (4.2 to −11) | −3.4** (1.7 to −9.2) |
| HOMA-IR | −8.2* (30 to −82) | −8.9** (69 to −79) | −30** (333 to −84) |
| HOMA-β | −9.2* (60 to −74) | −11** (23 to −69) | −21** (249 to −97) |
| hs-CRP (mg/L) | 0.0 (439 to −63) | −18** (67 to −55) | −19** (471 to −75) |
| 10-Year Cardiac Risk/BMI (%) | −6.2* (35 to −54) | −18** (3.5 to −56) | −19** (17 to −67) |
| 10-Year Cardiac Risk/Lipids (%) | −1.8* (29 to −57) | −26** (3.6 to −69) | −28** (22 to −62) |

Note:
BMI: Body Mass Index; BP: blood pressure; LDL: Low Density Lipoprotein; HDL: High density lipoprotein; TG: triglycerides; High Density Lipoprotein; OxLDL: Oxidized Low Density Lipoprotein; Apo A: Apolipoprotein A1; Apo B: Apolipoprotein B HbA1c: Glycated Hemoglobin; HOMA-IR: Homeostatic Model Assessment Insulin Resistance computed using the formula HOMA-IR = [(Glucose$_{mg/dL}$) × (Insulin$_{\mu U/mL}$)]/405; HOMA-β = [(360x Insulin$_{\mu u/mL}$)/(Glucose$_{mg/dL}$)]%; hs-CRP: high sensitivity C-reactive protein.
†Tabulated values are medians with parenthetic maximum and minimum values, respectively
*P < 0.05 and **P < 0.01 for % change between baseline and week 13 within arms computed using the Wilcoxon Rank Sign Test as described in Methods with (a) uncommon superscript letters indicate significant differences among arms with P-values between arms were computed using a 2-way ANOVA of the log (week/baseline) as described in Methods.

Modified Intent-To-Treat (mITT) Data Analysis—This analysis considers only subjects who completed the study and were judged more than 50% compliant based upon weekly assessment sheets. This resulted in a 35% loss of subjects (n=15 reduced from 23) in the DIET ONLY arm, a 38% loss in the PROG1.1 arm and a 40% loss in the PROG1.2 arm. The mITT analysis is considered the better estimate of efficacy over effectiveness as it assures the subjects adherence to the regimen.

Modified Intent-to-treat analysis results—Groups representing the DIET and PROG treatments from InForm1.1 and InForm1.2 were similar at baseline (Table 26).

TABLE 26

Baseline median cardiometabolic profiles of DIET and PROG subjects for mITT

| Variable | DIET ONLY† (n = 15) | PROG1.1† (n = 13) | PROG1.2† (n = 30) |
|---|---|---|---|
| Gender, % Female | — | — | — |
| Age (yrs) | — | — | — |
| Weight (lb) | 226 (383-165) | 229 (296-170) | 223 (315-173) |
| BMI (kg/m²) | 37.0 (53.0-26.9) | 34.7 (42.7-31.3) | 36.0 (47.7-28.6) |
| Body Fat (lbs) | 108 (149-45.5) | 91.7 (129-68.3) | 96.7 (145-60.3) |
| Waist circumference (in) | 45.0 (61.0-35.5) | 45.8 (52.0-35.0) | 44.0 (53.0-38.0) |
| Systolic BP (mm Hg) | 129 (172-102) | 133 (160-115) | 131 (167-101) |
| Diastolic BP (mm Hg) | 85 (99-73) | 83 (99-78) | 85.8 (108-66) |
| Salivary Nitrite (Morning units) | 3.0 (5-1) | 3.5 (7.5-10) | 3.0 (5.0-0.10) |
| Salivary Nitrite (Noon units) | 5.0 (6.8-2.3) | 3.5 (6.0-0.10) | 4.0 (7.0-1.0) |
| Salivary Nitrite (Evening unit | 5.5 (7.4-2) | 4.0 (7.0-0.10) | 5.0 (7.0-1.5) |
| Total Cholesterol (mg/dL) | 198 (256-173) | 192 (242-137) | 200 (423-153) |
| LDL Cholesterol (mg/dL) | 122 (169-83) | 119 (152-60) | 117 (201-69) |
| TG (mg/dL) | 162 (284-95) | 184 (332-96) | 171 (491-81) |
| HDL Cholesterol (mg/dL) | 46 (67-32) | 38 (80-26) | 42 (64-28) |
| oxLDL (U/L) | 47 (63-35) | 42 (55-23) | 50 (116-6.1) |
| Cholesterol/HDL | 4.7 (7.5-2.7) | 5.1 (7.9-3) | 5.1 (12.4-2.8) |
| LDL/HDL | 2.7 (5.2-1.2) | 3 (4.6-1.4) | 3 (4.8-1.3) |
| TG/HDL | 3.3 (8.6-1.5) | 4.3 (11.4-1.2) | 4.3 (14.4-1.5) |
| oxLDL/HDL | 1.1 (1.8-0.6) | 1.1 (1.8-0.4) | 1.4 (3.4-0.2) |
| Glucose (mg/dL) | 92 (121-71) | 92 (99-84) | 92 (109-64) |
| Insulin (μIU/mL) | 8.2 (18-2.5) | 9.3 (27-3.1) | 9.0 (31-4.6) |

TABLE 26-continued

Baseline median cardiometabolic profiles of DIET and PROG subjects for mITT

| Variable | DIET ONLY† (n = 15) | PROG1.1† (n = 13) | PROG1.2† (n = 30) |
|---|---|---|---|
| HbA1C (%) | 5.8 (7-5.1) | 5.8 (6.2-4.8) | 5.8 (6.8-5.4) |
| HOMA-IR | 2 (4.2-0.5) | 2 (5.8-0.7) | 2.1 (8.2-0.7) |
| HOMA-β | 90 (369-50) | 120 (427-46.5) | 127 (1656-61.2) |
| hs-CRP (mg/L) | 2.6 (41.7-0.8) | 3.6 (9.8-0.4) | 3.3 (15.4-0.5) |
| 10-Year Cardiac Risk/BMI (%) | 7.0 (23-2.3) | 7.1 (23.4-2) | 6.7 (14.5-0.9) |
| 10-Year Cardiac Risk/Lipids (%) | 6.4 (15.4-2.6) | 6.5 (18.4-1.4) | 5.8 (19.9-0.8) |

BMI: Body Mass Index; BP = Blood Pressure; LDL: Low Density Lipoprotein; HDL: High Density Lipoprotein; OxLDL: Oxidized Low Density Lipoprotein; Apo A: Apolipoprotein A1; Apo B: Apolipoprotein B; HbA1c: Glycated Hemoglobin; HOMA-IR: Homeostatic Model Assessment Insulin Resistance computed using the formula HOMA-IR = [(Glucose$_{mg/dL}$) × (Insulin$_{\mu U/mL}$)]/405; HOMA-β = [(360× Insulin$_{\mu UmL}$)/(Glucose$mg/dL$)]%; hs-CRP: high sensitivity C-reactive protein. hs-CRP: high sensitivity C-reactive protein.
†Tabulated values are medians with parenthetic maximum and minimum values, respectively; common superscript letters indicate P > 0.05 computed from Mann-Whitney U-Test Overall results—Table 27 summarizes the effects of DIET, PROG1.1 and PROG1.2 on the clinical variables as median percent changes from baseline for the modified intent-to-treat analysis. In general, the results of the mITT analysis were similar to those of the ITT analysis for the majority of clinical variables as well as weight loss, fat loss, and 5 or 10% responders (Table 27, FIG. 15A, 15B, FIG. 16A, 16B). Changes from baseline were more often greater for all arms reflecting the efficacy of the DIET ONLY and PROG arms when subject are compliant. For example, weight loss for the DIET, PROG1.1 and PROG1.2 was 8.4, 11.8, and 12.5% from baseline, respectively in the mITT analysis versus the 4.4, 7.5 and 8.4% in the ITT analysis.

This example demonstrates the effectiveness and efficacy of the addition of a group of weight loss supplements to diet and lifestyle modifications for increased weight loss and a decrease in 10-year cardiovascular risk.

Example 5—Contrasting Macronutrient Content of InForm1.1 and 1.2 Versus DIET

Tables 28 and 29 describe the macronutrient content of the InForm1.1 and 1.2 PROG as well as the control DIET used in Examples 2 and 4, respectively as percent of daily calories and g macronutrient per day.

TABLE 27

DIET and PROG Effects on Cardio-Metabolic Risk Variables for Modified Intent-To-Treat Analysis

| Variable | DIET (n = 15)† Median % Change† | PROG1.1 (n = 13)† Median % Change† | PROG1.2 (n = 30)† Median % Change† |
|---|---|---|---|
| Weight (lbs) | −8.4** (−0.9 to −20) | −12.5** (−5.8 to −16.3) | −11.8** (−4.3 to −20.5) |
| BMI (kg/m$^2$) | −8.4** (−0.9 to −20) | −12.5** (−5.8 to −16.3) | −11.8** (−4.3 to −20.5) |
| Fat Mass (lbs) | −14** (−2.8 to −27) | −23** (−1.0 to −35) | −18** (−3.7 to −38) |
| Waist circumference (in) | −8.9** (−4.9 to −17) | −11.6** (−4.2 to −16.9) | −8.8** (−2.3 to −20) |
| Systolic BP (mm Hg) | −5.5 (13 to −24) | −12** (7.1 to −24) | −9.0** (7.2 to −32) |
| Diastolic BP (mm Hg) | −7.4* (8.2 to −19) | −12** (2.6 to −21) | −12** (7.7 to −27) |
| Nitrate Strip - Morning | 33** (450 to −33) | 33** (140 to −13) | 33* (3900 to −67) |
| Nitrate Strip - Afternoon | 20 (182.6 to −33) | 67** (7400 to 0.0) | 25** (300 to −17) |
| Nitrate Strip - Evening | 21 (150 to −33) | 63** (7900 to −14) | 20** (133 to −43) |
| Total Cholesterol (mg/dL) | −11* (21 to −34) | −15** (−1.7 to −31) | −19** (54 to −38) |
| LDL Cholesterol (mg/dL) | −11 (65 to −37) | −10 (33 to −31) | −22** (128 to −37) |
| TG (mg/dL) | −32** (7.7 to −55) | −54** (30 to −68) | −40** (8.3 to −80) |
| HDL Cholesterol (mg/dL) | 0.0 (18 to −19) | 0.0 (17 to −12) | −2.9 (56 to −34) |
| oxLDL (U/L) | −20* (37 to −41) | −8.7* (6.7 to −35) | −17** (507 to −56) |
| Cholesterol/HDL | −8.4 (31 to −41) | −19** (1.3 to −27) | −15** (21 to −55.4) |
| LDL/HDL | −6.9 (69 to −44) | −11** (15 to −28) | −14 (47 to −53) |
| TG/HDL | −31** (15 to −60) | −58** (34 −73) | −35** (24 to −87) |
| oxLDL/HDL | −16* (27 to −45) | −14** (19 to −42) | −13* (450 to −69) |
| Glucose (mg/dL) | −2.0 (16 to −37) | −2.3 (12 to −16.2) | −3.2* (28 to −16) |
| Insulin (μIU) | −32* (31 to −71.9) | −30** (42 to −76) | −43** (34 to −82) |
| HbA1c (%) | −1.8 (8.6 to −14) | −1.9 (4.2 to −11) | −4.1** (0.0 to −8.1) |
| HOMA-IR | −29.6* (29.5 to −82.4) | −34.9* (48 to −79.4) | −43.9** (19.8 to −84.1) |
| HOMA-β | −29.6* (59.7 to −74.3) | −26.2** (22.8 to −68.6) | −36.4** (79.7 to −96.5) |
| hs-CRP (mg/L) | −5.2 (439 to −63) | −31** (67 to −55) | −30* (471 to −75) |
| 10-Year Cardiac Risk/BMI (%) | −17* (35 to −54) | −28** (3.5 to −56) | −25** (16 to −67) |
| 10-Year Cardiac Risk/Lipids (%) | −20* (29 to −57) | −36** (3.6 to −69) | −38** (22 to −62) |

Note:
BMI: Body Mass Index; BP: blood pressure; LDL: Low Density Lipoprotein; HDL: High density lipoprotein; TG: triglycerides; High Density Lipoprotein; OxLDL: Oxidized Low Density Lipoprotein; Apo A: Apolipoprotein A1; Apo B: Apolipoprotein B HbA1c: Glycated Hemoglobin; HOMA-IR: Homeostatic Model Assessment Insulin Resistance computed using the formula HOMA-IR = [(Glucose$_{mg/dL}$) × (Insulin$_{\mu U/mL}$)]/405; HOMA-β = [(360× Insulin$_{\mu U/mL}$)/(Glucose$_{mg/dL}$)]%; hs-CRP: high sensitivity C-reactive protein.
†Tabulated values are medians with parenthetic maximum and minimum values, respectively
*P < 0.05 and
**P < 0.01 for % change between baseline and week13 within arms computed using the Wilcoxon Rank Sign Test as described in Methods
(a) uncommon superscript letters indicate significant differences among arms with P-values between arms were computed using a 2-way ANOVA of the log (week/baseline) as described in Methods.

TABLE 28

Macronutrient composition of the study diet as percent of daily calories

| | Mean daily % of calories | | |
|---|---|---|---|
| Composition | DIET | InForm1.1 | InForm1.2 |
| Calories (kcal) | 1510 | 1635 | 1715 |
| Protein | 42.1 | 42.1 | 40.3 |
| Available Carbohydrates | 16.2 | 23.8 | 25.5 |
| Sugars | 2.19 | 3.06 | 2.97 |
| Fiber, g/1000 kcal | | | |
| Dietary | 15.2 | 16.5 | 28.0 |
| Viscous | 3.64 | 5.81 | 17.2 |
| Fat | 41.7 | 34.1 | 34.1 |
| Saturated fatty acids | 6.85 | 5.50 | 5.77 |
| Monounsaturated fatty acids | 19.4 | 14.3 | 13.6 |
| Polyunsaturated fatty acids | 7.45 | 6.88 | 6.56 |
| Dietary cholesterol, mg/1000 kcal | 510 | 404 | 385 |
| Alcohol | — | — | |

Macronutrient dietary components generally associated with the favorable metabolic changes seen in the InForm1.1 and InForm1.2 program studies do not exhibit a consistent difference from the control DIET group that could account for the positive changes described herein. For example, while protein is higher in the test diets, so are the available carbohydrates and sugars. Further, saturated, monounsaturated and polyunsaturated fats are similar over the three dietary treatments either as percent of diet or total daily intake.

Dietary and viscous fiber are both elevated in the InForm programs, 1.7- and 5.5-fold respectively, relative to the DIET program. Additionally, cholesterol content of the two test diets is 21 and 24% lower. Together, these changes have been associated with favorable modifications in blood lipid profiles, but not at the extent demonstrated in these examples.

Therefore, it can be concluded that the novel combination of supplementation with an antimicrobial component, EPA/DHA containing fish oil, an antioxidant blend and a potent vitamin mineral supplement functioned interactively to favorably modify body weights, blood lipids and pro-inflammatory biomarkers better than diet, exercise and behavioral modification alone.

TABLE 29

Macronutrient composition of the study diet as total daily intake

| | Total Daily Intake | | |
|---|---|---|---|
| Composition | DIET | InForm1.1 | InForm1.2 |
| Calories (kcal) | 1510 | 1635 | 1715 |
| Fat (kcal) | 635 | 560 | 590 |
| Protein (g) | 159 | 172 | 173 |
| Available Carbohydrates (g) | 69 | 97 | 120 |
| Sugars (g) | 33 | 50 | 51 |
| Fiber | | | |
| Dietary (g) | 23 | 27 | 48 |
| Viscous (g) | 5.5 | 9.5 | 30 |
| Fat (g) | 70 | 62 | 65 |
| Saturated fatty acids (g) | 11.5 | 10.0 | 11.0 |
| Monounsaturated fatty acids (g) | 32.5 | 26.0 | 26.0 |
| Polyunsaturated fatty acids (g) | 12.5 | 12.5 | 12.5 |
| Trans fat | 1.0 | 1.0 | 1.0 |
| Dietary cholesterol (mg) | 770 | 660 | 660 |
| Alcohol (g) | — | — | — |

Example 6—Two Formulations of a Four-Component Phytocomplex (PC4) Exhibit Synergy in Peroxynitrite (ONOO$^-$) Scavenging Capacity The potential for synergy of a novel, four-component phytocomplex (PC4) relative to the sum of the expected contributions of its components in scavenging peroxynitrite when tested at two formulations was evaluated.

Methodology—Peroxynitrite (ONOO$^-$) scavenging capacity was measured according to the procedure described by Kim et al. [Kim, J. Y., Kim, H. S., Kang, H. S., Choi, J. S., Yokozawa, T., and Chung, H. Y. (2008) Antioxidant potential of dimethyl lithospermate isolated from *Salvia miltiorrhiza* (red sage) against peroxynitrite, J Med Food 11, 21-28] with the modification that assays were conducted in 96-well microtiter plates instead of cuvettes.

Calculations—The median inhibitory concentration (IC50) for oxygen radical scavenging activity was calculated using CalcuSyn (BIOSOFT, Ferguson, MO). This statistical package performs multiple drug dose-effect calculations using the median effect methods described by T-C Chou and P. Talaly [(1984) Quantitative analysis of dose-effect relationships: the combined effects of multiple drugs or enzyme inhibitors. Adv Enzyme Regul 22, 27-55.] hereby incorporated by reference.

Briefly, the analysis correlates the "Dose" and the "Effect" in the simplest possible form: fa/fu=(C/Cm)m, where C is the concentration or dose of the compound and Cm is the median-effective dose signifying the potency. Cm is determined from the x-intercept of the median-effect plot. The fraction affected by the concentration of the test material is fa and the fraction unaffected by the concentration is fu (fu=1−fa). The exponent m is the parameter signifying the sigmoidicity or shape of the dose-effect curve; it is estimated by the slope of the median-effect plot.

The median-effect plot is a graph of x=log(C) vs y=log (fa/fu) and is based on the logarithmic form of Chou's median-effect equation. The goodness of fit for the data to the median-effect equation is represented by the linear correlation coefficient r of the median-effect plot. Usually, the experimental data from enzyme or receptor systems have an r>0.96, from tissue culture an r>0.90 and from animal systems r>0.85.

The median inhibitory concentration ($IC_{50}$) for oxygen radical scavenging activity in this example was calculated by interpolating the concentration required for the inhibition of the fluorescence decay by 50 percent within 20 minutes. Synergy of test components was then quantified using the combination index (CI) parameter. This parameter defines only the additive effect rather than synergism or antagonism. Synergy, however, was defined as a more than expected additive effect (CI>1), and antagonism as a less than expected additive effect (CI<1) as described below.

Expected median inhibitory concentrations of any multi-component combination were estimated using the relationship:

$$[1/\text{Expected } IC_{50}] = [Fa/IC_{50A}] + [Fb/IC_{50B}] + \ldots + [Fn/IC_{50N}]$$

and $Fa + Fb + \ldots + Fn = 1$ where Fa=mole fraction of component A in the combination and Fn=the mole fraction of the $n^{th}$ component combination and $IC_{50A}$=the observed $IC_{50}$ of the component A. The CI was then calculated thusly, CI=Expected [$IC_{50}$]/Observed [$IC_{50}$]. Using the designation of CI=1 as the additive effect, for mutually exclusive compounds that have the same mode of action or for mutually non-exclusive drugs that have totally independent modes of action the following relationships are defined: CI<1, =1, and >1 indicating antagonism, additivity and synergy, respectively.

PC4 Material—PC4 consisted of components listed in Tables 30 and 31 and as described in Example 1. Relative amounts of the individual four components were 1:1:1:1=PC4.1 (Table 13) and 6:3:1:1=PC4.2.

Conclusion—The $IC_{50}$ of PC4.1 was 0.216 µg/mL, while the calculated, expected $IC_{50}$ was 0.420 µg/mL resulting in a CI=1.95. Thus, PC4.1 synergistically produced 2.0-times the peroxynitrite-scavenging capacity than expected from the sum of its components.

TABLE 30

Determining Combination Index for Peroxynitrite ($ONOO^-$) Scavenging Capacity of a Four-component Phytocomplex (PC4.1)

| Test Material | Observed $IC_{50}$ [µg/mL] | Relative Amount [F] | $Fn/[IC_{50}]$ [µg/mL]$^{-1}$ |
|---|---|---|---|
| Apple fruit† | 0.875 | 0.250 | 0.286 |
| Grape seed† | 0.472 | 0.250 | 0.530 |
| Green tea leaf† | 0.185 | 0.250 | 1.352 |
| Olive leaf† | 1.17 | 0.250 | 0.214 |
| Phytocomplex (PC4.1) | 0.216 | 1.00 | 2.382 |

†extract/*concentrate/** Phytocomplex PC4.1 contains relative amounts [F] of each of the four test materials; Expected IC50 for PC4.1 = 1/[2.382] = 0.420 µg/mL.

Conclusion—With CI=1.95, PC4.1 unexpectedly produced 2.0-times the peroxynitrite-scavenging capacity than expected from the sum of its components

TABLE 31

Determining Combination Index for Peroxynitrite ($ONOO^-$) Scavenging Capacity of a Four-component Phytocomplex (PC4.2)

| Test Material | Observed $IC_{50}$ [µg/mL] | Relative Amount [F] | $Fn/[IC_{50}]$ [µg/mL]$^{-1}$ |
|---|---|---|---|
| Apple fruit† | 0.875 | 0.545 | 0.623 |
| Grape seed† | 0.472 | 0.0909 | 0.193 |
| Green tea leaf† | 0.185 | 0.273 | 1.475 |
| Olive leaf† | 1.17 | 0.0909 | 0.078 |
| Phytocomplex (PC4.2) | 0.201 | 1.000 | 2.369 |

†extract/*concentrate/** Phytocomplex PC4.2 contains relative amounts [F] of each of the four test materials; Expected $IC_{50}$ for PC4.2 = 1/[2.369] = 0.422 µg/mL.

Results—The $IC_{50}$ of PC4.2 was 0.201 µg/mL, while the calculated, expected $IC_{50}$ was 0.422 µg/mL resulting in a CI=2.10. Thus, PC4.2 synergistically produced 2.0-times the peroxynitrite-scavenging capacity than expected from the sum of its components.

Figure 17:
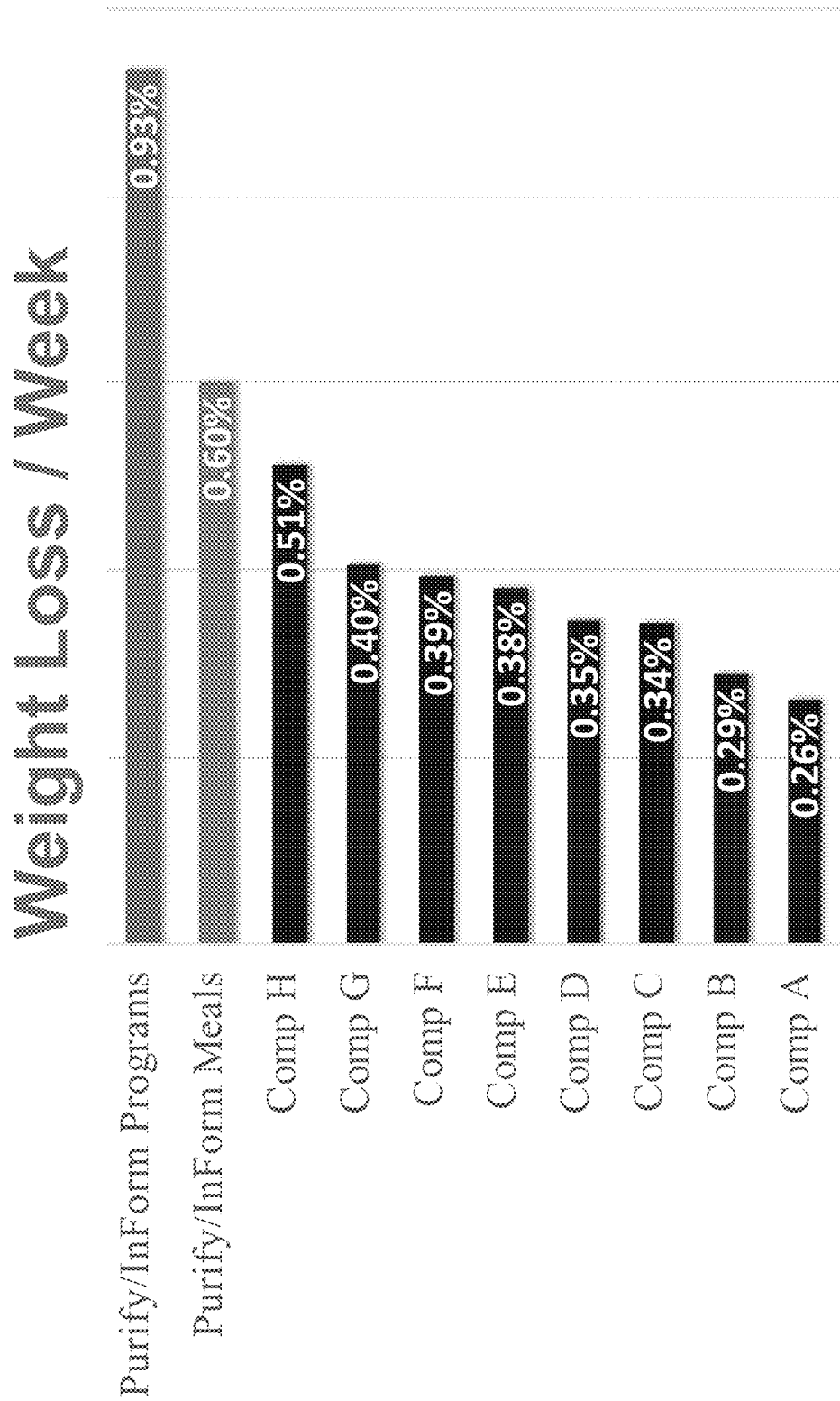
FIG. 17 graphically depicts the weight loss per week of subjects using disclosed systems and methods as compared to example competitor systems and methods.

Conclusion—With CI=2.10, PC4.2 unexpectedly produced 2.0-times the peroxynitrite-scavenging capacity than expected from the sum of its components Example 7—Meta-Analysis of Weight Loss Results Achieved in the InForm and Purify Programs Vs Published Commercial Programs Methods Eight studies were selected from the literature that describes various weight loss programs using similar protocols to the previously described examples for the InForm and Purify programs. Weight loss per week was estimated from the available data and presented in FIG. 17.

Results—As seen in this figure, the Purify/InForm meal program alone was superior to seven of the programs and similar to Comp H, respectively, 0.60 vs 0.51% body weight per week. The supplemented Purfiy/InForm Program achieved 1.8 to 3.6 times the percent weight loss per week as the eight published commercial programs.

Conclusion—The result of this meta-analysis underscores the unique value of the nutraceutical supplementation of both the Purify and InForm programs.

Thus, there have been disclosed a novel detoxification system and its method of use. It will be readily apparent to those skilled in the art, however that various changes and modifications of an obvious nature may be made without departing from the spirit of the disclosed invention embodiments, and all such changes and modifications are considered to fall within the scope of the invention as recited herein, including in the appended claims.

What is claimed:

1. A detoxification system, comprising effective amounts of:
    (a) a probiotic component;
    (b) a fiber component;
    (c) a circulation enhancing component comprising one or more of red beet root, L-arginine, L-glutamine, vitamin C, vitamin B12, folic acid, vitamin B6, thiamin, and vitamin D; and
    (d) a mixture comprising an apple extract, a green tea extract, and an olive extract, wherein the mixture is included as part of the fiber component, the circulation enhancing component, or both the fiber component and the circulation enhancing component;
    wherein the detoxification system increases urinary heavy metal excretion, decreases a fecal zonulin level, decreases a fecal calprotectin level, decreases a serum lipopolysaccharide binding protein (LBP) level, increases at least one of a salivary nitrite level and a serum arginine level, or a combination thereof in a subject as compared to a baseline level prior to administration of the detoxification system in an effective dosing regimen.

2. The detoxification system of claim 1, wherein the probiotic component comprises at least one of *Bacillus* spp., *Lactobacillus* spp., *Bifidobacterium* spp., and *Streptococcus* spp.

3. The detoxification system of claim 2, wherein the *Bacillus* spp. comprises *Bacillus coagulans*, the *Lactobacillus* spp. comprises *L. rhamnosus*, *L. acidophilus*, *L. brevis*, *L. bulgaricus*, *L. plantarum*, *L. casei*, *L. salivarius*, or a combination thereof, the *Bifidobacterium* spp. comprises *B. bifidum*, *B. infantis*, *B. longum*, or a combination thereof, and the *Streptococcus* spp. comprises *Streptococcus* thermophiles.

4. The detoxification system of claim 1, wherein the probiotic component comprises a daily dose of about 2 billion colony forming units (cfu) to about 60 billion cfu of probiotic.

5. The detoxification system of claim 1, wherein the fiber component comprises inulin, fructooligosaccharide, cellulose, prebiotic fibers, or a combination thereof.

6. The detoxification system of claim 1, wherein the probiotic component is formulated as a solid oral dosage form.

7. The detoxification system of claim 1, wherein the circulation enhancing component further comprises at least one component selected from the group consisting of grape extract, *stevia* leaf extract, watermelon whole fruit extract, inulin, and pomegranate fruit juice concentrate.

8. The detoxification system of claim 1, wherein the mixture further includes grape extract and the apple extract, the grape extract, the green tea extract, and the olive extract are present at a weight ratio of from about 1:1:1:1 to about 6:1:3:1.

9. The detoxification system of claim 1, wherein the circulation enhancing component further comprises at least one component selected from the group consisting of natural citrus sweetener, citrus blend natural flavor, natural cherry flavor, lemonade flavor, and D-ribose.

10. The detoxification system of claim 1, wherein the circulation enhancing component further comprises at least one component selected from the group consisting of citric acid, malic acid, magnesium oxide, and silicon dioxide.

11. The detoxification system of claim 5, wherein the fiber component further comprises one or more components selected from the group consisting of *psyllium* hulls, apple fruit fiber, flax seeds, guar gum, acacia gum, cabbage leaf, broccoli flowers, rosemary leaf, tomato fruit, turmeric root, carrot root, and inulin.

12. The detoxification system of claim 5, wherein the fiber component further comprises at least one component selected from the group consisting of chlorophyllin, l-glutamine, and zinc.

13. The detoxification system of claim 5, wherein the mixture is included as part of the fiber component and at least one component selected from the group consisting of the apple extract, the green tea extract, and the olive extract include fiber.

14. The detoxification system of claim 5, wherein the fiber component further comprises at least one component selected from the group consisting of vitamin B1, vitamin B2, vitamin B6, vitamin B12, and vitamin D.

15. The detoxification system of claim 1, further comprising one or more individual components selected from the group consisting of iron, docosahexaenoic acid (DHA), eicosapentaenoic acid (EPA), calcium, niacin, folic acid, biotin, panthothenic acid, phosphorus, iodine, magnesium, zinc, selenium, copper, manganese, chromium, potassium, inositol, p-Aminobenzoic acid (PABA), choline, bitartrate, lycopene, lutein, antioxidants, dandelion root, alfalfa aerial parts, asparagus stem, broccoli flowers, cabbage leaf, hesperidin bioflavonoid extract, lemon bioflavonoid extract, rutin, rose hips extract, chlorophyll, kelp leaf, kelp stem, cranberry fruit, mangosteen fruit, carrot root, spinach leaf, spinach stem, tomato fruit, acai berry, pomegranate fruit extract, l-leucine, l-lysine, l-valine, l-isoluecine, l-phenyalanine, l-threonine, l-arginine, l-citrulline, l-methionine, l-tyrosine, l-cysteine, or combinations thereof.

16. The detoxification system of claim 1, wherein the mixture is included as part of the circulation enhancing component.

17. The detoxification system of claim 1, wherein the apple extract is a fruit extract, the green tea extract is a leaf extract, and the olive extract is a leaf extract.

18. The detoxification system of claim 8,
wherein the grape extract includes an extract of grape polyphenol, grape seed, grape skin, grape flesh/fruit, grape vine, grape leaf, or a combination thereof;
wherein the apple extract includes an extract of apple skin, apple flesh/fruit, apple seed, apple stalk, apple stem, apple leaf, or a combination thereof;
wherein the green tea extract includes an extract of green tea leaf, green tea seed, green tea stem, green tea flower, or a combination thereof; and
wherein the olive extract includes an extract of olive leaf, olive seed, olive pulp, olive fruit, olive stem, or a combination thereof.

* * * * *